(12) United States Patent
Bata et al.

(10) Patent No.: US 9,073,853 B2
(45) Date of Patent: Jul. 7, 2015

(54) CYCLOALKANE CARBOXYLIC ACID DERIVATIVES AS CXCR3 RECEPTOR ANTAGONISTS

(71) Applicant: Sanofi, Paris (FR)

(72) Inventors: Imre Bata, Budapest (HU); Peter Buzder-Lantos, Budapest (HU); Attila Vasas, Dunakeszi (HU); Veronika Bartane Bodor, Budapest (HU); Gyorgy Ferenczy, Budapest (HU); Zsuzsanna Tomoskozi, Budapest (HU); Gabor Szeleczky, Budapest (HU); Sandor Batori, Budapest (HU); Martin Smrcina, Tucson, AZ (US); Marcel Patek, Tucson, AZ (US); Aleksandra Weichsel, Tucson, AZ (US); David Squire Thorpe, Tucson, AZ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/294,885

(22) Filed: Jun. 3, 2014

(65) Prior Publication Data

US 2014/0288106 A1   Sep. 25, 2014

Related U.S. Application Data

(63) Continuation of application No. PCT/HU2012/000128, filed on Dec. 3, 2012.

(30) Foreign Application Priority Data

Dec. 6, 2011  (EP) .................................... 11462023

(51) Int. Cl.

| | | |
|---|---|---|
| *C07D 207/408* | (2006.01) | |
| *C07D 209/52* | (2006.01) | |
| *C07D 277/34* | (2006.01) | |
| *C07D 239/54* | (2006.01) | |
| *C07D 417/12* | (2006.01) | |
| *C07D 209/48* | (2006.01) | |
| *C07D 207/40* | (2006.01) | |
| *C07D 405/12* | (2006.01) | |
| *C07D 251/20* | (2006.01) | |
| *C07D 263/44* | (2006.01) | |
| *C07D 221/20* | (2006.01) | |

(Continued)

(52) U.S. Cl.
CPC ............ *C07D 207/408* (2013.01); *A61K 31/53* (2013.01); *A61K 31/427* (2013.01); *A61K 31/506* (2013.01); *A61K 31/45* (2013.01); *A61K 31/513* (2013.01); *A61K 31/438* (2013.01); *A61K 31/403* (2013.01); *A61K 31/4166* (2013.01); *A61K 31/4015* (2013.01); *A61K 31/4035* (2013.01); *A61K 31/421* (2013.01); *A61K 31/426* (2013.01); *C07D 211/88* (2013.01); *C07D 221/20* (2013.01); *C07D 233/74* (2013.01); *C07D 405/12* (2013.01); *C07D 239/54* (2013.01); *C07D 413/12* (2013.01); *C07D 417/12* (2013.01); *C07D 251/20* (2013.01); *C07D 263/44* (2013.01); *C07D 207/40* (2013.01); *C07D 277/34* (2013.01); *C07D 209/48* (2013.01); *C07D 209/94* (2013.01); *C07D 209/52* (2013.01)

(58) Field of Classification Search
CPC ............ C07D 207/408; C07D 209/52; C07D 277/34; C07D 239/54; C07D 417/12; C07D 209/48; C07D 207/40; C07D 405/12; C07D 251/20; C07D 263/44; C07D 221/20; C07D 413/12; C07D 233/74; C07D 211/88; A61K 31/53; A61K 31/506; A61K 31/513; A61K 31/45; A61K 31/438; A61K 31/4015; A61K 31/4035; A61K 31/4166; A61K 31/403; A61K 31/421; A61K 31/426; A61K 31/427
See application file for complete search history.

(56) References Cited

U.S. PATENT DOCUMENTS 5,478,850 A * 12/1995 Hindley et al. ................ 514/369

FOREIGN PATENT DOCUMENTS

| EP | 0080334 | 6/1983 |
| EP | 1437344 | 9/2002 |

(Continued)

OTHER PUBLICATIONS

Knight et al. Bioorganic & Medicinal Chemistry 2008, 18, 629-633.*
Krausthausen et al. AJP Nov. 2011, vol. 179, No. 5, 2346-2359.*
Sorensen et al. Br J Ophthalmol 2004, 88, 1146-1148.*
Billottet et al. Biochimica et Biophysica Acta 2013, 1836, 287-295.*
Antonelli et al. Autoimmunity Reviews 2014, 13, 272-280.*
International Search Report for WO2013/084013 dated Jun. 13, 2013.

(Continued)

*Primary Examiner* — Matthew Coughlin
(74) *Attorney, Agent, or Firm* — Ronald G. Ort

(57) ABSTRACT

The present invention relates to compounds of formula 1

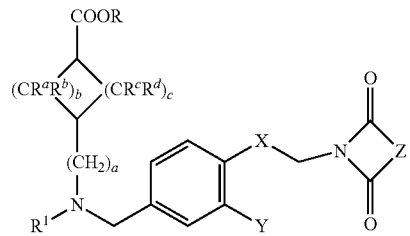

that are useful for the preventive or therapeutic treatment of diseases caused by abnormal activation of CXCR3 chemokines. The invention relates furthermore to a process for the preparation of said compounds, to pharmaceutical compositions containing said compounds and to novel intermediates used in the preparation of said compounds.

16 Claims, No Drawings

(51) Int. Cl.

| | |
|---|---|
| C07D 413/12 | (2006.01) |
| C07D 233/74 | (2006.01) |
| C07D 211/88 | (2006.01) |
| A61K 31/53 | (2006.01) |
| A61K 31/506 | (2006.01) |
| A61K 31/513 | (2006.01) |
| A61K 31/45 | (2006.01) |
| A61K 31/438 | (2006.01) |
| A61K 31/4015 | (2006.01) |
| A61K 31/4035 | (2006.01) |
| A61K 31/4166 | (2006.01) |
| A61K 31/403 | (2006.01) |
| A61K 31/421 | (2006.01) |
| A61K 31/427 | (2006.01) |
| A61K 31/426 | (2006.01) |
| C07D 209/94 | (2006.01) |

(56) References Cited

FOREIGN PATENT DOCUMENTS

| | | |
|---|---|---|
| WO | WO 92/07839 | 5/1992 |
| WO | WO 03/087063 | 10/2003 |
| WO | WO 2006/004924 | 1/2006 |
| WO | WO 2009/094168 | 7/2009 |
| WO | WO 2009/105435 | 8/2009 |

OTHER PUBLICATIONS

Crosignani, et al., Discovery of a Novel Series of CXCR3 Antagonists, Bioorganic & Medicinal Chemistry Letters, vol. 20, (2010), 3614-3617.
Wijtmans, et al., Towards Small-Molecule CXCR3 Ligands With Clinical Potential, ChemMedChem, vol. 3, pp. 861-872, (2008).
Groom, et al., CXCR3 in T Cell Function, Experimental Cell Research, vol. 317, (2011), pp. 620-631.
Liu, et al., CXCL 10/IP-10 in Infectious Diseases Pathogenesis and Potential Therapeutic Implications, Cytokine & Growth Factor Reviews, vol. 22, (2011), pp. 121-130.
Vandercappellen, et al., The Role of the CXC Chemikines Platelet Factor-4 (CXCL4/PF-4) and its Variant (CXCL4L1/PF-4var) in Inflammation, Angiogenesis and Cancer, Cytokine & Growth Factor Reviews, vol. 22, (2011), pp. 1-18.
Romagnani, et al., CXC Chemokines: The Regulatory Link Between Inflammation and Angiogenesis, Trends in Immunology, vol. 25, No. 4, (2004), pp. 201-209.
Campanella, et al., CXCL10 Can Inhibit Endothelial Cell Proliferation Independently of CXCR3, PLOS ONE, vol. 5, No. 9, (2010), e12700, pp. 1-10.
Strieter, et al., CXC Chemokines in Angiogenesis, Cytokine & Growth Factor Reviews, vol. 16, (2005), pp. 593-609.
Muller, et al., Review: The Chemokine Receptor CXCR3 and its Ligand CXCL9, CXCL10 and CXCL11 in Neuroimmunity—A Tale of Conflict and Conundrum, Neuropathology and Applied Neurobiology, (2010), vol. 36, pp. 368-387.
Pease, et al., The Attraction of Chemokines as a Target for Specific Anti-Inflammatory Therapy, British Journal of Pharmacology, (2007), vol. 147, pp. S212-S221.
Donnelly, et al., Chemokine Receptors as Therapeutic Targets in Chronic Obstructive Pulmonary Disease, Trends in Pharmacological Science, vol. 27, No. 10, pp. 546-553, (2006).
Uno, et al., Expression with Chemokines, CXC Chemokine Ligand 10 (CXCL10) and CXCR3 in the Inflamed Islets of Patients With Recent-Onset Autoimmune Type 1 Diabetes, Endocrine Journal, (2010), vol. 57, No. 11, pp. 991-996.
Singh, et al., CXCL10 T Cells and NK Cells Assist in the Recruitment and Activation of CXCR3 and CXCRL11 Leukocytes During Mycobacteria-Enhanced Colitis, BMC Immunology, (2008), vol. 9, No. 25, pp. 1-13.
Pease, et al., Chemokine Receptor Antagonists: Part 2, Expert Opin. Ther. Patents, (2009), vol. 19, No. 2, pp. 199-221.
Hansel, et al., New Drugs for Exacerbations of Chronic Obstructive Pulmonary Disease, Lancet, vol. 374, (2009), pp. 744-755.
Krueger, et al., Psoriasis Pathophysiology: Current Concepts of Pathogenesis, Ann. Rheum. Dis., vol. 64, Suppl. II, pp. ii30-ii36, (2005).
Hancock, et al., Requirement of the Chemokine Receptor CXCR3 for Acute Allograft Rejection, J. Exp. Med., vol. 192, No. 10, pp. 1515-1519, 2000.
Lammers, et al., Identification of a Novel Immunomodulatory Gliadin Peptide that Causes Interleukin-8 Release in a Chemokine Receptor CXCR3-Dependent Manner Only in Patients With Coeliac Disease, Immunology, vol. 132, pp. 432-440, (2010).
Brightling, et al., The CXCL10/CXCR3 Axis Mediates Human Lung Mast Cell Migration to Asthmatic Airway Smooth Muscle, American Journal of Respiratory and Critical Care Medicine, vol. 171, pp. 1103-1108, (2005).
Meller, et al., Chemokines in the Pathogenesis of Lichenoid Tissue Reactions, J. Investigative Dermatology, vol. 129, pp. 315-319, (2009).
Sonogashira, et al., A Convenient Synthesis of Acetylenes : Catalytic Substitution of Acetylenic Hydrogen With Bromoalkenes, Iodoarenes, and Bromopyridines, Tetrahedron Letters, vol. 50, pp. 4467-4470, (1975).
Miyaura, et al., A New Stereospecific Cross-Coupling by the Palladium-Catalyzed Reaction of 1-Alkenylboranes With 1-Alkenyl or 1-Alkynyl Halides, Tetrahedron Letter, vol. 36, pp. 3437-3440, (1979).
Hoerning, et al., Subsets of Human CD4+ Regulatory T Cells Express the Peripheral Homing Receptor CXCR3, Eur. J. Immunol., (2011), vol. 41, pp. 2291-2302.
Groom, et al., CXCR3 Ligands: Redundant, Collabarative and Antagonistic Functions, Immunology and Cell Biology, (2011), vol. 89, pp. 207-215.
Chen, et al., Expression of Chemokine Receptor CXCR3 by Lymphocytes and Plasmacyloid Dendritic Cells in Human Psoriatic Lessions, Arch Dermatol Res., vol. 302. 113-123, (2010).
Wenzel, et al., CXCR3 <-> Ligand-Mediated Skin Inflammation in Cutaneous Lichenoid Graft-Versus-Host Disease, J. Am. Acad. Dermatol., vol. 58, pp. 437-442, (2008).
Sorensen, et al., Optic Neuritis: Chemokine Receptor CXCR3 and its Ligands, Br. J. Ophthalmol., vol. 88, pp. 1146-1148, (2004).
Nishimura, et al., Chemokines as Novel Therapeutic Targets for Inflammatory Bowel Disease, Annals of New York Acad. Sci., vol. 1173, pp. 350-356, (2009).
Lacotte, et al., CXCR3, Inflammation, and Autoimmune Diseases, Annal of N.Y. Acad. Sci., vol. 1173, pp. 310-317, (2009).
Shimada, et al., The Role of the CXC L10/ CXCR3 System in Type Diabetes, Review of Diabetic Studies, vol. 6 No. 2, pp. 81-84, (2009).
Inoue, et al., N-Allylation of Imides Catalyzed by Palladium (0), Bull. Chem. Soc. Jpn., vol. 57, pp. 3021-3022, (1984).
Sauty, et al., CXCR3 Internationalization Following T Cell-Endothelial Cell Contact: Preferential Role of IFN-Inducible T Cell a Chemoattractant (CXCL11), J Immunol, (2001), vol. 167, pp. 7084-7093.

* cited by examiner

CYCLOALKANE CARBOXYLIC ACID DERIVATIVES AS CXCR3 RECEPTOR ANTAGONISTS

The present invention relates to compounds that are useful as an active ingredient of a medicament for preventive and/or therapeutic treatment of diseases caused by abnormal activation of CXCR3 chemokines.

Chemokines are a large family of small soluble proteins of about 8 to 10 kDa in size. One of the major roles of chemokines is to direct the migration of immune cells. The mechanism by which the movement of cells is guided is the chemical attraction of the cells expressing the relevant chemokine receptor on their surface toward the concentration gradient of the corresponding chemokine.

Some chemokines are homeostatic in function as they regulate the trafficking of cells in a day to day manner. Such homeostatic chemokines, for example direct the homing of lymphocytes to the lymph nodes or they have effect on development by promoting or inhibiting the growth of new blood vessels—thus exerting angiogenic or angiostatic effects.

Other chemokines are expressed in response to inflammation or injury. These inflammatory chemokines regulate the recruitment of specific leukocyte populations into the inflamed tissue that in turn they can elicit the release of specific regulatory and enzymatic factors from the activated immune cells. The expression of these inflammatory chemokines is typically induced by interleukin-1 (IL-1) or interferon-γ (IFN-γ) from various types of cells.

Chemokines exert their function via binding to specific chemokine receptors that are expressed on the cell surface. The chemokine receptors are about 340-360 amino acids long, and they belong to the G-protein coupled receptor (GPCR) super family. To date, approximately 50 chemokines have been identified. Many of them can bind to the same receptor and particular chemokines can also bind to several chemokine receptors. Presently we know altogether 20 different chemokine receptors for these 50 known chemokines [Groom, J. R. and Luster, A. D. 2011. Immunology and Cell Biology, 1-9]. More recently different splice variants have also been described for some chemokine receptors that may have different expression patterns and different physiological or pathophysiological roles.

CXCR3 is an inflammatory chemokine receptor which is predominantly expressed on activated immune cells such as the CD4+ (Th1 helper) and CD8+ (CTL cytotoxic or Tc) T lymphocytes. CXCR3 is absent on naïve T lymphocytes, but its cell surface expression is rapidly induced following T cell activation by dendritic cells. CXCR3 is also expressed on innate lymphocytes such as natural killer cells (NK) and NKT cells, on plasmacytoid dendritic cells (pDC) [Groom, J. R. and Luster, A. D. 2011. Immunology and Cell Biology, 1-9], on inflammatory neutrophils and macrophages.

CXCR3 is selectively activated by three interferon-inducible chemokines, CXCL9 (also termed as Mig), CXCL10 (IP-10) and CXCL11 (I-TAC). Activation of CXCR3 by these endogenous agonists elicits intracellular $Ca^{2+}$ mobilization via phospholipases C (PLC) and, in addition, activation of both mitogen-activated protein kinase (MAP-kinase) and PI3-kinase [Liu, M; Guo, S; Hibbert, J. M; Jain, V; Sinh, N Wilson, N. O; and Stiles, J N K. 2011. Cytokine & Growth Factor Reviews, 22: 121-130.]. These intracellular events finally result in stimulation of lymphocyte migration and proliferation. CXCR3 plays a key role in selective recruitment of activated immune cells to the site of inflammation. Once recruited, cytotoxic T cells (CTL), through the release of perforin and granzyme B, induce apoptosis, thereby contributing to local tissue damage and subsequent remodelling. At the site of inflammation the recruited Th1 and CTL cells release IFN-gamma that stimulates epithelial cells and macrophages to further release of CXCR3 agonists that leads to a persistent inflammatory activation.

Strong Th1 and CTL responses are beneficial during acute infection, but these responses must be counterbalanced to prevent unwanted tissue destruction and chronic immunopathological changes [Groom, J. R. and Luster, A. D. 2011. Experimental Cell Research 317: 620-631]. In this respect CXCR3 antagonists are suggested to have significant therapeutic relevance.

More recent studies demonstrated that CXCR3 is also expressed on human CD25+ FOXP3+ regulatory CD4+ T cells (Treg) and the level of CXCR3 increases on Treg cells following activation [Vandercappellen, J et al, 2011. Cytokine & Growth Factor Reviews 22: 1-18.]. This observation suggests that CXCR3 may participate in mediation of trafficking of Treg cells. Treg cells migrate to the peripheral sites of inflammation, where they exert suppressive activity on CD4+ Th1 and CD8+ CTL cells [Hoerning, A et al 2011. Eur J Immunol, online manuscript, accepted: Apr. 26, 2011. DOI: 10.1002/eji.201041095]. Thus Treg cells are important for suppressing the immune responses, maintaining immune tolerance and preventing autoimmune responses.

For the time being little is known about the expression pattern of CXCR3 on Treg subsets or the association of CXCR3 with Treg immunoregulatory functions. However, this finding may explain some reported variable functional effects of CXCR3 blockade in different animal models [Hoerning, A et al 2011. Eur J Immunol, online manuscript, accepted: Apr. 26, 2011. DOI: 10.1002/eji.201041095] or the variable effects of CXCR3 blockade in different types of allograft rejection.

As of today, there are three splice variants for CXCR3 described in humans: CXCR3-A, CXCR3-B [Romagnani, P; Lasagni, L; Annunziato, F; Serio, M. and Romagnani, S. 2004. TRENDS in Immunology, 25: 201-209.] and CXCR3-alt. CXCR3-A is the most abundant variant, it couples to Gi/o type of G-proteins and it mediates chemotaxis and cell proliferation.

The splice variant CXCR3-B is thought to be expressed on endothelial and vascular smooth muscle cells and mediates angiostatic effects [Strider, R. M; Burdick, M. D; Gomperts, B. N; Belperio, A; Keane, M. P. 2011. Cytokine & Growth Factor Reviews 16:593-609.]. CXCR3-B can bind not only the three well known CXCR3 agonists, CXCL9 (Mig), CXCL10 (IP-10) and CXCL11 (I-TAC). but also a forth one, CXCL4 (PF-4), which is a selective, CXCR3-B specific chemokine agonist. Activation of CXCR3-B is supposed to mediate the activation of the Gs, the stimulatory type of G-proteins that in turn causes an intracellular cAMP rise, which finally results in angiostatic effects and inhibition of cell proliferation. More recent studies, however, showed that the alternative CXCR3-B splice variant does not exist in mice [Campanella, G. S. V; Colvin, R. A; and Luster, A. D. 2010. PLoS ONE 5(9): e12700. doi:10.1371/journal.pone.0012700] and, in addition to it, the same authors in their experiments with human endothelial cells also demonstrated that CXCL10 can inhibit endothelial cell proliferation independently of CXCR3 receptors. As of today, there are some controversial observations on the putative roles of the different alternative CXCR3 splice variants and thus further studies are still needed in order to clarify and understand their physiological and pathophysiological roles.

On the other hand, it is widely accepted that T lymphocytes play crucial regulatory function in the immune system [Wijtmans, M; Verzijl, D; Leurs, R; de Esch, I. J. P; and Smit, M. J. 2008. Chem Med Chem. 3:861-872.] and [Muller, M; Carter, M. J; Hofert, J; and Campbell, I. L. 2010. Neuropathology and Applied Neurobiology, 36:368-387.]. Their special roles are also indicated by the fact that 15 chemokine receptors out of the 20 known ones, are expressed among the different subpopulations of T lymphocytes [Pease and Williams, Br. J. Pharmacol. 2006. 147, S212]. T cells are implicated in many inflammatory diseases.

Clinical evidences showed significant overexpression of CXCR3 receptor and/or its endogenous agonists (CXCL10, CXCL11) in multiple autoimmune or inflammatory diseases, such as e.g.

(i) in peripheral airways of COPD patients [Donnelly, L. E. and Barnes, P. J. Trends in Pharmacol Sci 27(10): 564-553.],
(ii) in skin biopsies from patients with moderate to severe psoriasis [Chen, S-C; Groot, M.; Kinsley, D; Laverty, M; McClanahan, T; Arreaza, M; Gustafson, E. L; Teunissen, M. B. M; Rie, M. A; Jay, S. F; and Kraan, M. 2010. Arch. Dermatol. Rev. 302: 113-123],
(iii) in lymph nodes and islets of type 1 diabetic patients [Uno, S; Imagawa, A; Saisho, K; Okita, K; Iwahashi, H; Hanafusai, T; and Shimomura, I. 2010. Endocrine Journal. 57(11): 991-996.]
(iv) in acute allograft rejection (lung, heart, kidney and skin grafts) [Wenczel, J. Lucas, S; Zahn, S; Mikus, S; Metze, D; Stadter, S, et al, 2008. J. Am. Acad. Dermatol. 58:437-442.]
(v) in colon biopsies of patients with ulcerative colitis [Singh, U. P. Singh, R; Singh, S; Karls, R. K; Quinn, F. D; Taub, D. D; and Lillard Jr J. W. 2008. BMC Immunology 9:25]
and (vi) in thymus from myasthenia gravis patients [Pease, J. E and Horuk, R. 2009. Expert Opin Ther Patents, 19 (2): 199-221].

In animals, CXCR3-KO mice display blocked T cell migration into bronchoalveolar space following noxious stimuli such as cigarette smoke (murine model of COPD). CXCL10-gene deficient or CXCR3-KO mice showed prolonged allograft survival in murine models of transplant rejection (cardiac and pancreatic island allografts).

Blocking the activation of CXCR3 by antagonists represents a possible approach for the treatment of diseases such as COPD [Hansel, T. T. and Barnes, P. J. 2009. Lancet, 374:744-755], psoriasis [Krueger, J. G. and Bowcock, A. 2005. Ann. Rheum. Dis. 64: Suppl. II.: ii30-ii36], graft/transplant rejection [Hancock, W. W; Lu, B; Gao, W; Cziszmadia, V; Faia, K; King, J. A; Smileey, S. T.; Ling, M; Gearad, N. P.; and Gerard, C. 2000. J Exp Med 192:1515-1519.], ophthalmological diseases [Sorensen, T. L.; Roed, H; Sellebjerg, F. 2004. Br. J. Ophthalmol. 88:1146-1148.], celiac disease [Lammers, K. M.; Khandelwal, S; Chaudhry, F; Kryszak, D; Puppa, E. L; Casolaro; V; and Fasano, A. 2010. Immunology, 132:432-440.], inflammatory bowel disease (IBD) [Nishimura, M; Kuboi, Y; Muramato, K; Kawano, T; and Imai, T. 2009. Autoimmunity: Ann N.Y. Acad. Sci. 1173:350-356.], type 1 diabetes [Shimida, A; Oikawa, Y; Yamada, Y; Okubo, Y; and Narumi, S. 2009. Review of Diabetic Studies, 6(2): 81-84], myasthenia gravis (MG) [Pease, J. E. and Horuk, R. 2009. Expert Opin Ther Patents, 19 (2): 199-221], multiple sclerosis (MS) and other neuroinflammatory diseases [Muller, M; Carter, M. J.; Hofert, J; and Campbell, I. L. 2010. Neuropathology and Applied Neurobiology, 36:368-387.], lupus [Lacotte, S; Brun, S; Muller, S; and Dumortier, H. 2009. Autoimmunity: Ann N.Y. Acad. Sci. 1173:310-317.], rheumatoid arthritis (RA) [Brightling, C; Ammit, A. J.; Kaur, D; Black, J. L.; Wardlaw, A. J.; Hughes, J. M.; and Bradding, P. 2005. Am J Respir Crit Care Med. 171: 1103-1108.], lichen planus [Meller, S; Gillier, M; and Homey, B. 2009. J. Investigative Dermatology. 129: 315-319.].

Targeting CXCR3 appears a more straightforward way to treat the condition as this abrogates the effects of all three endogenous CXCR3 chemokines at the same time.

Assorted patent applications and granted patents disclose inhibitors of chemokines or CXCR3 receptor, such as WO2003087063, WO200604924, WO2009094168 and WO2009105435 but the known compounds are structurally very different from the compounds according to the present invention.

We aimed to prepare new CXCR3 receptor antagonist compounds, which have strong antagonistic effect and are selective to the CXCR3 receptor. We also aimed that the stability, bioavailability, metabolism, therapeutic index, toxicity and solubility of the new compounds allow their development into a drug substance. A further aim was that the compounds, due to their favorable enteric absorption, can be administered orally.

Thus, the inventors of the present invention have identified compounds represented by the following formula 1 possessing inhibitory activity against CXCR3 receptors.

The present invention thus provides a compound of formula 1

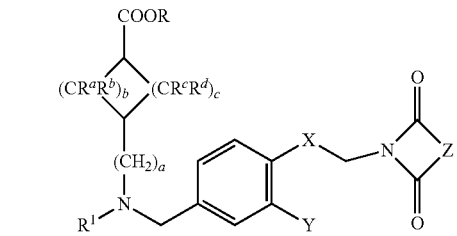

wherein
R represents hydrogen or $C_{1-4}$ alkyl group;
$R^1$ represents a group selected from the group consisting of

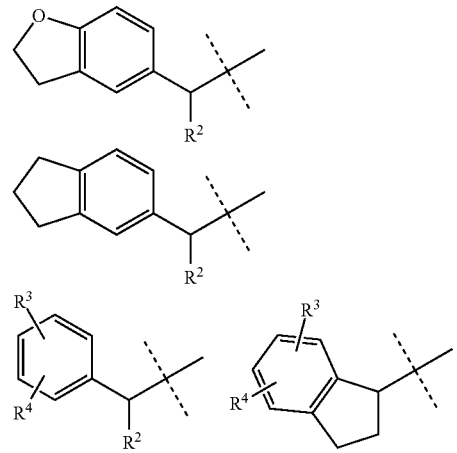

wherein
$R^2$ represents hydrogen or $C_{1-4}$ alkyl group;
$R^3$ represents hydrogen, halogen, $CF_3$, CN or $C_{1-4}$ alkyl; and
$R^4$ represents hydrogen, halogen or $C_{1-4}$ alkyl-;

a=0, 1 or 2; b=0, 1, 2 or 3, c=1, 2 or 3, and
$R^a$, $R^b$, $R^c$ and $R^d$ represent independently from each other H or $C_{1-4}$ alkyl;
X represents a $C_2$ aliphatic hydrocarbon bridge optionally containing a double bond or a triple bond or a heteroatom selected from O and S, or —CH(CH$_2$)CH—;
Y represents hydrogen, halogen, $C_{1-4}$ alkyl, $C_{1-4}$ alkoxy or $C_{1-4}$ hydroxyalkyl; and
Z represents a $C_{1-4}$ aliphatic hydrocarbon bridge optionally containing one double bond, and/or one or more heteroatom selected from O, S, NH and N(CH$_3$) or represents a $C_{2-4}$ aliphatic hydrocarbon bridge fused with a $C_{3-6}$ cycloalkyl ring optionally containing one or more double bond or with a phenyl ring or represents a $C_{1-4}$ aliphatic hydrocarbon bridge substituted with a spiro $C_{3-6}$ cycloalkyl ring optionally containing one or more double bond;
or a pharmaceutically acceptable salt or stereoisomer thereof or a pharmaceutically acceptable salt of the stereoisomer.

According to another aspect of the present invention, there is provided a process for the preparation of a compound of formula 1 or a pharmaceutically acceptable salt, stereoisomer or a pharmaceutically acceptable salt of the stereoisomer, comprising the steps of reductive amination of a benzaldehyde of formula 4

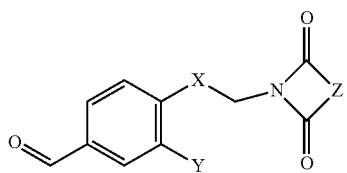

4 wherein X, Y and Z have the meaning as defined above—with a primary amine of formula 5

5 wherein $R^1$ has the meaning as defined above—
reacting the obtained secondary amine of formula 2

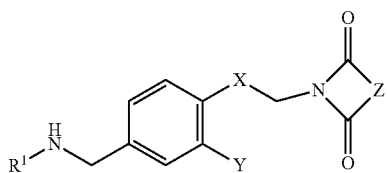

2 with a formyl- or oxocycloalkane carboxylic acid ester of formula 3

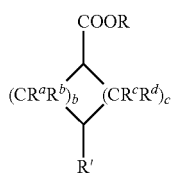

3 wherein R, $R^a$, $R^b$, $R^c$, $R^d$, b, and c have the meaning as defined above and R' represents —CHO or =O—
and optionally hydrolyzing the obtained ester of formula 1.

According to another aspect of the present invention there is provided a pharmaceutical composition containing at least one compound of formula 1 or a pharmaceutically acceptable salt, stereoisomer or a pharmaceutically acceptable salt of the stereoisomer and at least one pharmaceutically acceptable excipient.

According to a further aspect the present invention is directed to the compounds of formula 1 or a pharmaceutically acceptable salt, stereoisomer or a pharmaceutically acceptable salt of the stereoisomer for use in the preventive and/or therapeutic treatment of a CXCR3 receptor mediated disease or disorder, especially of a disease or disorder selected from the group consisting of COPD, psoriasis, graft/transplant rejection, ophthalmological disease, celiac disease, inflammatory bowel disease (IBD), type 1 diabetes, myasthenia gravis (MG), multiple sclerosis (MS) and other neuroinflammatory diseases, lupus, rheumatoid arthritis (RA) or lichen planus.

In addition the present invention is directed to a method of treating a CXCR3 receptor mediated disease or disorder, especially of a disease or disorder selected from the group consisting of COPD, psoriasis, graft/transplant rejection, ophthalmological disease, celiac disease, inflammatory bowel disease (IBD), type 1 diabetes, myasthenia gravis (MG), multiple sclerosis (MS) and other neuroinflammatory diseases, lupus, rheumatoid arthritis (RA) or lichen planus comprising administering an effective amount of a compound of formula 1 or a pharmaceutically acceptable salt or stereoisomer thereof or a pharmaceutically acceptable salt of the stereoisomer to a patient in need thereof.

As used above and throughout the description of the invention, the following terms, unless otherwise indicated, are to be understood to have the following meanings:

The $C_{1-4}$ alkyl group represents a straight or branched alkyl group having 1 to 4 carbon atoms, for example, methyl group, ethyl group, n-propyl group, isopropyl group, n-butyl group, isobutyl group, sec-butyl group, tert-butyl group, and the like.

The $C_{1-4}$ alkoxy group represents an above identified alkyl group having 1 to 4 carbon atoms and attached through an oxygen atom, for example, methoxy group, ethoxy group, propoxy group, isopropoxy group, butoxy group, isobutoxy group, sec-butoxy group, tert-butoxy group, and the like.

The $C_{1-4}$ hydroxyalkyl group represents an above identified alkyl group having 1 to 4 carbon atoms and bearing one or more hydroxy group, for example, hydroxymethyl group, 1-hydroxy-ethyl group, 2-hydroxy-ethyl group, 1-, 2- or 3-hydroxy-n-propyl group, 1- or 2-hydroxy-isopropyl group, and the like.

The halogen atom represents a fluorine, chlorine, bromine or iodine atom.

The $C_2$ aliphatic hydrocarbon bridge optionally containing a double or a triple bond or a heteroatom selected from O and S means an alkandiyl group having 2 carbon atoms and optionally containing a double or a triple bond or a heteroatom selected from O and S, for example, —CH$_2$—CH$_2$—, —CH=CH—, —C≡C—, —O—CH$_2$—, —S—CH$_2$—, and the like.

The $C_{1-4}$ aliphatic hydrocarbon bridge optionally containing one double bond and/or one or more heteroatom selected from O, S, NH and N(CH$_3$) means an alkandiyl group having 1 to 4 carbon atoms and optionally containing one double bond and/or one or more heteroatom selected from O, S, NH and N(CH$_3$), for example —CH$_2$—CH$_2$—, —CH$_2$—O—, —CH$_2$—S—, —CH$_2$—NH—, —CH$_2$—N(CH$_3$)—, —CH$_2$—CH$_2$—CH$_2$—, —CH=CH—N(CH$_3$)—, —N=CH—N(CH$_3$)—, and the like.

The C$_{2-4}$ aliphatic hydrocarbon bridge fused with a C$_{3-6}$ cycloalkyl ring optionally containing one or more double bond or with a phenyl ring means an alkandiyl group having 2 to 4 carbon atoms and fused with a cycloalkyl ring having 3 to 6 carbon atoms and optionally containing one or more double bond or with a phenyl ring for example cyclopropandiyl,

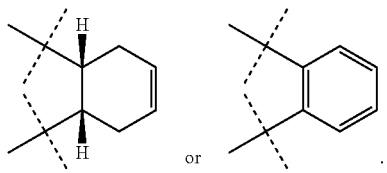

The C$_{1-4}$ aliphatic hydrocarbon bridge substituted with a spiro C$_{3-6}$ cycloalkyl ring optionally containing one or more double bond means an alkandiyl group having 1 to 4 carbon atoms and substituted with a spiro cycloalkyl ring having 3 to 6 carbon atoms and optionally containing one or more double bond, means for example

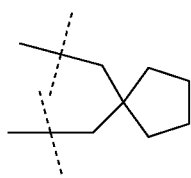

In the formulae the bond crossed by dotted line

represents the attachment of the substituent with the other parts of the compound.

By salts of the compounds of the formula 1 we mean salts formed with inorganic and organic acids. Preferred salts are those given with pharmaceutically acceptable acids as for instance hydrochloric acid, and the like. The salts formed during purification or isolation are also subject of the invention.

The compounds represented by the aforementioned formula 1 may have one or more asymmetric carbon atoms. Thus, they can exist in the form of optical isomers, enantiomers or diastereoisomers.

The compounds of formula 1 can also exist in the form of cis (Z) or trans (E) stereoisomers. These stereoisomers, enantiomers and diastereoisomers as well as their mixtures, including the racemates, are also subject of the invention.

One of the embodiments of the present invention includes compounds of formula 1 wherein R represents hydrogen or C$_{1-4}$ alkyl;

R$^1$ represents a group selected from the group consisting of

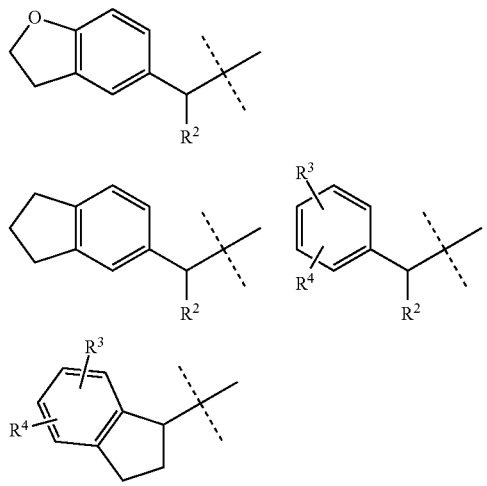

wherein

R$^2$ represents hydrogen or C$_{1-4}$ alkyl;

R$^3$ represents hydrogen, halogen, CF$_3$, CN or C$_{1-4}$ alkyl; and

R$^4$ represents hydrogen, halogen or C$_{1-4}$ alkyl;

a=0 or 1; b=0, 1 or 2, c=1, 2 or 3; and

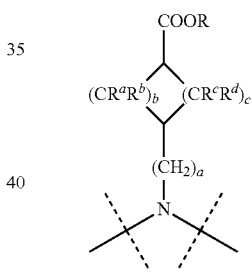

represents a cycloalkane carboxylic acid or ester thereof, selected from the group consisting of

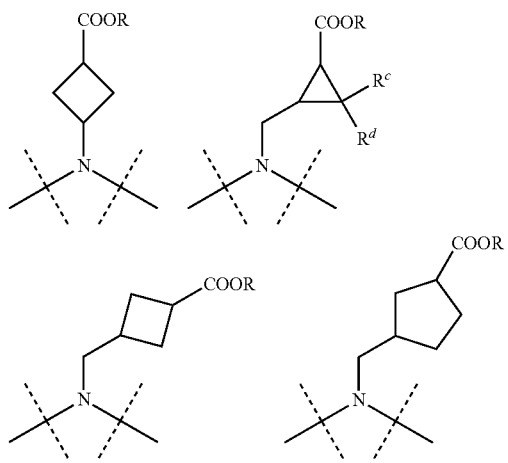

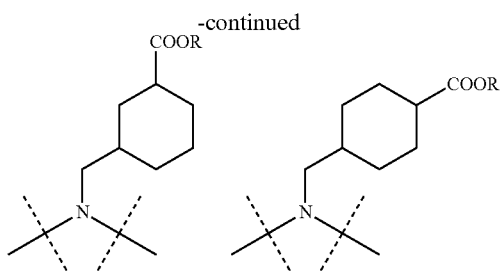

wherein
$R^c$ and $R^d$ represent independently from each other H or $C_{1-4}$ alkyl;

X represents —O—$CH_2$—, —S—$CH_2$—, —CH=CH—, —$CH_2$—$CH_2$—, —C≡C— or cyclopropandiyl;

Y represents hydrogen, halogen; $C_{1-4}$ alkyl, $C_{1-4}$ alkoxy or $C_{1-4}$ hydroxyalkyl;

Z represents a $C_{1-4}$ aliphatic hydrocarbon bridge optionally containing one double bond, and/or one or more heteroatom selected from O, S, N and N($CH_3$) or represents a $C_{2-4}$ aliphatic hydrocarbon bridge fused with a $C_{3-6}$ cycloalkyl ring optionally containing one or more double bond or with a phenyl ring or represents a $C_{1-4}$ aliphatic hydrocarbon bridge substituted with a spiro $C_{3-6}$ cycloalkyl ring optionally containing one or more double bond or a pharmaceutically acceptable salt or stereoisomer thereof or a pharmaceutically acceptable salt of the stereoisomer.

Another embodiment of the present invention includes compounds of formula 1 wherein R represents hydrogen, or a pharmaceutically acceptable salt or stereoisomer thereof or a pharmaceutically acceptable salt of the stereoisomer.

Another embodiment of the present invention includes compounds of formula 1 wherein $R^1$ represents a group selected from the group consisting of

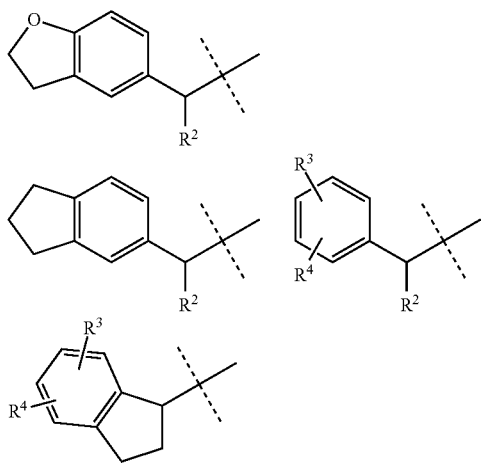

wherein
$R^2$ represents methyl or ethyl;
$R^3$ represents Cl, F, $CF_3$, CN, methyl or ethyl; and
$R^4$ represents hydrogen, Cl, F or methyl;

or a pharmaceutically acceptable salt or stereoisomer thereof or a pharmaceutically acceptable salt of the stereoisomer.

Another embodiment of the present invention includes compounds of formula 1 wherein $R^1$ represents a group selected from the group consisting of

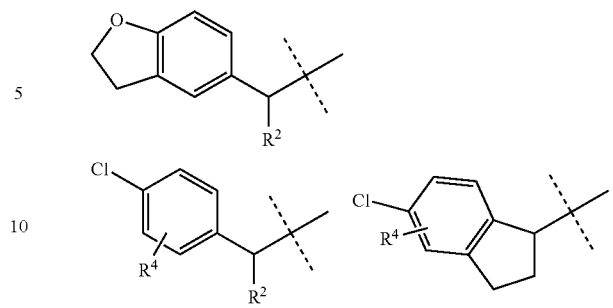

wherein
$R^2$ represents methyl or ethyl; and
$R^4$ represents hydrogen, Cl or F;

or a pharmaceutically acceptable salt or stereoisomer thereof or a pharmaceutically acceptable salt of the stereoisomer.

Another embodiment of the present invention includes compounds of formula 1 wherein $R^1$ represents a group selected from the group consisting of

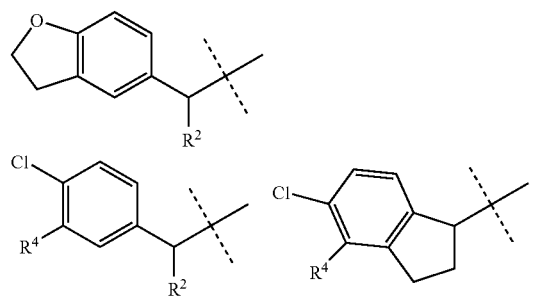

wherein
$R^2$ represents methyl or ethyl; and
$R^4$ represents hydrogen, Cl or F;

or a pharmaceutically acceptable salt or stereoisomer thereof or a pharmaceutically acceptable salt of the stereoisomer.

Another embodiment of the present invention includes compounds of formula 1 wherein X represents —O—$CH_2$—, —S—$CH_2$— or —$CH_2$—$CH_2$—, or a pharmaceutically acceptable salt or stereoisomer thereof or a pharmaceutically acceptable salt of the stereoisomer.

Another embodiment of the present invention includes compounds of formula 1 wherein Y represents hydrogen, Cl, F, methyl, ethyl, methoxy or —$CH_2$—OH; or a pharmaceutically acceptable salt or stereoisomer thereof or a pharmaceutically acceptable salt of the stereoisomer.

Another embodiment of the present invention includes compounds of formula 1 wherein Y represents ethyl or methoxy; or a pharmaceutically acceptable salt or stereoisomer thereof or a pharmaceutically acceptable salt of the stereoisomer.

Another embodiment of the present invention includes compounds of formula 1 wherein Z represents —$(CH_2)_2$—, —$(CH_2)_3$—, —$CH_2$—O—, —$CH_2$—S—, —$CH_2$—N($CH_3$)—, —CH=CH—N($CH_3$)—, —N=CH—N($CH_3$)—, cyclopropandiyl, -,

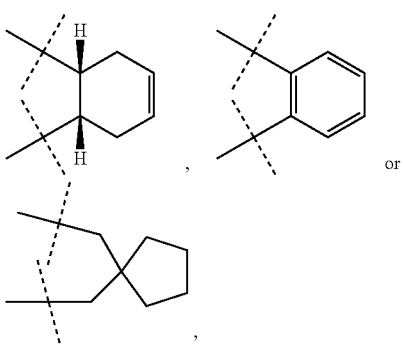

or a pharmaceutically acceptable salt or stereoisomer thereof or a pharmaceutically acceptable salt of the stereoisomer.

Another embodiment of the present invention includes compounds of formula 1 wherein Z represents —($CH_2$)$_2$— or —$CH_2$—N($CH_3$)—; or a pharmaceutically acceptable salt or stereoisomer thereof or a pharmaceutically acceptable salt of the stereoisomer.

Another embodiment of the present invention includes compounds of formula 1 wherein
R represents hydrogen, methyl or ethyl;
$R^1$ represents a group selected from the group consisting of

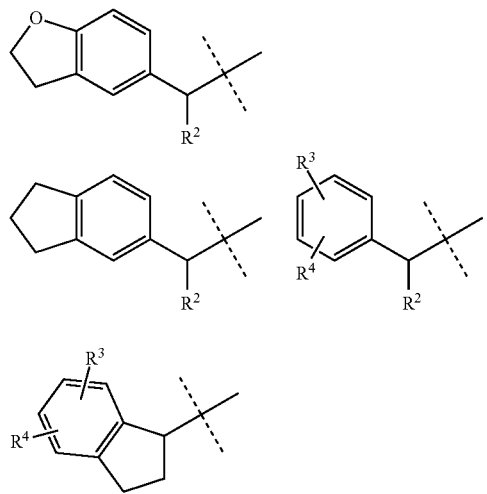

wherein
$R^2$ represents hydrogen methyl or ethyl;
$R^3$ represents hydrogen, chloro, fluoro, $CF_3$, CN, methyl or ethyl; and
$R^4$ represents hydrogen, chloro, fluoro, methyl or ethyl;
a=0 or 1; b=0, 1 or 2, c=1, 2 or 3; and

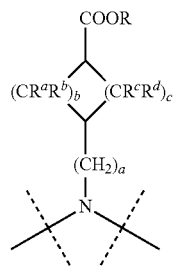

represents a cycloalkane carboxylic acid or ester thereof, selected from the group consisting of

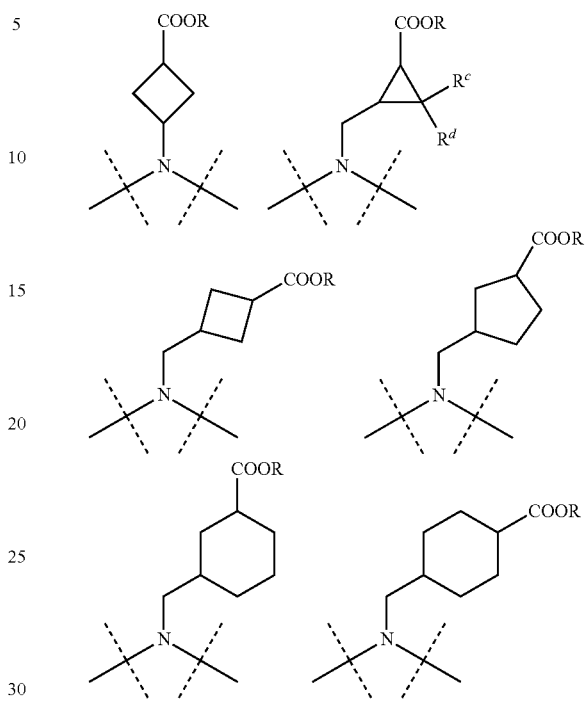

wherein
$R^c$ and $R^d$ represent independently from each other H or methyl or ethyl;
X represents —O—$CH_2$—, —S—$CH_2$—, —CH=CH—, —$CH_2$—$CH_2$—, —C≡C— or cyclopropandiyl;
Y represents chloro, fluoro, methyl, ethyl, methoxy or —$CH_2$—OH;
Z represents —($CH_2$)$_2$—, —($CH_2$)$_3$—, —$CH_2$—O—, —$CH_2$—S—, —$CH_2$—N($CH_3$)—, —CH=CH—N($CH_3$)—, —N=CH—N($CH_3$)—, CH($CH_2$)CH—, -,

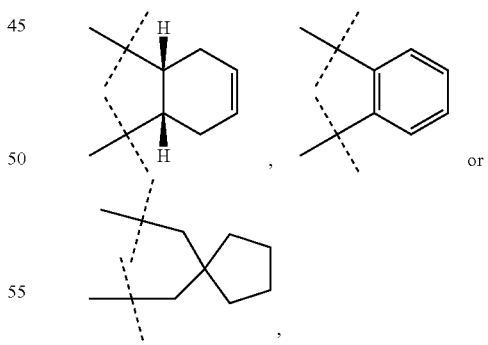

or a pharmaceutically acceptable salt or stereoisomer thereof or a pharmaceutically acceptable salt of the stereoisomer.

Particularly compounds of the present invention represented by formula 1 include compounds selected from the group consisting of:
1. trans-4-[([1-(2,3-Dihydro-1-benzofuran-5-yl)ethyl]{4-[2-(2,5-dioxo-pyrrolidin-1-yl)ethoxy]-3-methoxybenzyl}amino)methyl]-cyclohexanecarboxylic acid 1.1 trans-4-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid ethyl ester
2. cis-4-[([1-(2,3-Dihydro-1-benzofuran-5-yl)ethyl]{4-[2-(2,5-dioxo-pyrrolidin-1-yl)ethoxy]-3-methoxybenzyl}amino)methyl]-cyclohexanecarboxylic acid
3. trans-4-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid
4. trans-4-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid
5. trans-4-[([(S)-1-(4-Chloro-phenyl)-ethyl]-{4-[2-(2,5-dioxo-pyrrolidin-1-yl)-ethoxy]-3-methoxy-benzyl}-amino)-methyl]cyclohexanecarboxylic acid
6. trans-4-[([(R)-1-(4-Chloro-phenyl)-ethyl]-{4-[2-(2,5-dioxo-pyrrolidin-1-yl)-ethoxy]-3-methoxy-benzyl}-amino)-methyl]-cyclohexanecarboxylic acid
7. trans-4-[([(S)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid
8. cis-4-[([(S)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid
9. trans-4-[([(R)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid
10. trans-4-[((5-Chloro-indan-1-yl)-{4-[2-(2,5-dioxo-pyrrolidin-1-yl)-ethoxy]-3-methoxy-benzyl}-amino)-methyl]-cyclohexanecarboxylic acid
11. trans-4-[(((R)-5-Chloro-indan-1-yl)-{4-[2-(2,5-dioxo-pyrrolidin-1-yl)-ethoxy]-3-methoxy-benzyl}-amino)-methyl]-cyclohexanecarboxylic acid
12. trans-4-[(((S)-5-Chloro-indan-1-yl)-{4-[2-(2,5-dioxo-pyrrolidin-1-yl)-ethoxy]-3-methoxy-benzyl}-amino)-methyl]-cyclohexanecarboxylic acid
13. cis-4-[((5-Chloro-indan-1-yl)-{4-[2-(2,5-dioxo-pyrrolidin-1-yl)-ethoxy]-3-methoxy-benzyl}-amino)-methyl]-cyclohexanecarboxylic acid
14. trans-4-[(((S)-4,5-Dichloro-indan-1-yl)-{4-[2-(2,5-dioxo-pyrrolidin-1-yl)-ethoxy]-3-methoxy-benzyl}-amino)-methyl]-cyclohexanecarboxylic acid hydrochloride
15. trans-4-[([1-(2,3-Dihydro-benzofuran-5-yl)-ethyl]-{4-[2-(2,4-dioxo-thiazolidin-3-yl)-ethoxy]-3-methoxy-benzyl}-amino)-methyl]-cyclohexanecarboxylic acid
16. trans-4-({{3-Chloro-4-[2-(2,5-dioxo-pyrrolidin-1-yl)-ethoxy]-benzyl}-[1-(2,3-dihydro-benzofuran-5-yl)-ethyl]-amino}-methyl)-cyclohexanecarboxylic acid
17. trans-4-[([1-(2,3-Dihydro-benzofuran-5-yl)-ethyl]-{4-[2-(2,5-dioxo-pyrrolidin-1-yl)-ethoxy]-3-methyl-benzyl}-amino)-methyl]-cyclohexanecarboxylic acid
18. trans-4-[([1-(2,3-Dihydro-benzofuran-5-yl)-propyl]-{4-[2-(2,5-dioxo-pyrrolidin-1-yl)-ethoxy]-3-methoxy-benzyl}-amino)-methyl]-cyclohexanecarboxylic acid
19. trans-4-[([1-(2,3-Dihydro-benzofuran-5-yl)-ethyl]-{4-[2-(2,4-dioxo-oxazolidin-3-yl)-ethoxy]-3-methoxy-benzyl}-amino)-methyl]-cyclohexanecarboxylic acid
20. trans-4-[((5-Chloro-indan-1-yl)-{3-chloro-4-[2-(3-methyl-2,5-dioxo-imidazolidin-1-yl)-ethoxy]-benzyl}-amino)-methyl]-cyclohexanecarboxylic acid
21. trans-4-{[{3-Chloro-4-[2-(2,5-dioxo-pyrrolidin-1-yl)-ethoxy]-benzyl}-(5-chloro-indan-1-yl)-amino]-methyl}-cyclohexanecarboxylic acid
22. trans-4-({{3-Chloro-4-[2-(3-methyl-2,5-dioxo-imidazolidin-1-yl)-ethoxy]-benzyl}-[1-(2,3-dihydro-benzofuran-5-yl)-ethyl]-amino}-methyl)-cyclohexanecarboxylic acid
23. trans-4-({{3-Chloro-4-[2-(3-methyl-2,5-dioxo-imidazolidin-1-yl)-ethoxy]-benzyl}-[(S)-1-(4-chloro-phenyl)-ethyl]-amino}-methyl)-cyclohexanecarboxylic acid
24. trans-4-[((5-Chloro-indan-1-yl)-{4-[2-(2,4-dioxo-thiazolidin-3-yl)-ethoxy]-3-methoxy-benzyl}-amino)-methyl]-cyclohexanecarboxylic acid
25. trans-4-[([1-(4-Chloro-3-methyl-phenyl)-ethyl]-{4-[2-(2,5-dioxo-pyrrolidin-1-yl)-ethoxy]-3-methoxy-benzyl}-amino)-methyl]-cyclohexanecarboxylic acid
26. trans-4-[([(S)-1-(4-Chloro-3-methyl-phenyl)-ethyl]-{4-[2-(2,5-dioxo-pyrrolidin-1-yl)-ethoxy]-3-methoxy-benzyl}-amino)-methyl]-cyclohexanecarboxylic acid
27. trans-4-[([(R)-1-(4-Chloro-3-methyl-phenyl)-ethyl]-{4-[2-(2,5-dioxo-pyrrolidin-1-yl)-ethoxy]-3-methoxy-benzyl}-amino)-methyl]-cyclohexanecarboxylic acid
28. trans-4-[([1-(2,3-Dihydro-benzofuran-5-yl)-propyl]-{3-methoxy-4-[2-(3-methyl-2,5-dioxo-imidazolidin-1-yl)-ethoxy]-benzyl}-amino)-methyl]-cyclohexanecarboxylic acid
29. trans-4-[((5-Chloro-indan-1-yl)-{4-[2-(2,5-dioxo-pyrrolidin-1-yl)-ethoxy]-3-methyl-benzyl}-amino)-methyl]-cyclohexanecarboxylic acid
30. trans-4-[(((S)-5-Chloro-indan-1-yl)-{4-[2-(2,5-dioxo-pyrrolidin-1-yl)-ethoxy]-3-methyl-benzyl}-amino)-methyl]-cyclohexanecarboxylic acid
31. trans-4-[(((R)-5-Chloro-indan-1-yl)-{4-[2-(2,5-dioxo-pyrrolidin-1-yl)-ethoxy]-3-methyl-benzyl}-amino)-methyl]-cyclohexanecarboxylic acid
32. trans-4-({{3-Chloro-4-[2-(2,5-dioxo-pyrrolidin-1-yl)-ethoxy]-benzyl}-[(S)-1-(4-chloro-phenyl)-ethyl]-amino}-methyl)-cyclohexanecarboxylic acid
33. trans-4-[([1-(2,3-Dihydro-benzofuran-5-yl)-ethyl]-{4-[2-(2,4-dioxo-thiazolidin-3-yl)-ethoxy]-3-methyl-benzyl}-amino)-methyl]-cyclohexanecarboxylic acid
34. trans-4-[([(S)-1-(4-Chloro-phenyl)-ethyl]-{4-[2-(2,4-dioxo-thiazolidin-3-yl)-ethoxy]-3-methoxy-benzyl}-amino)-methyl]-cyclohexanecarboxylic acid
35. trans-4-[([1-(2,3-Dihydro-benzofuran-5-yl)-ethyl]-{4-[(E)-3-(2,5-dioxo-pyrrolidin-1-yl)-propenyl]-3-methoxy-benzyl}-amino)-methyl]-cyclohexanecarboxylic acid
36. trans-4-[([(S)-1-(4-Chloro-phenyl)-ethyl]-{4-[2-(2,4-dioxo-oxazolidin-3-yl)-ethoxy]-3-methoxy-benzyl}-amino)-methyl]-cyclohexanecarboxylic acid
37. trans-4-[([(S)-1-(4-Chloro-phenyl)-ethyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid
38. trans-4-[([1-(2,3-Dihydro-benzofuran-5-yl)-ethyl]-{4-[2-(2,6-dioxo-piperidin-1-yl)-ethoxy]-3-methoxy-benzyl}-amino)-methyl]-cyclohexanecarboxylic acid
39. trans-4-[([(S)-1-(4-Chloro-phenyl)-ethyl]-{3-methyl-4-[2-(3-methyl-2,5-dioxo-imidazolidin-1-yl)-ethoxy]-benzyl}-amino)-methyl]-cyclohexanecarboxylic acid
40. trans-4-[([1-(2,3-Dihydro-benzofuran-5-yl)-ethyl]-{4-[3-(2,5-dioxo-pyrrolidin-1-yl)-propyl]-3-methoxy-benzyl}-amino)-methyl]-cyclohexanecarboxylic acid
41. 3-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid
42. trans-4-[((5-Chloro-6-methyl-indan-1-yl)-{4-[2-(2,5-dioxo-pyrrolidin-1-yl)-ethoxy]-3-methoxy-benzyl}-amino)-methyl]-cyclohexanecarboxylic acid 43. trans-4-[((5-Chloro-4-methyl-indan-1-yl)-{4-[2-(2,5-dioxo-pyrrolidin-1-yl)-ethoxy]-3-methoxy-benzyl}-amino)-methyl]-cyclohexanecarboxylic acid
44. trans-4-[((5-Chloro-indan-1-yl)-{4-[3-(2,5-dioxo-pyrrolidin-1-yl)-propyl]-3-methoxy-benzyl}-amino)-methyl]-cyclohexanecarboxylic acid
45. trans-4-[(((R)-5-Chloro-indan-1-yl)-{4-[3-(2,5-dioxo-pyrrolidin-1-yl)-propyl]-3-methoxy-benzyl}-amino)-methyl]-cyclohexanecarboxylic acid
46. trans-4-[(((S)-5-Chloro-indan-1-yl)-{4-[3-(2,5-dioxo-pyrrolidin-1-yl)-propyl]-3-methoxy-benzyl}-amino)-methyl]-cyclohexanecarboxylic acid
47. trans-4-({{3-Chloro-4-[3-(2,5-dioxo-pyrrolidin-1-yl)-propyl]-benzyl}-[1-(2,3-dihydro-benzofuran-5-yl)-ethyl]-amino}-methyl)-cyclohexanecarboxylic acid
48. trans-4-[((5-Chloro-indan-1-yl)-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid
49. trans-4-[([1-(2,3-Dihydro-benzofuran-5-yl)-ethyl]-{4-[2-(2,5-dioxo-pyrrolidin-1-ylmethyl)-cyclopropyl]-3-methoxy-benzyl}-amino)-methyl]-cyclohexanecarboxylic acid
50. trans-4-[((5-Chloro-indan-1-yl)-{3-methoxy-4-[3-(3-methyl-2,5-dioxo-imidazolidin-1-yl)-propyl]-benzyl}-amino)-methyl]-cyclohexanecarboxylic acid
51. trans-4-[([(S)-1-(4-Chloro-phenyl)-ethyl]-{3-methoxy-4-[3-(3-methyl-2,5-dioxo-imidazolidin-1-yl)-propyl]-benzyl}-amino)-methyl]-cyclohexanecarboxylic acid
52. trans-4-[((5-Chloro-indan-1-yl)-{3-methoxy-4-[2-(3-methyl-2,5-dioxo-imidazolidin-1-yl)-ethoxy]-benzyl}-amino)-methyl]-cyclohexanecarboxylic acid
53. trans-4-[([(S)-1-(4-Chloro-phenyl)-ethyl]-{3-methoxy-4-[2-(3-methyl-2,5-dioxo-imidazolidin-1-yl)-ethoxy]-benzyl}-amino)-methyl]-cyclohexanecarboxylic acid
54. trans-4-[([(S)-1-(4-Chloro-phenyl)-ethyl]-{4-[3-(2,5-dioxo-pyrrolidin-1-yl)-propyl]-3-methyl-benzyl}-amino)-methyl]-cyclohexanecarboxylic acid
55. trans-4-[([(S)-1-(4-Chloro-phenyl)-ethyl]-{4-[3-(2,5-dioxo-pyrrolidin-1-yl)-prop-1-ynyl]-3-methoxy-benzyl}-amino)-methyl]-cyclohexanecarboxylic acid
56. trans-4-[([(S)-1-(4-Chloro-phenyl)-ethyl]-{4-[3-(2,5-dioxo-pyrrolidin-1-yl)-propyl]-3-methoxy-benzyl}-amino)-methyl]-cyclohexanecarboxylic acid
57. trans-4-[((5-Chloro-indan-1-yl)-{3-methyl-4-[2-(3-methyl-2,5-dioxo-imidazolidin-1-yl)-ethoxy]-benzyl}-amino)-methyl]-cyclohexanecarboxylic acid
58. trans-4-[([(S)-1-(4-Chloro-phenyl)-ethyl]-{3-methyl-4-[2-(3-methyl-2,6-dioxo-3,6-dihydro-2H-pyrimidin-1-yl)-ethoxy]-benzyl}-amino)-methyl]-cyclohexanecarboxylic acid
59. trans-4-[([1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid
60. trans-4-[([1-(2,3-Dihydro-benzofuran-5-yl)-ethyl]-{3-methyl-4-[2-(3-methyl-2,6-dioxo-3,6-dihydro-2H-pyrimidin-1-yl)-ethoxy]-benzyl}-amino)-methyl]-cyclohexanecarboxylic acid
61. trans-4-[([1-(4-Cyano-phenyl)-ethyl]-{4-[2-(2,5-dioxo-pyrrolidin-1-yl)-ethoxy]-3-methyl-benzyl}-amino)-methyl]-cyclohexanecarboxylic acid
62. trans-4-[([1-(4-Cyano-phenyl)-ethyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid
63. trans-4-[([1-(4-Chloro-phenyl)-propyl]-{4-[2-(2,5-dioxo-pyrrolidin-1-yl)-ethoxy]-3-methoxy-benzyl}-amino)-methyl]-cyclohexanecarboxylic acid
64. trans-4-[([1-(4-Chloro-phenyl)-propyl]-{3-methyl-4-[2-(3-methyl-2,6-dioxo-3,6-dihydro-2H-pyrimidin-1-yl)-ethoxy]-benzyl}-amino)-methyl]-cyclohexanecarboxylic acid
65. trans-4-[([1-(4-Chloro-phenyl)-propyl]-{4-[2-(2,5-dioxo-pyrrolidin-1-yl)-ethoxy]-3-methyl-benzyl}-amino)-methyl]-cyclohexanecarboxylic acid
66. trans-4-[([1-(2,3-Dihydro-benzofuran-5-yl)-propyl]-{4-[3-(2,5-dioxo-pyrrolidin-1-yl)-propyl]-3-methoxy-benzyl}-amino)-methyl]-cyclohexanecarboxylic acid
67. trans-4-[([1-(4-Chloro-phenyl)-propyl]-{3-methoxy-4-[2-(3-methyl-2,5-dioxo-imidazolidin-1-yl)-ethoxy]-benzyl}-amino)-methyl]-cyclohexanecarboxylic acid
68. trans-4-[([1-(4-Chloro-phenyl)-propyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid
69. trans-4-[([1-(2,3-Dihydro-benzofuran-5-yl)-propyl]-{4-[2-(2,5-dioxo-pyrrolidin-1-yl)-ethoxy]-3-methyl-benzyl}-amino)-methyl]-cyclohexanecarboxylic acid
70. trans-4-[([1-(4-Chloro-phenyl)-propyl]-{3-methyl-4-[2-(3-methyl-2,5-dioxo-imidazolidin-1-yl)-ethoxy]-benzyl}-amino)-methyl]-cyclohexanecarboxylic acid
71. trans-4-[(((S)-5-Chloro-indan-1-yl)-{4-[2-(2,5-dioxo-pyrrolidin-1-yl)-ethoxy]-3-ethyl-benzyl}-amino)-methyl]-cyclohexanecarboxylic acid
72. trans-4-[(((S)-5-Chloro-indan-1-yl)-{4-[2-(2,5-dioxo-pyrrolidin-1-yl)-ethoxy]-3-fluoro-benzyl}-amino)-methyl]-cyclohexanecarboxylic acid
73. trans-4-[([(S)-1-(4-Chloro-phenyl)-ethyl]-{4-[2-(2,5-dioxo-pyrrolidin-1-yl)-ethoxy]-3-fluoro-benzyl}-amino)-methyl]-cyclohexanecarboxylic acid
74. trans-4-[(((S)-5,6-Dichloro-indan-1-yl)-{4-[2-(2,5-dioxo-pyrrolidin-1-yl)-ethoxy]-3-methoxy-benzyl}-amino)-methyl]-cyclohexanecarboxylic acid
75. trans-4-[([(S)-1-(4-Chloro-phenyl)-ethyl]-{4-[2-(2,5-dioxo-pyrrolidin-1-yl)-ethoxy]-3-ethyl-benzyl}-amino)-methyl]-cyclohexanecarboxylic acid
76. trans-4-[([1-(2,3-Dihydro-benzofuran-5-yl)-ethyl]-{4-[2-(2,5-dioxo-pyrrolidin-1-yl)-ethoxy]-3-ethyl-benzyl}-amino)-methyl]-cyclohexanecarboxylic acid
77. trans-4-[([1-(3,4-Dichloro-phenyl)-ethyl]-{4-[2-(2,5-dioxo-pyrrolidin-1-yl)-ethoxy]-3-methoxy-benzyl}-amino)-methyl]-cyclohexanecarboxylic acid
78. trans-4-[([1-(3,4-Dichloro-phenyl)-ethyl]-{4-[2-(2,5-dioxo-pyrrolidin-1-yl)-ethoxy]-3-methyl-benzyl}-amino)-methyl]-cyclohexanecarboxylic acid
79. trans-4-[([(S)-1-(4-Chloro-phenyl)-ethyl]-{4-[2-(2,5-dioxo-pyrrolidin-1-yl)-ethoxy]-benzyl}-amino)-methyl]-cyclohexanecarboxylic acid
80. trans-4-[([1-(3,4-Dichloro-phenyl)-ethyl]-{3-methyl-4-[2-(3-methyl-2,5-dioxo-imidazolidin-1-yl)-ethoxy]-benzyl}-amino)-methyl]-cyclohexanecarboxylic acid
81. trans-4-({{4-[2-(2,5-Dioxo-pyrrolidin-1-yl)-ethoxy]-3-methoxy-benzyl}-[1-(4-ethyl-phenyl)-ethyl]-amino}-methyl)-cyclohexanecarboxylic acid
82. trans-4-[([1-(4-Chloro-3-fluoro-phenyl)-ethyl]-{4-[2-(2,5-dioxo-pyrrolidin-1-yl)-ethoxy]-3-methoxy-benzyl}-amino)-methyl]-cyclohexanecarboxylic acid
83. trans-4-{[{4-[2-(2,5-Dioxo-pyrrolidin-1-yl)-ethoxy]-3-methyl-benzyl}-(1-p-tolyl-ethyl)-amino]-methyl}-cyclohexanecarboxylic acid 84. trans-4-{[{4-[2-(2,5-Dioxo-pyrrolidin-1-yl)-ethoxy]-3-methoxy-benzyl}-(1-p-tolyl-ethyl)-amino]-methyl}-cyclohexanecarboxylic acid
85. trans-4-[([(S)-1-(4-Chloro-phenyl)-ethyl]-{4-[2-(2,5-dioxo-pyrrolidin-1-yl)-ethoxy]-3-hydroxymethyl-benzyl}-amino)-methyl]-cyclohexanecarboxylic acid
86. trans-4-[(((S)-4,5-Dichloro-indan-1-yl)-{4-[2-(2,5-dioxo-pyrrolidin-1-yl)-ethoxy]-3-ethyl-benzyl}-amino)-methyl]-cyclohexanecarboxylic acid
87. trans-4-[([(S)-1-(4-Chloro-phenyl)-ethyl]-{4-[2-(2,5-dioxo-pyrrolidin-1-yl)-ethylsulfanyl]-3-methoxy-benzyl}-amino)-methyl]-cyclohexanecarboxylic acid
88. trans-4-[(((S)-5-Chloro-indan-1-yl)-{4-[2-(2,5-dioxo-pyrrolidin-1-yl)-ethylsulfanyl]-3-methoxy-benzyl}-amino)-methyl]-cyclohexanecarboxylic acid
89. trans-4-[([1-(4-Chloro-3-fluoro-phenyl)-ethyl]-{4-[2-(2,5-dioxo-pyrrolidin-1-yl)-ethoxy]-3-ethyl-benzyl}-amino)-methyl]-cyclohexanecarboxylic acid
90. trans-4-[([(R)-1-(4-Chloro-3-fluoro-phenyl)-ethyl]-{4-[2-(2,5-dioxo-pyrrolidin-1-yl)-ethoxy]-3-ethyl-benzyl}-amino)-methyl]-cyclohexanecarboxylic acid
91. trans-4-[([(S)-1-(4-Chloro-3-fluoro-phenyl)-ethyl]-{4-[2-(2,5-dioxo-pyrrolidin-1-yl)-ethoxy]-3-ethyl-benzyl}-amino)-methyl]-cyclohexanecarboxylic acid
92. trans-4-[([1-(4-Chloro-3-fluoro-phenyl)-ethyl]-{4-[2-(2,5-dioxo-pyrrolidin-1-yl)-ethoxy]-3-fluoro-benzyl}-amino)-methyl]-cyclohexanecarboxylic acid
93. trans-4-[((4-Chloro-5-fluoro-indan-1-yl)-{4-[2-(2,5-dioxo-pyrrolidin-1-yl)-ethoxy]-3-methoxy-benzyl}-amino)-methyl]-cyclohexanecarboxylic acid
94. trans-4-[((6-Chloro-5-fluoro-indan-1-yl)-{4-[2-(2,5-dioxo-pyrrolidin-1-yl)-ethoxy]-3-methoxy-benzyl}-amino)-methyl]-cyclohexanecarboxylic acid
95. trans-4-[((6-Chloro-5-fluoro-indan-1-yl)-{4-[2-(2,5-dioxo-pyrrolidin-1-yl)-ethoxy]-3-ethyl-benzyl}-amino)-methyl]-cyclohexanecarboxylic acid
96. trans-4-[((4-Chloro-5-fluoro-indan-1-yl)-{4-[2-(2,5-dioxo-pyrrolidin-1-yl)-ethoxy]-3-ethyl-benzyl}-amino)-methyl]-cyclohexanecarboxylic acid
97. trans-4-[((6-Chloro-5-fluoro-indan-1-yl)-{4-[2-(2,5-dioxo-pyrrolidin-1-yl)-ethoxy]-3-fluoro-benzyl}-amino)-methyl]-cyclohexanecarboxylic acid
98. trans-4-[((5-Chloro-6-fluoro-indan-1-yl)-{4-[2-(2,5-dioxo-pyrrolidin-1-yl)-ethoxy]-3-methoxy-benzyl}-amino)-methyl]-cyclohexanecarboxylic acid
99. (1R,3R)-3-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclopentanecarboxylic acid
100. (1S,3S)-3-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclopentanecarboxylic acid
101. (1R,3S)-3-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclopentanecarboxylic acid
102. (1S,3R)-3-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclopentanecarboxylic acid
103. (1R,3S)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid
104. (1R,3R)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid
105. (1R,3R)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid
106. (1S,3R)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid
107. (1R,3S)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid
108. (1S,3R)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid
109. (1S,3S)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid
110. (1S,3S)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid
111. (1R,2R)-2-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopropanecarboxylic acid ethyl ester
112. (1R,2R)-2-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopropanecarboxylic acid
113. (1S,2R)-2-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopropanecarboxylic acid ethyl ester
114. (1S,2R)-2-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopropanecarboxylic acid
115. (1R,3R)-3-[([1-(4-Chloro-phenyl)-propyl]-{3-methyl-4-[2-(3-methyl-2,5-dioxo-imidazolidin-1-yl)-ethoxy]-benzyl}-amino)-methyl]-2,2-dimethyl-cyclopropanecarboxylic acid
116. (1S,3S)-3-[([1-(4-Chloro-phenyl)-propyl]-{3-methoxy-4-[2-(3-methyl-2,5-dioxo-imidazolidin-1-yl)-ethoxy]-benzyl}-amino)-methyl]-2,2-dimethyl-cyclopropanecarboxylic acid
117. (1S,3S)-3-[([1-(4-Chloro-phenyl)-propyl]-{4-[2-(2,5-dioxo-pyrrolidin-1-yl)-ethoxy]-3-methoxy-benzyl}-amino)-methyl]-2,2-dimethyl-cyclopropanecarboxylic acid
118. (1R,3R)-3-[([1-(4-Chloro-phenyl)-propyl]-{4-[2-(2,5-dioxo-pyrrolidin-1-yl)-ethoxy]-3-methyl-benzyl}-amino)-methyl]-2,2-dimethyl-cyclopropanecarboxylic acid
119. 1-[((5-Chloro-indan-1-yl)-{4-[2-(2,5-dioxo-pyrrolidin-1-yl)-ethoxy]-3-methoxy-benzyl}-amino)-methyl]-cyclopropanecarboxylic acid
120. trans-3-([1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid
121. cis-3-([1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid 122. cis-3-([(R)-1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid
123. cis-3-([(S)-1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid
124. trans-3-([1-(4-Chloro-3-fluoro-phenyl)-ethyl]-{4-[2-(2,5-dioxo-pyrrolidin-1-yl)-ethoxy]-3-methyl-benzyl}-amino)-cyclobutanecarboxylic acid
125. cis-3-([1-(4-Chloro-3-fluoro-phenyl)-ethyl]-{4-[2-(2,5-dioxo-pyrrolidin-1-yl)-ethoxy]-3-methyl-benzyl}-amino)-cyclobutanecarboxylic acid
126. 3-([1-(2,3-Dihydro-benzofuran-5-yl)-ethyl]-{4-[2-(2,5-dioxo-pyrrolidin-1-yl)-ethoxy]-3-methoxy-benzyl}-amino)-cyclobutanecarboxylic acid
127. 3-((5-Chloro-indan-1-yl)-{4-[2-(2,5-dioxo-pyrrolidin-1-yl)-ethoxy]-3-methoxy-benzyl}-amino)-cyclobutanecarboxylic acid
128. trans-3-([(R)-1-(4-Chloro-3-methyl-phenyl)-ethyl]-{4-[2-(2,5-dioxo-pyrrolidin-1-yl)-ethoxy]-3-methyl-benzyl}-amino)-cyclobutanecarboxylic acid
129. cis-3-([(R)-1-(4-Chloro-3-methyl-phenyl)-ethyl]-{4-[2-(2,5-dioxo-pyrrolidin-1-yl)-ethoxy]-3-methyl-benzyl}-amino)-cyclobutanecarboxylic acid
130. trans-34[(S)-1-(4-Chloro-3-methyl-phenyl)-ethyl]-{4-[2-(2,5-dioxo-pyrrolidin-1-yl)-ethoxy]-3-methyl-benzyl}-amino)-cyclobutanecarboxylic acid
131. cis-3-([(S)-1-(4-Chloro-3-methyl-phenyl)-ethyl]-{4-[2-(2,5-dioxo-pyrrolidin-1-yl)-ethoxy]-3-methyl-benzyl}-amino)-cyclobutanecarboxylic acid
132. cis-3-([(R)-1-(4-Chloro-phenyl)-ethyl]-{4-[2-(2,5-dioxo-pyrrolidin-1-yl)-ethoxy]-3-methyl-benzyl}-amino)-cyclobutanecarboxylic acid
133. cis-3-((5-Chloro-indan-1-yl)-{4-[2-(2,5-dioxo-pyrrolidin-1-yl)-ethoxy]-3-methyl-benzyl}-amino)-cyclobutanecarboxylic acid
134. cis-3-([1-(2,3-Dihydro-benzofuran-5-yl)-ethyl]-{3-methyl-4-[2-(3-methyl-2,6-dioxo-3,6-dihydro-2H-pyrimidin-1-yl)-ethoxy]-benzyl}-amino)-cyclobutanecarboxylic acid
135. cis-3-([1-(2,3-Dihydro-benzofuran-5-yl)-propyl]-{4-[2-(2,5-dioxo-pyrrolidin-1-yl)-ethoxy]-3-methyl-benzyl}-amino)-cyclobutanecarboxylic acid
136. cis-3-([(R)-1-(4-Chloro-phenyl)-ethyl]-{3-methyl-4-[2-(3-methyl-2,6-dioxo-3,6-dihydro-2H-pyrimidin-1-yl)-ethoxy]-benzyl}-amino)-cyclobutanecarboxylic acid
137. cis-3-([1-(3,4-Dichloro-phenyl)-ethyl]-{4-[2-(2,5-dioxo-pyrrolidin-1-yl)-ethoxy]-3-methoxy-benzyl}-amino)-cyclobutanecarboxylic acid
138. cis-3-([1-(3,4-Dichloro-phenyl)-ethyl]-{4-[2-(2,5-dioxo-pyrrolidin-1-yl)-ethoxy]-3-methyl-benzyl}-amino)-cyclobutanecarboxylic acid
139. cis-3-([1-(3,4-Dichloro-phenyl)-ethyl]-{4-[2-(2,5-dioxo-pyrrolidin-1-yl)-ethoxy]-3-ethyl-benzyl}-amino)-cyclobutanecarboxylic acid
140. cis-3-([1-(4-Chloro-3-fluoro-phenyl)-ethyl]-{4-[2-(2,5-dioxo-pyrrolidin-1-yl)-ethoxy]-3-ethyl-benzyl}-amino)-cyclobutanecarboxylic acid
141. cis-3-([1-(3,4-Dichloro-phenyl)-propyl]-{4-[2-(2,5-dioxo-pyrrolidin-1-yl)-ethoxy]-3-methoxy-benzyl}-amino)-cyclobutanecarboxylic acid
142. cis-3-([1-(4-Chloro-3-fluoro-phenyl)-ethyl]-{4-[2-(2,5-dioxo-pyrrolidin-1-yl)-ethoxy]-3-methoxy-benzyl}-amino)-cyclobutanecarboxylic acid
143. cis-3-([(R)-1-(4-Chloro-phenyl)-ethyl]-{4-[3-(2,5-dioxo-pyrrolidin-1-yl)-propyl]-3-methyl-benzyl}-amino)-cyclobutanecarboxylic acid
144. trans-4-{[{4-[2-(2,5-Dioxo-pyrrolidin-1-yl)-ethoxy]-3-methoxy-benzyl}-(1-indan-5-yl-ethyl)-amino]-methyl}-cyclohexanecarboxylic acid
145. trans-4-[((1-Indan-5-yl-ethyl)-{3-methoxy-4-[2-(3-methyl-2,5-dioxo-imidazolidin-1-yl)-ethoxy]-benzyl}-amino)-methyl]-cyclohexanecarboxylic acid
146. -4-[(((S)-5-Chloro-indan-1-yl)-{4-[2-(2,4-dioxo-3-azabicyclo[3.1.0]hex-3-yl)-ethoxy]-3-methoxy-benzyl}-amino)-methyl]-cyclohexanecarboxylic acid
147. 4-[(((S)-5-Chloro-indan-1-yl)-{4-[2-(7,9-dioxo-8-azaspiro[4.5]dec-8-yl)-ethoxy]-3-methoxy-benzyl}-amino)-methyl]-cyclohexanecarboxylic acid
148. trans-4-[(((S)-5-Chloro-4-fluoro-indan-1-yl)-{4-[2-(2,5-dioxo-pyrrolidin-1-yl)-ethoxy]-3-methoxy-benzyl}-amino)-methyl]-cyclohexanecarboxylic acid
149. trans-4-[(((S)-5-Chloro-4-fluoro-indan-1-yl)-{4-[2-(2,5-dioxo-pyrrolidin-1-yl)-ethoxy]-3-ethyl-benzyl}-amino)-methyl]-cyclohexanecarboxylic acid
150. cis-3-([(R)-1-(4-Chloro-3-fluoro-phenyl)-ethyl]-{4-[2-(2,5-dioxo-pyrrolidin-1-yl)-ethoxy]-3-methoxy-benzyl}-amino)-cyclobutanecarboxylic acid
151. cis-3-([(R)-1-(4-Chloro-3-fluoro-phenyl)-ethyl]-{4-[2-(2,5-dioxo-pyrrolidin-1-yl)-ethoxy]-3-ethyl-benzyl}-amino)-cyclobutanecarboxylic acid
152. cis-3-([(R)-1-(3,4-Dichloro-phenyl)-ethyl]-{4-[2-(2,5-dioxo-pyrrolidin-1-yl)-ethoxy]-3-methoxy-benzyl}-amino)-cyclobutanecarboxylic acid
153. cis-3-([(R)-1-(4-Chloro-phenyl)-ethyl]-{3-methyl-4-[2-(3-methyl-2,5-dioxo-imidazolidin-1-yl)-ethoxy]-benzyl}-amino)-cyclobutanecarboxylic acid
154. trans-4-({{4-[2-(2,5-Dioxo-pyrrolidin-1-yl)-ethoxy]-3-methoxy-benzyl}-[1-(4-trifluoromethyl-phenyl)-ethyl]-amino}-methyl)-cyclohexanecarboxylic acid
155. trans-4-[(((S)-5-Chloro-indan-1-yl)-{4-[2-((3aS,7aR)-1,3-dioxo-1,3,3a,4,7,7a-hexahydro-isoindol-2-yl)-ethoxy]-3-methoxy-benzyl}-amino)-methyl]-cyclohexanecarboxylic acid; hydrochloride
156. trans-4-[(((S)-5-Chloro-indan-1-yl)-{4-[2-(1,3-dioxo-1,3-dihydro-isoindol-2-yl)-ethoxy]-3-methoxy-benzyl}-amino)-methyl]-cyclohexanecarboxylic acid; hydrochloride
157. trans-4-[(((S)-5-Chloro-4-fluoro-indan-1-yl)-{3-methyl-4-[2-(3-methyl-2,5-dioxo-imidazolidin-1-yl)-ethoxy]-benzyl}-amino)-methyl]-cyclohexanecarboxylic acid
158. 3-[(((S)-5-Chloro-indan-1-yl)-{4-[2-(2,5-dioxo-pyrrolidin-1-yl)-ethoxy]-3-methoxy-benzyl}-amino)-methyl]-cyclobutanecarboxylic acid
159. cis-3-(((R)-1-Indan-5-yl-ethyl)-{3-methoxy-4-[2-(3-methyl-2,6-dioxo-3,6-dihydro-2H-pyrimidin-1-yl)-ethoxy]-benzyl}-amino)-cyclobutanecarboxylic acid
160. trans-3-(((R)-1-Indan-5-yl-ethyl)-{3-methoxy-4-[2-(3-methyl-2,6-dioxo-3,6-dihydro-2H-pyrimidin-1-yl)-ethoxy]-benzyl}-amino)-cyclobutanecarboxylic acid
or a pharmaceutically acceptable salt thereof or stereoisomer thereof or a pharmaceutically acceptable salt of the stereoisomer.

A particular group of the compounds of the present invention represented by formula 1 include compounds selected from the group consisting of:
trans-4-[([1-(2,3-Dihydro-1-benzofuran-5-yl)ethyl]{4-[2-(2,5-dioxo-pyrrolidin-1-yl)ethoxy]-3-methoxybenzyl}amino)methyl]-cyclohexanecarboxylic acid trans-4-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid trans-4-[([(S)-1-(4-Chloro-phenyl)-ethyl]-{4-[2-(2,5-dioxo-pyrrolidin-1-yl)-ethoxy]-3-methoxy-benzyl}-amino)-methyl]cyclohexanecarboxylic acid trans-4-[([(R)-1-(4-Chloro-phenyl)-ethyl]-{4-[2-(2,5-dioxo-pyrrolidin-1-yl)-ethoxy]-3-methoxy-benzyl}-amino)-methyl]-cyclohexanecarboxylic acid trans-4-[([(S)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid trans-4-[([(R)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid trans-4-[((5-Chloro-indan-1-yl)-{4-[2-(2,5-dioxo-pyrrolidin-1-yl)-ethoxy]-3-methoxy-benzyl}-amino)-methyl]-cyclohexanecarboxylic acid trans-4-[(((S)-5-Chloro-indan-1-yl)-{4-[2-(2,5-dioxo-pyrrolidin-1-yl)-ethoxy]-3-methoxy-benzyl}-amino)-methyl]-cyclohexanecarboxylic acid trans-4-[(((S)-4,5-Dichloro-indan-1-yl)-{4-[2-(2,5-dioxo-pyrrolidin-1-yl)-ethoxy]-3-methoxy-benzyl}-amino)-methyl]-cyclohexanecarboxylic acid hydrochloride trans-4-[([1-(2,3-Dihydro-benzofuran-5-yl)-ethyl]-{4-[2-(2,4-dioxo-thiazolidin-3-yl)-ethoxy]-3-methoxy-benzyl}-amino)-methyl]-cyclohexanecarboxylic acid trans-4-({{3-Chloro-4-[2-(2,5-dioxo-pyrrolidin-1-yl)-ethoxy]-benzyl}-[1-(2,3-dihydro-benzofuran-5-yl)-ethyl]-amino}-methyl)-cyclohexanecarboxylic acid trans-4-[([1-(2,3-Dihydro-benzofuran-5-yl)-ethyl]-{4-[2-(2,5-dioxo-pyrrolidin-1-yl)-ethoxy]-3-methyl-benzyl}-amino)-methyl]-cyclohexanecarboxylic acid trans-4-[([1-(2,3-Dihydro-benzofuran-5-yl)-propyl]-{4-[2-(2,5-dioxo-pyrrolidin-1-yl)-ethoxy]-3-methoxy-benzyl}-amino)-methyl]-cyclohexanecarboxylic acid trans-4-[([1-(2,3-Dihydro-benzofuran-5-yl)-ethyl]-{4-[2-(2,4-dioxo-oxazolidin-3-yl)-ethoxy]-3-methoxy-benzyl}-amino)-methyl]-cyclohexanecarboxylic acid trans-4-[((5-Chloro-indan-1-yl)-{4-[2-(2,4-dioxo-thiazolidin-3-yl)-ethoxy]-3-methoxy-benzyl}-amino)-methyl]-cyclohexanecarboxylic acid trans-4-[([1-(4-Chloro-3-methyl-phenyl)-ethyl]-{4-[2-(2,5-dioxo-pyrrolidin-1-yl)-ethoxy]-3-methoxy-benzyl}-amino)-methyl]-cyclohexanecarboxylic acid trans-4-[([(S)-1-(4-Chloro-3-methyl-phenyl)-ethyl]-{4-[2-(2,5-dioxo-pyrrolidin-1-yl)-ethoxy]-3-methoxy-benzyl}-amino)-methyl]-cyclohexanecarboxylic acid trans-4-[(((S)-5-Chloro-indan-1-yl)-{4-[2-(2,5-dioxo-pyrrolidin-1-yl)-ethoxy]-3-methyl-benzyl}-amino)-methyl]-cyclohexanecarboxylic acid trans-4-[([1-(2,3-Dihydro-benzofuran-5-yl)-ethyl]-{4-[2-(2,4-dioxo-thiazolidin-3-yl)-ethoxy]-3-methyl-benzyl}-amino)-methyl]-cyclohexanecarboxylic acid trans-4-[([(S)-1-(4-Chloro-phenyl)-ethyl]-{4-[2-(2,4-dioxo-thiazolidin-3-yl)-ethoxy]-3-methoxy-benzyl}-amino)-methyl]-cyclohexanecarboxylic acid trans-4-[([(S)-1-(4-Chloro-phenyl)-ethyl]-{4-[2-(2,4-dioxo-oxazolidin-3-yl)-ethoxy]-3-methoxy-benzyl}-amino)-methyl]-cyclohexanecarboxylic acid trans-4-[([(S)-1-(4-Chloro-phenyl)-ethyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid trans-4-[([1-(4-Chloro-phenyl)-propyl]-{4-[2-(2,5-dioxo-pyrrolidin-1-yl)-ethoxy]-3-methoxy-benzyl}-amino)-methyl]-cyclohexanecarboxylic acid trans-4-[([1-(4-Chloro-phenyl)-propyl]-{3-methoxy-4-[2-(3-methyl-2,5-dioxo-imidazolidin-1-yl)-ethoxy]-benzyl}-amino)-methyl]-cyclohexanecarboxylic acid trans-4-[([1-(2,3-Dihydro-benzofuran-5-yl)-propyl]-{4-[2-(2,5-dioxo-pyrrolidin-1-yl)-ethoxy]-3-methyl-benzyl}-amino)-methyl]-cyclohexanecarboxylic acid trans-4-[([(S)-1-(4-Chloro-phenyl)-ethyl]-{4-[2-(2,5-dioxo-pyrrolidin-1-yl)-ethoxy]-3-ethyl-benzyl}-amino)-methyl]-cyclohexanecarboxylic acid trans-4-[([1-(2,3-Dihydro-benzofuran-5-yl)-ethyl]-{4-[2-(2,5-dioxo-pyrrolidin-1-yl)-ethoxy]-3-ethyl-benzyl}-amino)-methyl]-cyclohexanecarboxylic acid trans-4-[([1-(4-Chloro-3-fluoro-phenyl)-ethyl]-{4-[2-(2,5-dioxo-pyrrolidin-1-yl)-ethoxy]-3-methoxy-benzyl}-amino)-methyl]-cyclohexanecarboxylic acid trans-4-[([(S)-1-(4-Chloro-phenyl)-ethyl]-{4-[2-(2,5-dioxo-pyrrolidin-1-yl)-ethylsulfanyl]-3-methoxy-benzyl}-amino)-methyl]-cyclohexanecarboxylic acid trans-4-[(((S)-5-Chloro-indan-1-yl)-{4-[2-(2,5-dioxo-pyrrolidin-1-yl)-ethylsulfanyl]-3-methoxy-benzyl}-amino)-methyl]-cyclohexanecarboxylic acid trans-4-[([1-(4-Chloro-3-fluoro-phenyl)-ethyl]-{4-[2-(2,5-dioxo-pyrrolidin-1-yl)-ethoxy]-3-ethyl-benzyl}-amino)-methyl]-cyclohexanecarboxylic acid trans-4-[([(S)-1-(4-Chloro-3-fluoro-phenyl)-ethyl]-{4-[2-(2,5-dioxo-pyrrolidin-1-yl)-ethoxy]-3-ethyl-benzyl}-amino)-methyl]-cyclohexanecarboxylic acid (1R,3R)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid (1R,3R)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid (1S,3S)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid (1S,3S)-3-[([1-(4-Chloro-phenyl)-propyl]-{4-[2-(2,5-dioxo-pyrrolidin-1-yl)-ethoxy]-3-methoxy-benzyl}-amino)-methyl]-2,2-dimethyl-cyclopropanecarboxylic acid cis-3-([(R)-1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid 3-([1-(2,3-Dihydro-benzofuran-5-yl)-ethyl]-{4-[2-(2,5-dioxo-pyrrolidin-1-yl)-ethoxy]-3-methoxy-benzyl}-amino)-cyclobutanecarboxylic acid trans-4-[(((S)-5-Chloro-4-fluoro-indan-1-yl)-{4-[2-(2,5-dioxo-pyrrolidin-1-yl)-ethoxy]-3-methoxy-benzyl}-amino)-methyl]-cyclohexanecarboxylic acid or a pharmaceutically acceptable salt thereof or stereoisomer thereof or a pharmaceutically acceptable salt of the stereoisomer.

A further embodiment of the invention includes compounds of formula 4,

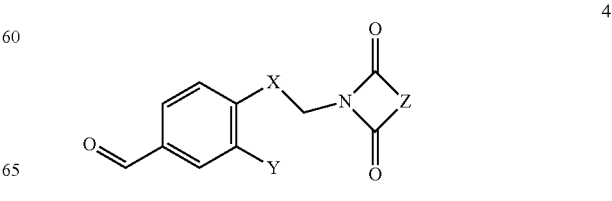

wherein

X represents a $C_2$ aliphatic hydrocarbon bridge optionally containing a double bond or a triple bond or a heteroatom selected from O and S, or —CH(CH$_2$)CH—;

Y represents hydrogen, halogen, $C_{1-4}$ alkyl, $C_{1-4}$ alkoxy or $C_{1-4}$ hydroxyalkyl; and Z represents a $C_{1-4}$ aliphatic hydrocarbon bridge optionally containing one double bond, and/or one or more heteroatom selected from O, S, N and N(CH$_3$) or represents a $C_{2-4}$ aliphatic hydrocarbon bridge fused with a $C_{3-6}$ cycloalkyl ring optionally containing one or more double bond or with a phenyl ring or represents a $C_{1-4}$ aliphatic hydrocarbon bridge substituted with a spiro $C_{3-6}$ cycloalkyl ring optionally containing one or more double bond.

Particularly compounds represented by formula 4 include compounds selected from the group consisting of 4-[2-(2,5-Dioxo-pyrrolidin-1-yl)-ethoxy]-3-methoxy-benzaldehyde 4-[2-(2,5-Dioxo-pyrrolidin-1-yl)-ethoxy]-3-methyl-benzaldehyde 4-[2-(2,5-Dioxo-pyrrolidin-1-yl)-ethoxy]-3-ethyl-benzaldehyde 3-Chloro-4-[2-(2,5-Dioxo-pyrrolidin-1-yl)-ethoxy]-benzaldehyde 4-[2-(2,5-Dioxo-pyrrolidin-1-yl)-ethoxy]-3-fluoro-benzaldehyde 4-[2-(2,5-Dioxo-pyrrolidin-1-yl)-ethoxy]-3-hydroxymethyl-benzaldehyde 4-[2-(2,5-Dioxo-pyrrolidin-1-yl)-ethoxy]-benzaldehyde 3-Methoxy-4-[2-(3-methyl-2,5-dioxo-imidazolidin-1-yl)-ethoxy]-benzaldehyde 3-Methyl-4-[2-(3-methyl-2,5-dioxo-imidazolidin-1-yl)-ethoxy]-benzaldehyde 3-Chloro-4-[2-(3-methyl-2,5-dioxo-imidazolidin-1-yl)-ethoxy]-benzaldehyde 4-[2-(2,4-Dioxo-thiazolidin-3-yl)-ethoxy]-3-methoxy-benzaldehyde 4-[2-(2,4-Dioxo-thiazolidin-3-yl)-ethoxy]-3-methyl-benzaldehyde 4-[2-(2,4-Dioxo-oxazolidin-3-yl)-ethoxy]-3-methoxy-benzaldehyde 3-Methoxy-4-[2-(3-methyl-2,6-dioxo-3,6-dihydro-2H-pyrimidin-1-yl)-ethoxy]-benzaldehyde 3-Methyl-4-[2-(3-methyl-2,6-dioxo-3,6-dihydro-2H-pyrimidin-1-yl)-ethoxy]-benzaldehyde 4-[2-(2,6-Dioxo-piperidin-1-yl)-ethoxy]-3-methoxy-benzaldehyde 4-[2-(2,5-Dioxo-pyrrolidin-1-yl)-ethylsulfanyl]-3-methoxy-benzaldehyde 4-[(E)-3-(2,5-Dioxo-pyrrolidin-1-yl)-propenyl]-3-methoxy-benzaldehyde 4-[3-(2,5-Dioxo-pyrrolidin-1-yl)-prop-1-ynyl]-3-methoxy-benzaldehyde 4-[3-(2,5-Dioxo-pyrrolidin-1-yl)-prop-1-ynyl]-3-methyl-benzaldehyde 3-Methyl-4-[3-(3-methyl-2,5-dioxo-imidazolidin-1-yl)-prop-1-ynyl]-benzaldehyde 3-Methoxy-4-[3-(3-methyl-2,5-dioxo-imidazolidin-1-yl)-prop-1-ynyl]-benzaldehyde 4-[3-(2,5-Dioxo-pyrrolidin-1-yl)-propyl]-3-methoxy-benzaldehyde 4-[3-(2,5-Dioxo-pyrrolidin-1-yl)-propyl]-3-methyl-benzaldehyde 3-Chloro-4-[3-(2,5-dioxo-pyrrolidin-1-yl)-propyl]-benzaldehyde 3-Methoxy-4-[3-(3-methyl-2,5-dioxo-imidazolidin-1-yl)-propyl]-benzaldehyde 4-[2-(2,5-Dioxo-pyrrolidin-1-ylmethyl)-cyclopropyl]-3-methoxy-benzaldehyde 4-[2-(2,4-Dioxo-3-aza-bicyclo[3.1.0]hex-3-yl)-ethoxy]-3-methoxy-benzaldehyde 4-[2-((3aS,7aR)-1,3-Dioxo-1,3,3a,4,7,7a-hexahydro-isoindol-2-yl)-ethoxy]-3-methoxy-benzaldehyde 4-[2-(1,3-Dioxo-1,3-dihydro-isoindol-2-yl)-ethoxy]-3-methoxy-benzaldehyde 4-[2-(7,9-Dioxo-8-aza-spiro[4.5]dec-8-yl)-ethoxy]-3-methoxy-benzaldehyde.

A further embodiment of the invention includes compounds of formula 2

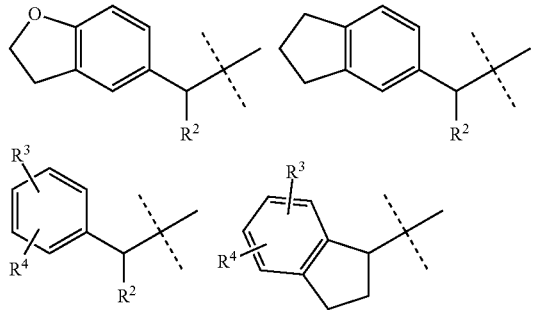

wherein

R$^1$ represents a group selected from the group consisting of

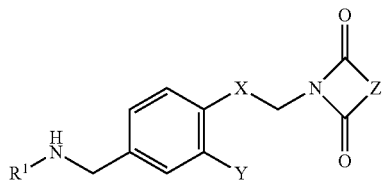

wherein

R$^2$ represents hydrogen or $C_{1-4}$ alkyl group;

R$^3$ represents hydrogen, halogen, CF$_3$, CN or $C_{1-4}$ alkyl; and

R$^4$ represents hydrogen, halogen or $C_{1-4}$ alkyl;

X represents a $C_2$ aliphatic hydrocarbon bridge optionally containing a double bond or a triple bond or a heteroatom selected from O and S, or —CH(CH$_2$)CH—;

Y represents hydrogen, halogen, $C_{1-4}$ alkyl, $C_{1-4}$ alkoxy or $C_{1-4}$ hydroxyalkyl; and Z represents a $C_{1-4}$ aliphatic hydrocarbon bridge optionally containing one double bond, and/or one or more heteroatom selected from O, S, N and N(CH$_3$) or represents a $C_{2-4}$ aliphatic hydrocarbon bridge fused with a $C_{3-6}$ cycloalkyl ring optionally containing one or more double bond or with a phenyl ring or represents a $C_{1-4}$ aliphatic hydrocarbon bridge substituted with a spiro $C_{3-6}$ cycloalkyl ring optionally containing one or more double bond;

or a salt thereof.

Particularly compounds represented by formula 2 include compounds selected from the group consisting of 1. 1-[2-(4-{[1-(2,3-Dihydro-benzofuran-5-yl)-ethylamino]-methyl}-2-methoxy-phenoxy)-ethyl]-pyrrolidine-2,5-dione naphthalene-1,5-disulfonic acid salt 2. 1-[2-(4-{[(S)-1-(4-Chloro-phenyl)-ethylamino]-methyl}-2-methoxy-phenoxy)-ethyl]-pyrrolidine-2,5-dione 3. 1-[2-(4-{[(R)-1-(4-Chloro-phenyl)-ethylamino]-methyl}-2-methoxy-phenoxy)-ethyl]-pyrrolidine-2,5-dione
4. 1-[2-(4-{[(S)-1-(4-Chloro-phenyl)-ethylamino]-methyl}-2-methyl-phenoxy)-ethyl]-pyrrolidine-2,5-dione
5. 1-[2-(4-{[(R)-1-(4-Chloro-phenyl)-ethylamino]-methyl}-2-methyl-phenoxy)-ethyl]-pyrrolidine-2,5-dione
6. 1-(2-{4-[(5-Chloro-indan-1-ylamino)-methyl]-2-methoxy-phenoxy}-ethyl)-pyrrolidine-2,5-dione
7. 1-(2-{4-[((S)-5-Chloro-indan-1-ylamino)-methyl]-2-methoxy-phenoxy}-ethyl)-pyrrolidine-2,5-dione
8. 1-(2-{4-[((S)-4,5-Dichloro-indan-1-ylamino)-methyl]-2-methoxy-phenoxy}-ethyl)-pyrrolidine-2,5-dione
9. 1-(2-{4-[((S)-5-Chloro-4-fluoro-indan-1-ylamino)-methyl]-2-methoxy-phenoxy}-ethyl)-pyrrolidine-2,5-dione
10. 3-[2-(4-{[1-(2,3-Dihydro-benzofuran-5-yl)-ethylamino]-methyl}-2-methoxy-phenoxy)-ethyl]-thiazolidine-2,4-dione
11. 1-[2-(2-Chloro-4-{[1-(2,3-dihydro-benzofuran-5-yl)-ethylamino]-methyl}-phenoxy)-ethyl]-pyrrolidine-2,5-dione
12. 1-[2-(4-{[1-(2,3-Dihydro-benzofuran-5-yl)-ethylamino]-methyl}-2-methyl-phenoxy)-ethyl]-pyrrolidine-2,5-dione
13. 1-[2-(4-{[1-(2,3-Dihydro-benzofuran-5-yl)-propylamino]-methyl}-2-methoxy-phenoxy)-ethyl]-pyrrolidine-2,5-dione
14. 3-[2-(4-{[1-(2,3-Dihydro-benzofuran-5-yl)-ethylamino]-methyl}-2-methoxy-phenoxy)-ethyl]-oxazolidine-2,4-dione
15. 3-(2-{2-Chloro-4-[(5-chloro-indan-1-ylamino)-methyl]-phenoxy}-ethyl)-1-methyl-imidazolidine-2,4-dione
16. 1-(2-{2-Chloro-4-[(5-chloro-indan-1-ylamino)-methyl]-phenoxy}-ethyl)-pyrrolidine-2,5-dione
17. 3-[2-(2-Chloro-4-{[1(2,3-dihydro-benzofuran-5-yl)-ethylamino]-methyl}-phenoxy)-ethyl]-1-methyl-imidazolidine-2,4-dione
18. 3-[2-(2-Chloro-4-{[(S)-1-(4-chloro-phenyl)-ethylamino]-methyl}-phenoxy)-ethyl]-1-methyl-imidazolidine-2,4-dione
19. 3-(2-{4-[(5-Chloro-indan-1-ylamino)-methyl]-2-methoxy-phenoxy}-ethyl)-thiazolidine-2,4-dione
20. 1-[2-(4-{[1-(4-Chloro-3-methyl-phenyl)-ethylamino]-methyl}-2-methoxy-phenoxy)-ethyl]-pyrrolidine-2,5-dione
21. 1-[2-(4-{[(S)-1-(4-Chloro-3-methyl-phenyl)-ethylamino]-methyl}-2-methoxy-phenoxy)-ethyl]-pyrrolidine-2,5-dione
22. 1-[2-(4-{[(R)-1-(4-Chloro-3-methyl-phenyl)-ethylamino]-methyl}-2-methoxy-phenoxy)-ethyl]-pyrrolidine-2,5-dione
23. 3-[2-(4-{[1-(2,3-Dihydro-benzofuran-5-yl)-propylamino]-methyl}-2-methoxy-phenoxy)-ethyl]-1-methyl-imidazolidine-2,4-dione
24. 1-(2-{4-[(5-Chloro-indan-1-ylamino)-methyl]-2-methyl-phenoxy}-ethyl)-pyrrolidine-2,5-dione
25. 1-(2-{4-[((S)-5-Chloro-indan-1-ylamino)-methyl]-2-methyl-phenoxy}-ethyl)-pyrrolidine-2,5-dione1-(2-{4-[((R)-5-Chloro-indan-1-ylamino)-methyl]-2-methyl-phenoxy}-ethyl)-pyrrolidine-2,5-dione
26. 1-[2-(2-Chloro-4-{[(S)-1-(4-chloro-phenyl)-ethylamino]-methyl}-phenoxy)-ethyl]-pyrrolidine-2,5-dione
27. 3-[2-(4-{[1-(2,3-Dihydro-benzofuran-5-yl)-ethylamino]-methyl}-2-methyl-phenoxy)-ethyl]-thiazolidine-2,4-dione
28. 3-[2-(4-{[(S)-1-(4-Chloro-phenyl)-ethylamino]-methyl}-2-methoxy-phenoxy)-ethyl]-thiazolidine-2,4-dione
29. 1-[(E)-3-(4-{[1-(2,3-Dihydro-benzofuran-5-yl)-ethylamino]-methyl}-2-methoxy-phenyl)-allyl]-pyrrolidine-2,5-dione
30. 3-[2-(4-{[(S)-1-(4-Chloro-phenyl)-ethylamino]-methyl}-2-methoxy-phenoxy)-ethyl]-oxazolidine-2,4-dione
31. 3-[2-(4-{[(S)-1-(4-Chloro-phenyl)-ethylamino]-methyl}-2-methoxy-phenoxy)-ethyl]-1-methyl-1H-pyrimidine-2,4-dione
32. 1-[2-(4-{[1-(2,3-Dihydro-benzofuran-5-yl)-ethylamino]-methyl}-2-methoxy-phenoxy)-ethyl]-piperidine-2,6-dione
33. 3-[2-(4-{[(S)-1-(4-Chloro-phenyl)-ethylamino]-methyl}-2-methyl-phenoxy)-ethyl]-1-methyl-imidazolidine-2,4-dione
34. 1-[3-(4-{[1-(2,3-Dihydro-benzofuran-5-yl)-ethylamino]-methyl}-2-methoxy-phenyl)-propyl]-pyrrolidine-2,5-dione
35. 1-(2-{4-[(5-Chloro-6-methyl-indan-1-ylamino)-methyl]-2-methoxy-phenoxy}-ethyl)-pyrrolidine-2,5-dione
36. 1-(2-{4-[(5-Chloro-4-methyl-indan-1-ylamino)-methyl]-2-methoxy-phenoxy}-ethyl)-pyrrolidine-2,5-dione
37. 1-(3-{4-[(5-Chloro-indan-1-ylamino)-methyl]-2-methoxy-phenyl}-propyl)-pyrrolidine-2,5-dione
38. 1-(3-{4-[((S)-5-Chloro-indan-1-ylamino)-methyl]-2-methoxy-phenyl}-propyl)-pyrrolidine-2,5-dione
39. 1-(3-{4-[((R)-5-Chloro-indan-1-ylamino)-methyl]-2-methoxy-phenyl}-propyl)-pyrrolidine-2,5-dione
40. 1-[3-(2-Chloro-4-{[1-(2,3-dihydro-benzofuran-5-yl)-ethylamino]-methyl}-phenyl)-propyl]-pyrrolidine-2,5-dione
41. 3-(2-{4-[(5-Chloro-indan-1-ylamino)-methyl]-2-methoxy-phenoxy}-ethyl)-1-methyl-1H-pyrimidine-2,4-dione
42. 1-[2-(4-{[1-(2,3-Dihydro-benzofuran-5-yl)-ethylamino]-methyl}-2-methoxy-phenyl)-cyclopropylmethyl]-pyrrolidine-2,5-dione
43. 3-(3-{4-[(5-Chloro-indan-1-ylamino)-methyl]-2-methoxy-phenyl}-propyl)-1-methyl-imidazolidine-2,4-dione
44. 3-[3-(4-{[(S)-1-(4-Chloro-phenyl)-ethylamino]-methyl}-2-methoxy-phenyl)-propyl]-1-methyl-imidazolidine-2,4-dione
45. 3-(2-{4-[(5-Chloro-indan-1-ylamino)-methyl]-2-methoxy-phenoxy}-ethyl)-1-methyl-imidazolidine-2,4-dione
46. 3-[2-(4-{[(S)-1-(4-Chloro-phenyl)-ethylamino]-methyl}-2-methoxy-phenoxy)-ethyl]-1-methyl-imidazolidine-2,4-dione
47. 1-[3-(4-{[(S)-1-(4-Chloro-phenyl)-ethylamino]-methyl}-2-methyl-phenyl)-propyl]-pyrrolidine-2,5-dione
48. 1-[3-(4-{[(S)-1-(4-Chloro-phenyl)-ethylamino]-methyl}-2-methoxy-phenyl)-prop-2-ynyl]-pyrrolidine-2,5-dione
49. 1-[3-(4-{[(S)-1-(4-Chloro-phenyl)-ethylamino]-methyl}-2-methoxy-phenyl)-propyl]-pyrrolidine-2,5-dione
50. 3-(2-{4-[(5-Chloro-indan-1-ylamino)-methyl]-2-methyl-phenoxy}-ethyl)-1-methyl-imidazolidine-2,4-dione
51. 3-[2-(4-{[(S)-1-(4-Chloro-phenyl)-ethylamino]-methyl}-2-methyl-phenoxy)-ethyl]-1-methyl-1H-pyrimidine-2,4-dione
52. 3-[2-(4-{[1-(2,3-Dihydro-benzofuran-5-yl)-ethylamino]-methyl}-2-methoxy-phenoxy)-ethyl]-1-methyl-1H-pyrimidine-2,4-dione
53. 3-[2-(4-{[1-(2,3-Dihydro-benzofuran-5-yl)-ethylamino]-methyl}-2-methyl-phenoxy)-ethyl]-1-methyl-1H-pyrimidine-2,4-dione
54. 4-(1-{4-[2-(2,5-Dioxo-pyrrolidin-1-yl)-ethoxy]-3-methyl-benzylamino}-ethyl)-benzonitrile 55. 4-(1-{3-Methoxy-4-[2-(3-methyl-2,6-dioxo-3,6-dihydro-2H-pyrimidin-1-yl)-ethoxy]-benzylamino}-ethyl)-benzonitrile
56. 1-[2-(4-{[1-(4-Chloro-phenyl)-propylamino]-methyl}-2-methoxy-phenoxy)-ethyl]-pyrrolidine-2,5-dione
57. 3-[2-(4-{[1-(4-Chloro-phenyl)-propylamino]-methyl}-2-methyl-phenoxy)-ethyl]-1-methyl-1H-pyrimidine-2,4-dione
58. 3-[2-(4-{[1-(4-Chloro-phenyl)-propylamino]-methyl}-2-methoxy-phenoxy)-ethyl]-1-methyl-imidazolidine-2,4-dione
59. 1-[3-(4-{[1-(2,3-Dihydro-benzofuran-5-yl)-propylamino]-methyl}-2-methoxy-phenyl)-propyl]-pyrrolidine-2,5-dione
60. 3-[2-(4-{[1-(4-Chloro-phenyl)-propylamino]-methyl}-2-methoxy-phenoxy)-ethyl]-1-methyl-imidazolidine-2,4-dione
61. 3-[2-(4-{[1-(4-Chloro-phenyl)-propylamino]-methyl}-2-methoxy-phenoxy)-ethyl]-1-methyl-1H-pyrimidine-2,4-dione
62. 1-[2-(4-{[1-(2,3-Dihydro-benzofuran-5-yl)-propylamino]-methyl}-2-methyl-phenoxy)-ethyl]-pyrrolidine-2,5-dione
63. 3-[2-(4-{[1-(4-Chloro-phenyl)-propylamino]-methyl}-2-methyl-phenoxy)-ethyl]-1-methyl-imidazolidine-2,4-dione
64. 1-(2-{4-[((S)-5-Chloro-indan-1-ylamino)-methyl]-2-ethyl-phenoxy}-ethyl)-pyrrolidine-2,5-dione
65. 1-(2-{4-[((S)-5-Chloro-indan-1-ylamino)-methyl]-2-fluoro-phenoxy}-ethyl)-pyrrolidine-2,5-dione
66. 1-[2-(4-{[(S)-1-(4-Chloro-phenyl)-ethylamino]-methyl}-2-fluoro-phenoxy)-ethyl]-pyrrolidine-2,5-dione
67. 1-(2-{4-[((S)-5,6-Dichloro-indan-1-ylamino)-methyl]-2-methoxy-phenoxy}-ethyl)-pyrrolidine-2,5-dione
68. 1-[2-(4-{[(S)-1-(4-Chloro-phenyl)-ethylamino]-methyl}-2-ethyl-phenoxy)-ethyl]-pyrrolidine-2,5-dione
69. 1-[2-(4-{[1-(2,3-Dihydro-benzofuran-5-yl)-ethylamino]-methyl}-2-ethyl-phenoxy)-ethyl]-pyrrolidine-2,5-dione
70. 1-[2-(4-{[1-(3,4-Dichloro-phenyl)-ethylamino]-methyl}-2-methoxy-phenoxy)-ethyl]-pyrrolidine-2,5-dione
71. 1-[2-(4-{[1-(3,4-Dichloro-phenyl)-ethylamino]-methyl}-2-methyl-phenoxy)-ethyl]-pyrrolidine-2,5-dione
72. 1-[2-(4-{[(S)-1-(4-Chloro-phenyl)-ethylamino]-methyl}-phenoxy)-ethyl]-pyrrolidine-2,5-dione
73. 3-[2-(4-{[1-(3,4-Dichloro-phenyl)-ethylamino]-methyl}-2-methyl-phenoxy)-ethyl]-1-methyl-imidazolidine-2,4-dione
74. 1-[2-(4-{[1-(4-Ethyl-phenyl)-ethylamino]-methyl}-2-methoxy-phenoxy)-ethyl]-pyrrolidine-2,5-dione
75. 1-[2-(4-{[1-(4-Chloro-3-fluoro-phenyl)-ethylamino]-methyl}-2-methoxy-phenoxy)-ethyl]-pyrrolidine-2,5-dione
76. 1-(2-{2-Methyl-4-[(1-p-tolyl-ethylamino)-methyl]-phenoxy}-ethyl)-pyrrolidine-2,5-dione
77. 1-(2-{2-Methoxy-4-[(1-p-tolyl-ethylamino)-methyl]-phenoxy}-ethyl)-pyrrolidine-2,5-dione
78. 1-[2-(4-{[(S)-1-(4-Chloro-phenyl)-ethylamino]-methyl}-2-hydroxymethyl-phenoxy)-ethyl]-pyrrolidine-2,5-dione
79. -(2-{4-[((S)-4,5-Dichloro-indan-1-ylamino)-methyl]-2-ethyl-phenoxy}-ethyl)-pyrrolidine-2,5-dione
80. 1-[2-(4-{[(S)-1-(4-Chloro-phenyl)-ethylamino]-methyl}-2-methoxy-phenylsulfanyl)-ethyl]-pyrrolidine-2,5-dione
81. 1-(2-{4-[((S)-5-Chloro-indan-1-ylamino)-methyl]-2-methoxy-phenylsulfanyl}-ethyl)-pyrrolidine-2,5-dione
82. 1-[2-(4-{[1-(4-Chloro-3-fluoro-phenyl)-ethylamino]-methyl}-2-ethyl-phenoxy)-ethyl]-pyrrolidine-2,5-dione
83. 1-[2-(4-{[(R)-1-(4-Chloro-3-fluoro-phenyl)-ethylamino]-methyl}-2-ethyl-phenoxy)-ethyl]-pyrrolidine-2,5-dione
84. 1-[2-(4-{[(S)-1-(4-Chloro-3-fluoro-phenyl)-ethylamino]-methyl}-2-ethyl-phenoxy)-ethyl]-pyrrolidine-2,5-dione
85. 1-[2-(4-{[1-(4-Chloro-3-fluoro-phenyl)-ethylamino]-methyl}-2-fluoro-phenoxy)-ethyl]-pyrrolidine-2,5-dione
86. 1-(2-{4-[(4-Chloro-5-fluoro-indan-1-ylamino)-methyl]-2-methoxy-phenoxy}-ethyl)-pyrrolidine-2,5-dione
87. 1-(2-{4-[(6-Chloro-5-fluoro-indan-1-ylamino)-methyl]-2-methoxy-phenoxy}-ethyl)-pyrrolidine-2,5-dione
88. 1-(2-{4-[(6-Chloro-5-fluoro-indan-1-ylamino)-methyl]-2-ethyl-phenoxy}-ethyl)-pyrrolidine-2,5-dione
89. 1-(2-{4-[(4-Chloro-5-fluoro-indan-1-ylamino)-methyl]-2-ethyl-phenoxy}-ethyl)-pyrrolidine-2,5-dione
90. 1-(2-{4-[(6-Chloro-5-fluoro-indan-1-ylamino)-methyl]-2-fluoro-phenoxy}-ethyl)-pyrrolidine-2,5-dione
91. 1-(2-{4-[(5-Chloro-6-fluoro-indan-1-ylamino)-methyl]-2-methoxy-phenoxy}-ethyl)-pyrrolidine-2,5-dione
92. 1-[2-(4-{[(R)-1-(2,3-Dihydro-benzofuran-5-yl)-ethylamino]-methyl}-2-methoxy-phenoxy)-ethyl]-pyrrolidine-2,5-dione
93. 1-[2-(4-{[(S)-1-(2,3-Dihydro-benzofuran-5-yl)-ethylamino]-methyl}-2-methoxy-phenoxy)-ethyl]-pyrrolidine-2,5-dione.

General Procedures:

Starting materials and solvents used in the synthesis are obtained from chemical vendors such as ABCR, Aldrich, Acros, Apollo, Fluka, Netchem, Lancaster and others.

The crude product is purified by column chromatography or flash chromatography.

In first step the appropriate benzaldehydes (4=4a-f) are synthesized in different way depending on the side chain of dioxoamide derivatives as described on Scheme 1.

The synthesis of compound formula 4a, wherein X represents —O—$CH_2$— or —S—$CH_2$—, is done by alkylation of 4-hydroxy- or 4-mercapto-benzaldehydes 6a with dibromoethane and dioxoamide (route via 6a', 7a') or bromo-ethyldioxoamide derivatives (route via 7a) in the presence of a base, preferably $K_2CO_3$, TEA or sodium hydride using acetonitrile, DMF or MEK as solvent. Compounds of formula 4f, wherein X represents —$CH_2$—O— or —$CH_2$—S—, can be prepared analogously by alkylation of the corresponding benzyl alcohols or benzyl thiols of formula 6d with dibromomethane and dioxoamide (route via 6d', 7c') or bromomethyldioxoamide derivatives (route via 7c) in the presence of a base, preferably $K_2CO_3$, TEA or sodium hydride using acetonitrile, DMF or MEK as solvent An unsaturated compound of formula 4b, wherein X represents —C≡C—, can be synthesized in a Sonogashira reaction (Sonogashira, K. et al. *Tetrahedron Lett.* 1975, 16 (50), 4467) and an unsaturated compound of formula 4d, wherein X represents —CH═CH—, can be synthesized in a Suzuki coupling (Suzuki, A. *Tetrahedron Lett.* 1979, 20 (36), 3437) followed by hydrolysis of the resulted compound of formula 4d'. A compound of formula 4c, wherein X represents —$CH_2$—$CH_2$—, can be prepared by hydrogenation of the corresponding compound of formula 4b or 4d'. A compound of formula 4e, wherein X represents —CH($CH_2$)CH— can be synthesized from the corresponding protected allylic derivative of formula 4d' using diazomethane (Scheme 1).

Scheme 1
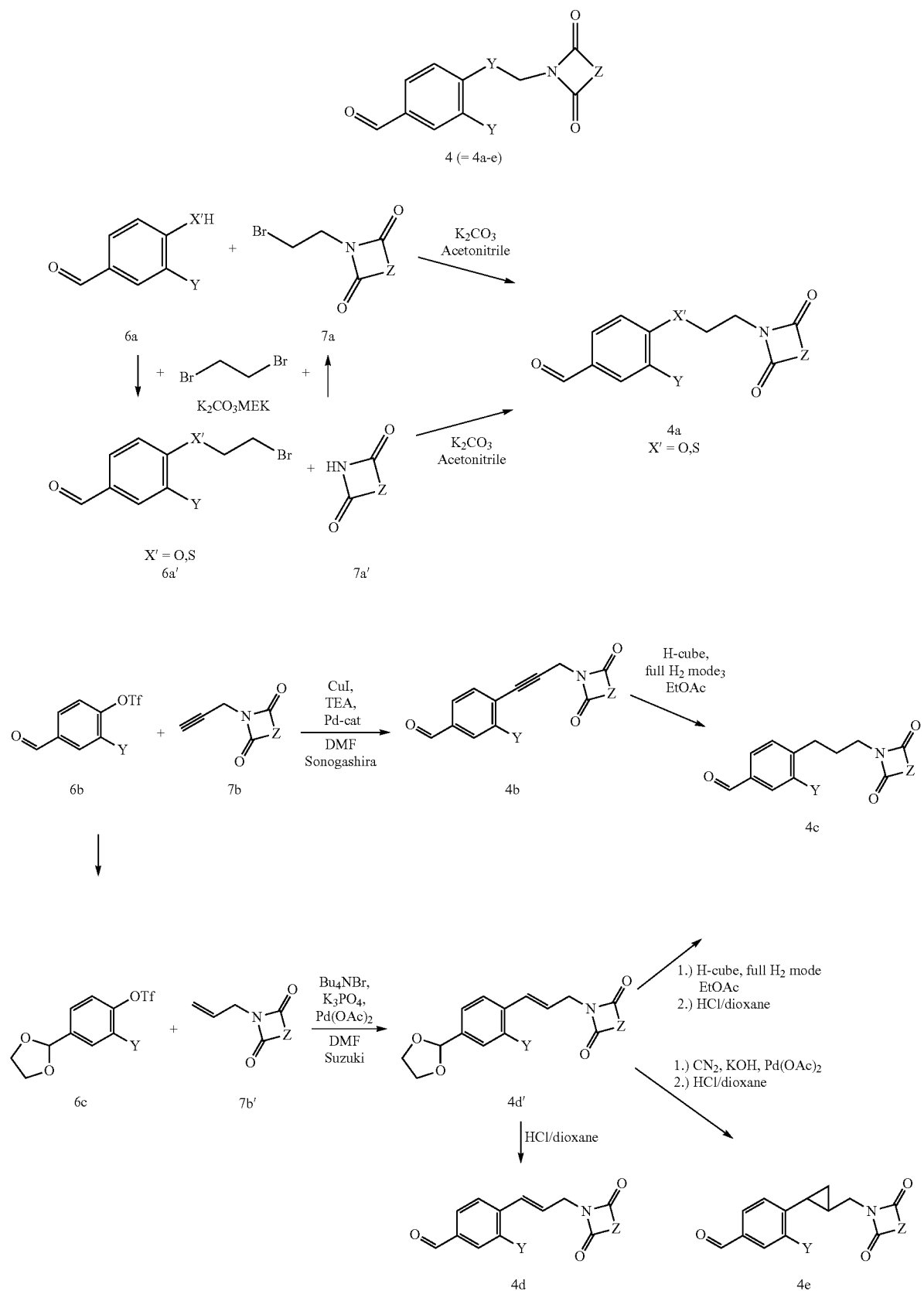

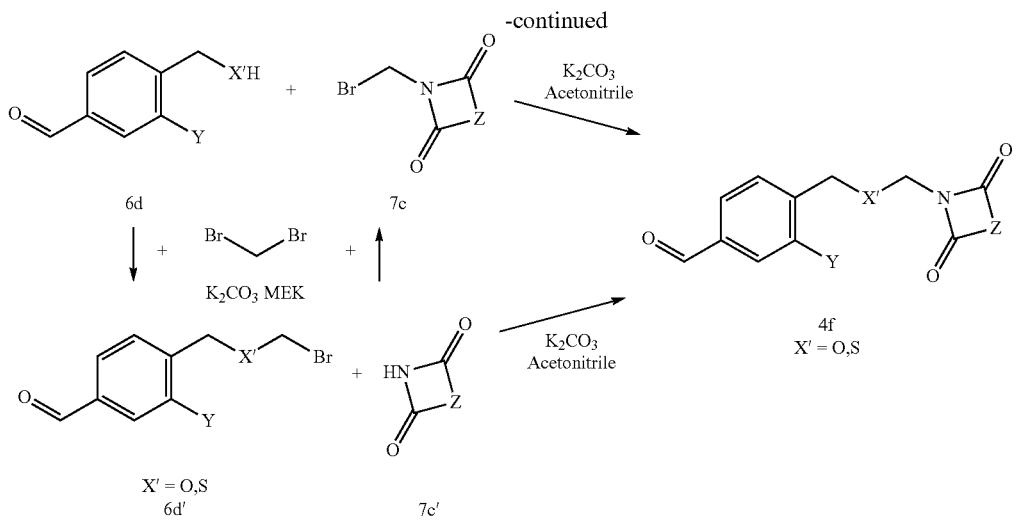

Then the benzaldehydes 4 are reacted with different primary amines 5 in mild reductive amination conditions (NaBH(OAc)₃ in THF or 2-picoline borane complex in EtOH). The resulted secondary amines 2 are reacted with different formyl- (R': —CHO) or oxo- (R': =O) cycloalkane carboxylic acid esters 3 in a repeated reductive amination step. The resulted esters (1, R=Me, Et) are optionally hydrolyzed in acidic conditions. The crude 1 is purified by chromatography, crystallization or via salt formation (Scheme 2).

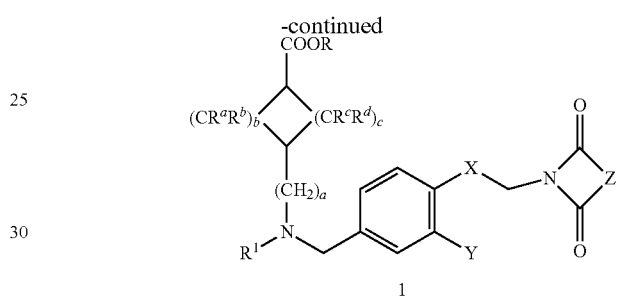

Starting materials of formula 3, 5 and 7 are commercially available or can be prepared by known methods. Compounds of formula 6 are commercially available (6a) or can be prepared by known methods. Compounds of formula 6b can be synthesized with triflation of the corresponding alcohol. A compound of formula 6c is a protected derivative of an aldehyde of formula 6a with ethyleneglycol. A compound of formula 6d can be synthesized from commercially available benzoic acid derivatives by known method (Scheme 3).

Scheme 3

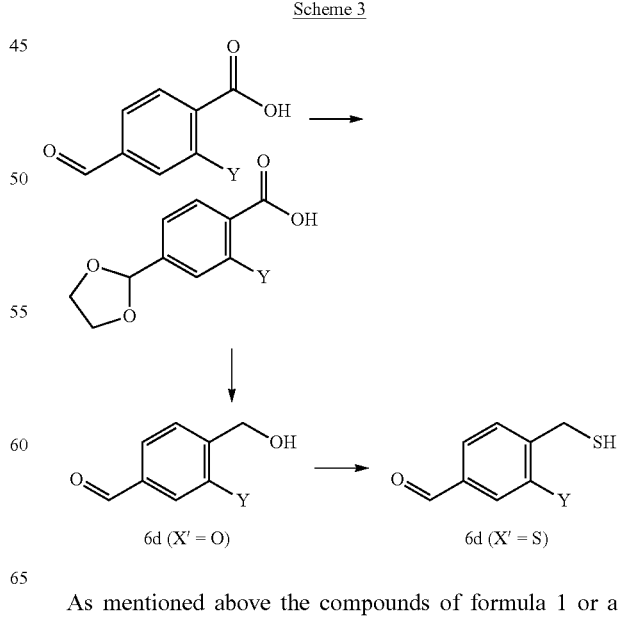

Scheme 2

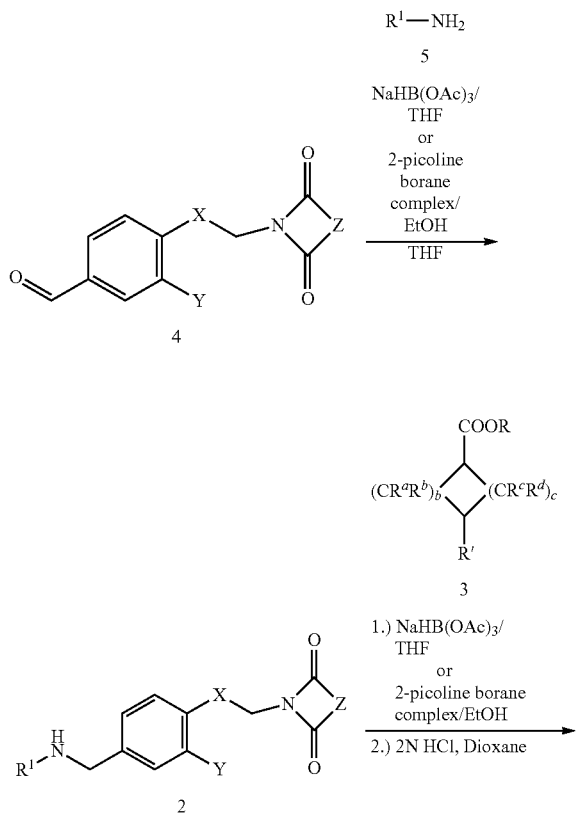

As mentioned above the compounds of formula 1 or a pharmaceutically acceptable salt, stereoisomer or a pharmaceutically acceptable salt of the stereoisomer can be used as active ingredient of a medicament in the preventive and/or therapeutic treatment of a CXCR3 receptor mediated disease or disorder, especially of a disease or disorder selected from the group consisting of COPD, psoriasis, graft/transplant rejection, ophthalmological disease, celiac disease, inflammatory bowel disease (IBD), type 1 diabetes, myasthenia gravis (MG), multiple sclerosis (MS) and other neuroinflammatory diseases, lupus, rheumatoid arthritis (RA) or lichen planus.

As the active ingredient of the medicament of the present invention, a substance may be used which is selected from the group consisting of the compound represented by the aforementioned formula 1 and pharmacologically acceptable salts, or stereoisomer thereof or a pharmaceutically acceptable salt of the stereoisomer. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

The present invention will be explained more specifically with reference to the following examples, however, the scope of the present invention is not limited to these examples.

Unless otherwise stated, the following abbreviations have the stated meanings in the examples below:

abs.=absolute
AcOH=Acetic acid
$[(C_6H_5)_3P]_2PdCl_2$=Bis(triphenylphosphine)palladium(II) dichloride
cc. HCl=concentrated hydrogen chloride solution
CuI=copper1 iodide
DCM=dichloromethane
Diazald=N-methyl-N-nitroso-p-toluenesulfonamide
DMF=N,N-dimethylformamide
equiv.=equivalent
Et=ethyl
EtOH=ethanol
$Et_2O$=diethyl ether
EtOAc=ethyl acetate
HCCOH=formic acid
HPLC=high performance liquid chromatography
Ipam=isopropyl amine
$K_2CO_3$=potassium carbonate
$K_3PO_4$=potassium phosphate
KBr=potassium bromide
KOH=potassium hydroxide
LC/MS=liquid chromatography—mass spectrometry
MEK=methyl-ethyl ketone
Me=methyl
MeOH=methanol
$NaHCO_3$=sodium bicarbonate
$Na_2SO_4$=sodium sulfate
$NaBH(OAc)_3$=sodium triacetoxy borohydride
nM=nanomole
NaOH=sodium hydroxide
NMR=nuclear magnetic spectroscopy
$Pd(OAc)_2$=palladium(II) acetate
r.t.=room temperature
TBAB=tetrabutylammonium bromide
TEA=triethylamine
THF=tetrahydrofuran
TsOH=p-toluenesulfonic acid monohydrate Analytical LC/MS is performed using Waters Alliance 2695+2996 PDA at 220 nm.

A system) MS: Waters LCT Premier XE; Column: Atlantis dC18 (3 µm) 2.1×50 mm; flow 0.7 ml/min of acetonitrile/water/0.05% TFA gradient in ESI+ mode B system) MS: Micromass ZQ; Column: Purospher-STAR RP18e (3 µm) 4.6×55 mm; flow 1.6 ml/min of water/acetonitrile/20 mM $NH_4OH$ gradient or Xterra MS-C18 (3.5 µM) 2.1×50 mm; flow: 1.0 ml/min of water/acetonitrile/20 mM $NH_4OH$ gradient in ESI+ mode.

Preparative chiral HPLC is performed using Berger Prep SFC at 210 nm;

C system) Column: Chiralpack IC 250×21 mm (5 µm) Flow: 50 ml/min; CO2/[Ethanol/+0.5% Ipam] 60%/40% (other circumstances are detailed in examples).

For structural confirmation NMR spectra are measured for all compounds as well. The NMR spectra are recorded on a Bruker Advance II 400 MHz spectrometer at ambient temperature in DMSO-$d_6$ solution. The chemical shifts are referred to tetramethylsilane (6, ppm). In some cases not only $^1H$ but $^{13}C$, ed-HSQC, zqs-TOCSY and HMBC spectra are also recorded.

Precursor Preparations

Intermediate 4.1 4-[2-(2,5-Dioxo-pyrrolidin-1-yl)-ethoxy]-3-methoxy-benzaldehyde A Method:

6.85 g (45 mmol) of vanillin (6.1) and 10.2 g (49.5 mmol) 1-(2-bromo-ethyl)-pyrrolidine-2,5-dione (7.1) is heated with 8.28 g (60 mmol) $K_2CO_3$ in 200 ml of acetonitrile under reflux for 15 h. Precipitated KBr is filtered off, the filtrate is evaporated, the residue is dissolved in 200 ml of dichloromethane, washed with water and 2N NaOH solution, dried with $Na_2SO_4$ and evaporated. The remaining oil is triturated with n-hexane to result the desired 4.1 in white crystals. Yield: 6.88 g (55%). $(M+H)^+=278$, $R_t$ (A)=1.90 min, purity 97.6%.

$^1$H-NMR: 2.64 (s, 4H), 3.77 (t, 2H), 2.75 (s, 3H), 4.21 (t, 3H), 7.17 (d, 1H), 7.40 (d, 1H), 7.53 (dd, 1H), 9.84 (s, 1H).

B Method:

11.66 g (45 mmol) of 4-(2-bromo-ethoxy)-3-methoxy-benzaldehyde (6.2) and 4.46 g (45 mmol) pyrrolidine-2,5-dione (7.2) is heated with 8.28 g (60 mmol) $K_2CO_3$ in 200 ml of acetonitrile for 8 h. After same isolation procedure as in A method 4.1 is given with same purity.

Following the procedure as outlined for intermediate 4.1, the intermediates of general formula 4a listed in Table 1 are prepared.

TABLE 1

| Intermediate | Structure | $(M + H)^+$ | $R_t$ min. (system) | Purity (%) |
|---|---|---|---|---|
| 4.2 | 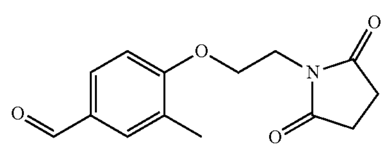 [SMILES: Cc1cc(C=O)ccc1OCCN1C(=O)CCC1=O] | 262 | 2.25 (A) | 98.2 |
| 4.3 | 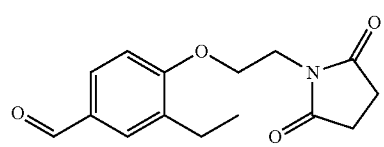 [SMILES: CCc1cc(C=O)ccc1OCCN1C(=O)CCC1=O] | 276 | 2.45 (A) | 98.3 |
| 4.4 | 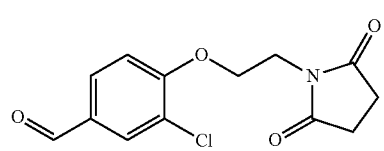 [SMILES: O=Cc1ccc(OCCN2C(=O)CCC2=O)c(Cl)c1] | 282 | 2.26 (A) | 98.3 |
| 4.5 | 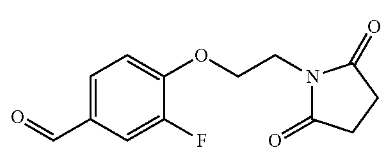 [SMILES: O=Cc1ccc(OCCN2C(=O)CCC2=O)c(F)c1] | 266 | 3.36 (B) | 99.3 |

TABLE 1-continued

| Intermediate | Structure | (M + H)+ | R_t min. (system) | Purity (%) |
|---|---|---|---|---|
| 4.6 | 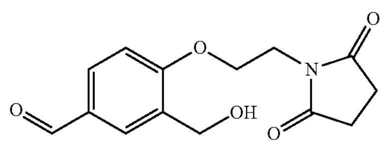 [SMILES: O=Cc1ccc(OCCN2C(=O)CCC2=O)c(CO)c1] | 278 | 1.69 (A) | 86.7 |
| 4.7 | 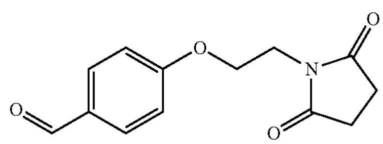 [SMILES: O=Cc1ccc(OCCN2C(=O)CCC2=O)cc1] | 248 | 1.98 (A) | 95.9 |
| 4.8 | 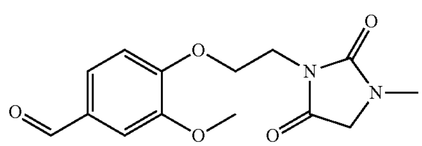 [SMILES: COc1cc(C=O)ccc1OCCN1C(=O)CN(C)C1=O] | 293 | 1.86 (A) | 98.7 |
| 4.9 | 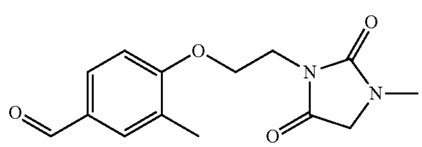 [SMILES: Cc1cc(C=O)ccc1OCCN1C(=O)CN(C)C1=O] | 277 | 2.28 (A) | 98.3 |
| 4.10 | 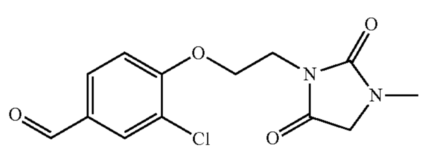 [SMILES: CN1CC(=O)N(CCOc2ccc(C=O)cc2Cl)C1=O] | 297 | 2.19 (A) | 95.3 |
| 4.11 | 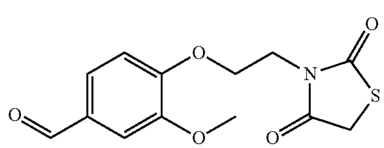 [SMILES: COc1cc(C=O)ccc1OCCN1C(=O)CSC1=O] | 296 | 2.32 (A) | 86.1 |
| 4.12 | 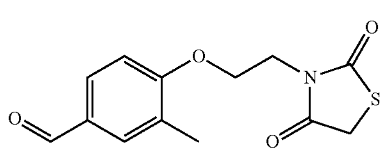 [SMILES: Cc1cc(C=O)ccc1OCCN1C(=O)CSC1=O] | 280 | 2.67 (A) | 93.7 |
| 4.13 | 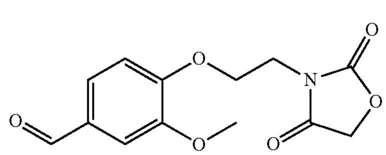 [SMILES: COc1cc(C=O)ccc1OCCN1C(=O)COC1=O] | 280 | 2.05 (A) | 91.7 |
| 4.14 | 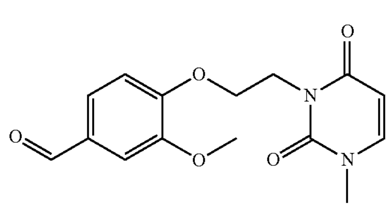 [SMILES: COc1cc(C=O)ccc1OCCn1c(=O)ccn(C)c1=O] | 305 | 2.08 (A) | 97.9 |

TABLE 1-continued

| Intermediate | Structure | (M + H)+ | R_t min. (system) | Purity (%) |
|---|---|---|---|---|
| 4.15 | 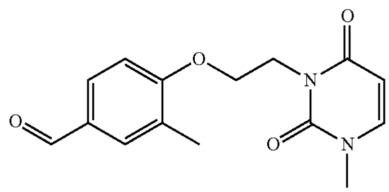 [SMILES: Cc1cc(C=O)ccc1OCCn1c(=O)ccn(C)c1=O] | 289 | 2.35 (A) | 99.6 |
| 4.16 | 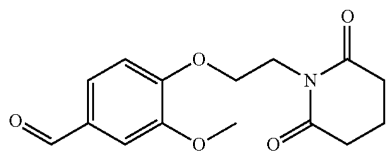 [SMILES: COc1cc(C=O)ccc1OCCN1C(=O)CCCC1=O] | 292 | 2.22 (A) | 88.2 |
| 4.17 | 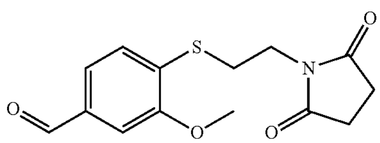 [SMILES: COc1cc(C=O)ccc1SCCN1C(=O)CCC1=O] | 294 | 2.34 (A) | 97.2 |
| 4.28 | 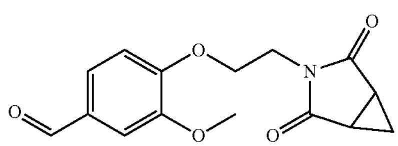 [SMILES: COc1cc(C=O)ccc1OCCN1C(=O)C2CC2C1=O] | 290 | 2.07 (A) | 94.0 |
| 4.29 | 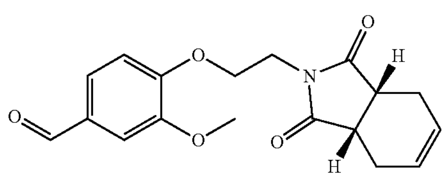 [SMILES: COc1cc(C=O)ccc1OCCN1C(=O)[C@H]2CC=CC[C@H]2C1=O] | 330 | 2.78 (A) | 98.0 |
| 4.30 | 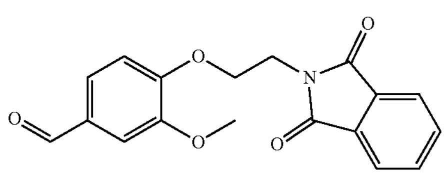 [SMILES: COc1cc(C=O)ccc1OCCN1C(=O)c2ccccc2C1=O] | 326 | 3.06 (A) | 99.0 |
| 4.32 | 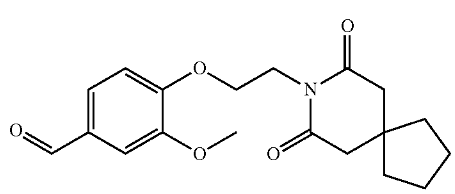 [SMILES: COc1cc(C=O)ccc1OCCN1C(=O)CC2(CCCC2)CC1=O] | 346 | 2.86 (A) | 99.3 |

Intermediate 4.18 4-[(E)-3-(2,5-Dioxo-pyrrolidin-1-yl)-propenyl]-3-methoxy-benzaldehyde

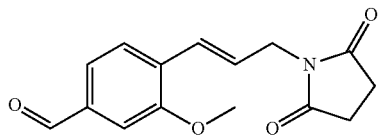 [SMILES: COc1cc(C=O)ccc1/C=C/CN1C(=O)CCC1=O]

Step 1:

6.85 g (45 mmol) vanillin (6.1) is cooled in a 100 ml of a mixture of DCM-pyridine 4:1, then 9.1 ml (54 mmol) of trifluoromethanesulfonic anhydride in 10 ml DCM is dropped in. The mixture is stirred at r.t. for 2 hours, after evaporated and the residue is triturated with 3×10 ml of EtOAc, the collected organic layer is dried and evaporated. The crude material (6.1a) is used for next step without further purification.

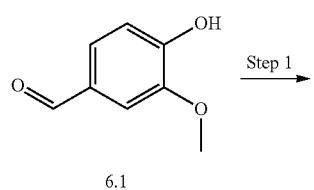

6.1

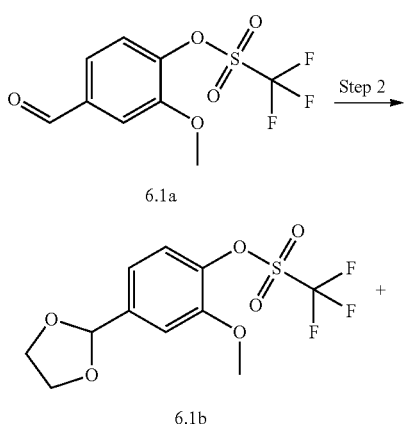

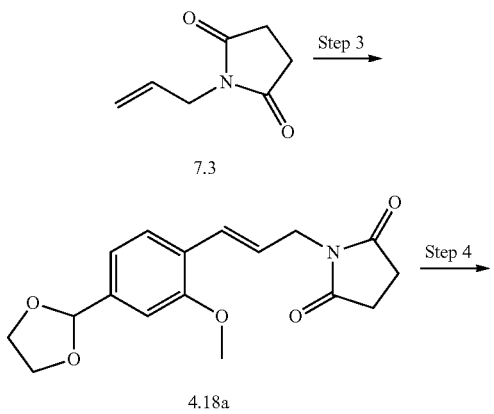

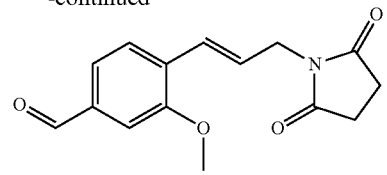

Intermediate 4.18

Step 2:

The formed crude trifluoro-methanesulfonic acid 4-formyl-2-methoxy-phenyl ester (6.1a), 2.52 ml (45 mmol) of ethylene glycol and 0.77 g (4.5 mmol) TsOH are refluxed in 180 ml of benzene. After evaporation the residue is purified by column chromatography. The desired intermediate is 11 g (80%) of trifluoro-methanesulfonic acid 4-[1,3]dioxolan-2-yl-2-methoxy-phenyl ester (6.1b), as a yellow oil. (M+H)$^+$=329, R$_t$ (A)=3.44 min, purity 93.4%.

Step 3:

A mixture of 1.76 g (5 mmol) triflate (6.1a), 2.1 g (15 mmol) of 1-allyl-pyrrolidine-2,5-dione (7.3; *Bull. Chem. Soc. Japan,* 1984, 57(10), 3021), 0.067 g (0.3 mmol) of Pd(OAc)$_2$, 0.373 g (5 mmol) KCl, 3.22 g (10 mmol) TBAB and 2.12 g (10 mmol) K$_3$PO$_4$ is heated in 10 ml DMF under nitrogen at 120° C. for 8 h. The mixture is diluted with water, extracted with 3×50 ml of EtOAc, the collected organic phase is evaporated and purified by column chromatography (EtOAc-n-hexane 1:1). The desired intermediate (4.18a) is 1.8 g of 1-[(E)-3-(4-[1,3]dioxolan-2-yl-2-methoxy-phenyl)-allyl]-pyrrolidine-2,5-dione, as an oil. (M+H)$^+$=318, R$_t$ (A)=2.58 min, R$_t$ (B)=4.15 min, purity 71%.

Step 4:

1.8 g (4 mmol) of protected aldehyde (4.18a) and 5 ml (30 mmol) of cc. HCl in 15 ml of dioxane are stirred at r.t. for 3 h. After evaporation and purification by flash chromatography the desired 4-[(E)-3-(2,5-dioxo-pyrrolidin-1-yl)-propenyl]-3-methoxy-benzaldehyde (Intermediate 4.18) is 0.5 g (46%) as an oil. (M+H)$^+$=274, R$_t$=2.56 min (A), purity 91.2%.

$^1$H-NMR: 2.67 (s, 4H), 3.90 (s, 3H), 4.16 (d, 2H), 6.37 (dt, 1H), 6.79 (d, 1H), 7.47-7.50 (m, 2H), 7.67 (d, 1H), 9.95 (s, 1H).

Intermediate 4.19 4-[3-(2,5-Dioxo-pyrrolidin-1-yl)-prop-1-ynyl]-3-methoxy-benzaldehyde

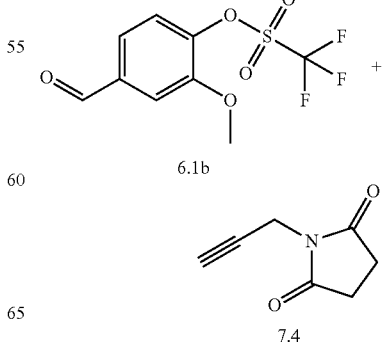

-continued

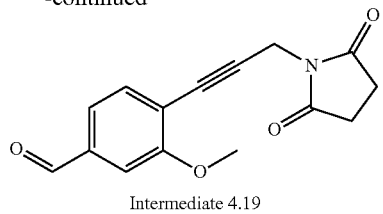
Intermediate 4.19

A mixture of 4.26 g (15 mmol) triflate (6.1b), 2.47 g (18 mmol) of 1-prop-2-ynyl-pyrrolidine-2,5-dione (7.4), 0.067 g (0.3 mmol) of [$(C_6H_5)_3P]_2PdCl_2$, 0.143 g (0.75 mmol) CuI, 0.32 g (0.75 mmol) of 1,4-bis(diphenyl-phosphino)butane and 7 ml (50.5 mmol) of TEA in 40 ml DMF under nitrogen at 100° C. for 3 h. The inorganic salts are removed and DMF is evaporated. The residue is treated with water, extracted 3×50 ml of EtOAc, the collected organic phase is evaporated and purified by flash chromatography (toluene-MeOH 9:1). The desired intermediate 4.19 is 1.9 g (44%) of 4-[3-(2,5-dioxo-pyrrolidin-1-yl)-prop-1-ynyl]-3-methoxy-benzaldehyde, as a dark yellow solid. (M+H)$^+$=272, R$_t$=2.15 min (A), purity: 98.9%.

$^1$H-NMR: 2.71 (s, 4H), 3.89 (s, 3H), 4.44 (s, 2H), 7.47-7.50 (m, 2H), 7.55 (d, 1H), 9.98 (s, 1H).

Following procedures outlined for intermediate 4.19 the intermediates of general formula 4b listed in Table 2 are prepared.

TABLE 2

| Intermediate | Structure | (M + H)$^+$ | R$_t$ min (system) | Purity (%) |
|---|---|---|---|---|
| 4.20 | 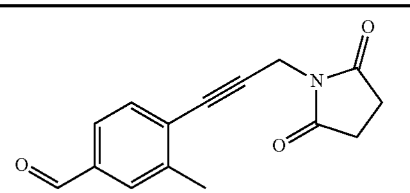 | 256 | 2.60 (A) | 94.8 |
| 4.21 | 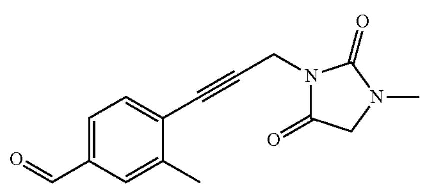 [SMILES: Cc1cc(C=O)ccc1C#CCN1C(=O)CN(C)C1=O] | 271 | 2.40 (A) | 96.7 |
| 4.22 | 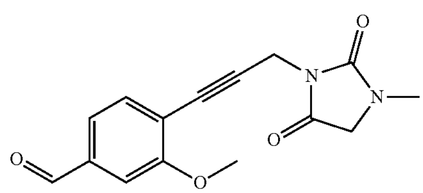 [SMILES: COc1cc(C=O)ccc1C#CCN1C(=O)CN(C)C1=O] | 287 | 1.98 (A) | 95.3 |

Intermediate 4.23 4-[3-(2,5-Dioxo-pyrrolidin-1-yl)-propyl]-3-methoxy-benzaldehyde

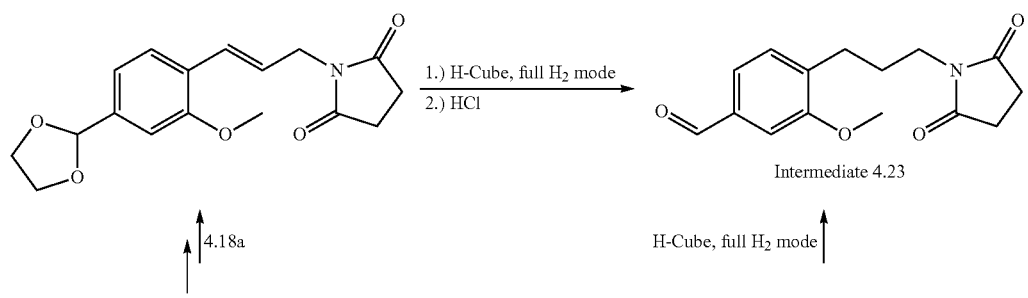

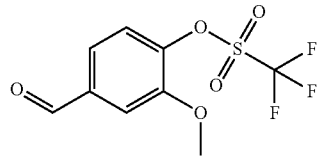

6.1b

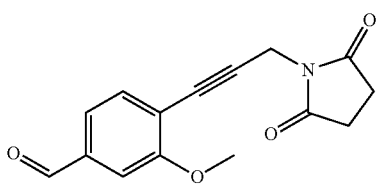

Intermediate 4.19

A Method:

Using 3.02 g (9.2 mmol) of triflate (6.1b) a crude protected allyl derivative (4.18a) is formed (as described in step 2 and 3 of Intermediate 4.18), which is hydrogenated by H-Cube equipment in full-H$_2$ mode in EtOAc. After evaporation the residue is dissolved in 50 ml of dioxane and stirred with 10 ml of cc. HCl at r.t. for 0.5 h. The mixture is evaporated, the residue is diluted with water, extracted with ethyl acetate, dried and removed the solvent. The crude material is purified by flash chromatography. The desired product (Intermediate 4.23) is 1.65 g (65.3%). (M+H)$^+$=276, R$_t$=2.57 min (A), purity: 97.7%.

$^1$H-NMR: 1.75 (qv, 2H), 2.59-2.62 (m, 6H), 3.38 (t, 2H), 3.86 (s, 3H), 7.40 (d, 2H), 7.47 (dd, 1H), 9.94 (s, 1H).

B Method:

Hydrogenation of 4-[3-(2,5-Dioxo-pyrrolidin-1-yl)-prop-1-ynyl]-3-methoxy-benzaldehyde (Intermediate 4.19) in same circumstances as described in A method is resulted Intermediate 4.23 in one step. The yield and purity is same as in A method.

Following procedures outlined for intermediate 4.23 the intermediate compounds of general formula 4c listed in Table 3 are prepared.

Intermediate 4.27 4-[2-(2,5-Dioxo-pyrrolidin-1-ylmethyl)-cyclopropyl]-3-methoxy-benzaldehyde

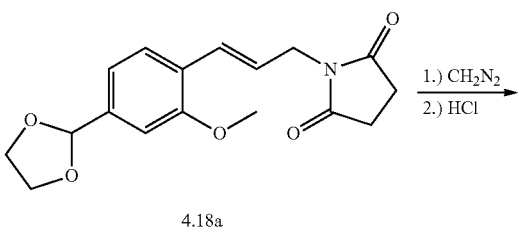

4.18a

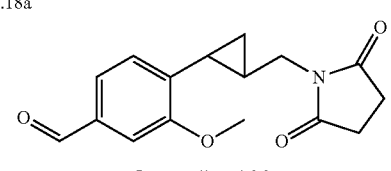

Intermediate 4.26

Diazomethane is generated with a diazomethane-generating kit (Aldrich): a solution of 3.846 g (17.9 mmol) of Diazald in 24 ml of Et$_2$O is added drop wise to a mixture of 3.018 g (53.78 mmol) of KOH in 18 ml of water, 4 ml of diethyl ether and 18 ml of 2-(2-ethoxyethoxy)-ethanol at 70° C. The ethe-

TABLE 3

| Intermediate | Structure | (M + H)$^+$ | Rt min. (system) | Purity (%) |
|---|---|---|---|---|
| 4.24 | 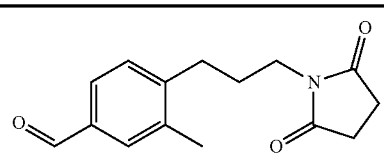 | 260 | 2.60 (A) | 96.0 |
| 4.25 | 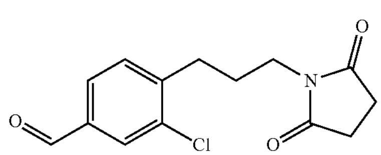 [SMILES: O=Cc1ccc(CCCN2C(=O)CCC2=O)c(Cl)c1] | 280 | 2.58 (A) | 96.2 |
| 4.26 | | 291 | 2.31 (A) | 86.0 | real solution of diazomethane is continuously distilled into a stirred solution of 575 mg (1.81 mmol) of protected aldehydes (4.18a; as described in step 3 of Intermediate 4.19) and 3.6 mg (0.016 mmol) Pd(OAc)$_2$ in a mixture of DCM and Et$_2$O (28 ml/20 ml) kept at 70° C. After the addition of diazomethane is complete the solution is stirred at r.t. for 30 min. The excess of diazomethane is quenched with AcOH. The resulted mixture is washed with AcOH, saturated Na$_2$CO$_3$ solution, dried and evaporated. The yield is 514 (95%) mg of titled compound. (M+H)$^+$=276, R$_t$=2.58 min (A), purity: 99.9%,

EXAMPLES

Example 1 trans-4-[([1-(2,3-Dihydro-1-benzofuran-5-yl)ethyl]{4-[2-(2,5-dioxo-pyrrolidin-1-yl)ethoxy]-3-methoxybenzyl}amino)methyl]cyclohexanecarboxylic acid

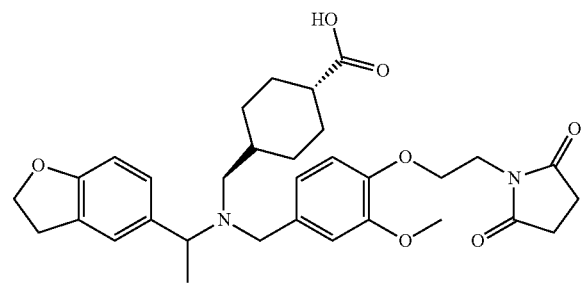

Step 1:

3.59 g (22 mmol) of 1-(2,3-dihydro-benzofuran-5-yl)-ethylamine (5.1), 5.54 g (20 mmol) of intermediate 4.1 and 1.60 ml (28 mmol) of AcOH are dissolved in 200 mL of THF, then 12.7 g (60 mmol) of NaHB(OAc)$_3$ is added in small portions into the solution at room temperature. The formed suspension is stirred overnight, and then diluted with 200 ml of EtOAc and 400 mL of water. After separation the aqueous phase is washed EtOAc, the combined organic phase is dried and evaporated. The crude oil is purified with flash chromatography (up 10% MeOH in DCM). The intermediate (2.1) is 7.05 g pale yellow oil (83%); (M+H)$^+$=425, R$_t$=2.1 min (A), purity: 96.4%.

Salt Formation:

118 mg (0.28 mmol) of 2.1 and 100 mg (0.28 mmol) of 1.5-naphthalenedisulfonic acid tetrahydrate is dissolved in 2 ml of EtOH, then evaporated, the residue is treated with Et$_2$O and the formed white solid filtrated, and washed with Et$_2$O. Yield is 80 mg (48%) 2.1 with 0.6 moles 1,5-naphthalenedisulfonic acid. (M+H)$^+$=425, R$_t$=2.1 min (A), purity: 98.6%.

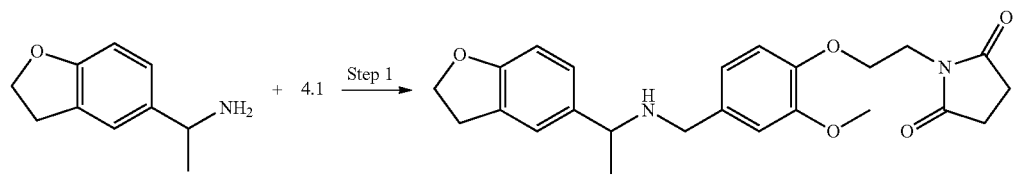

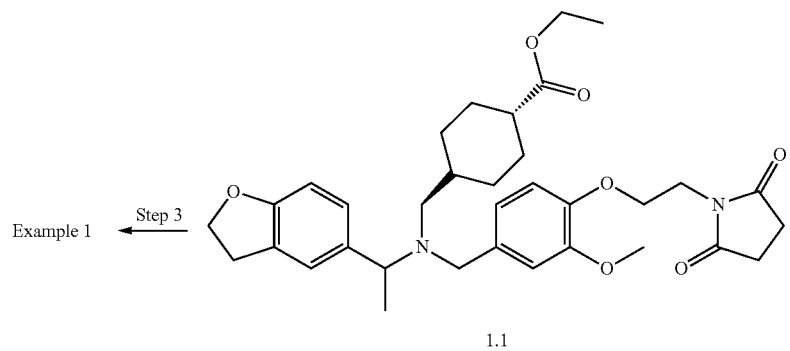

Step 2:

950 mg (2.24 mmol) of free amine (2.1) and 1.14 g (6.72 mmol) of trans-4-formyl-cyclohexanecarboxylic acid ethyl ester (3.1) are dissolved in THF and 0.19 mL (3.36 mmol) of AcOH is added followed by the addition 2.37 g (11.19 mmol) of NaHB(OAc)$_3$ and the reaction is stirred overnight at room temperature. Then the reaction is diluted EtOAc (75 ml) and water (50 ml) and 2 ml 1N HCl is added. The aqueous phase is separated, the organic phase is extracted two times with the same amounts of water and 1N HCl solution. The aqueous phases are combined, the pH adjusted to 8-9 by the addition of 1N NaOH and extracted two times with EtOAc. The combined organic phase is washed with brine, dried and evaporated. The crude product is used for next step without purification. Yield is 1.21 g of 1.1 (93.4%) as an oil. (M+H)$^+$=593; R$_t$=2.78 min (A), purity: 91.1%.

Salt Formation:

250 mg (0.44 mmol) of 1.1 is dissolved 1 ml of THF and acidified with HCl in Et$_2$O. The precipitated HCl salt is filtrated, washed Et$_2$O and dried. Yield is 185 mg (66.4%) as a white foam. (M+H)$^+$=593; R$_t$=2.78 min (A), purity 93.3%.

Step 3:

1.21 g (2.1 mmol) of ester (1.1) is dissolved in 5 ml of dioxane, 5.23 ml (10.5 mmol) of 2N HCl is added in and the mixture was stirred at 60° C. for 3 hours. Then the mixture is diluted with water, the pH value is adjusted to 7 with 1N NaOH and the aqueous phase is extracted 3 times with DCM. Organic phases were combined, dried and evaporated. The title compound is isolated as a white foam after HPLC purification using 4% MeOH in DCM. Yield 615 mg (52%); Molecular Formula=C$_{32}$H$_{40}$N$_2$O$_7$; (M+H)$^+$=565, R$_t$=2.35 min (A), purity 98.1%.

$^1$H-NMR: 0.6 (dddd, 1H), 0.7 (dddd, 1H), 1.23 (ddd, 2H), 1.28 (d, 3H), 1.4 (br, 1H), 1.82 (d, 1H), 1.83 (d, 1H), 1.84 (d, 1H), 1.85 (d, 1H), 2.00 (dd, 1H), 2.04 (dddd, 1H), 2.25 (dd, 1H), 2.63 (s, 4H), 3.16 (t, 2H), 3.27 (d, 1H), 3.42 (d, 1H), 3.70 (t, 2H), 3.71 (s, 3H), 3.79 (q, 1H), 4.03 (t, 2H), 4.49 (t, 2H), 6.70 (d, 1H), 6.78 (dd, 1H), 6.84 (d, 1H), 6.90 (d, 1H), 7.04 (dd, 1H), 7.20 (d, 1H), 11.90 (s, 1H).

Example 2 cis-4-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid

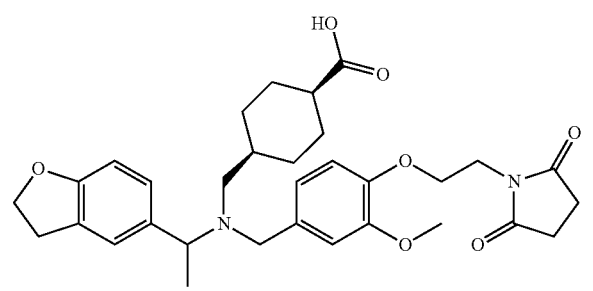 [SMILES: COc1cc(CN(C[C@H]2CC[C@@H](C(=O)O)CC2)C(C)c2ccc3c(c2)CCO3)ccc1OCCN1C(=O)CCC1=O]

Step 1:

is undertaking as in Example 1, step 2 is accomplished with cis-4-formyl-cyclohexanecarboxylic acid methyl ester (3.2) in same conditions, after acidic hydrolysis and purification the title compound is isolated as a white foam. Molecular Formula=C$_{32}$H$_{40}$N$_2$O$_7$; (M+H)$^+$=565; R$_t$=2.45 min (A), purity 99.5%.

$^1$H-NMR: 1.05-1.07 (m, 2H), 1.28 (d, 3H), 1.36-1.38 (m, 3H), 1.55 (m, 3H), 1.68 (m, 1H), 2.07 (dd, 1H), 2.25 (dd, 1H), 2.35 (qi, 1H), 2.63 (s, 4H), 3.15 (t, 2H), 3.28 (d, 1H), 3.42 (d, 1H), 3.70 (t, 2H), 3.71 (s, 3H), 3.78 (q, 1H), 4.02 (t, 2H), 4.49 (t, 2H), 6.69 (d, 1H), 6.78 (dd, 1H), 6.86 (d, 1H), 6.90 (d, 1H), 7.03 (dd, 1H), 7.20 (d, 1H), 11.89 (s, 1H).

Example 3 trans-4-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid

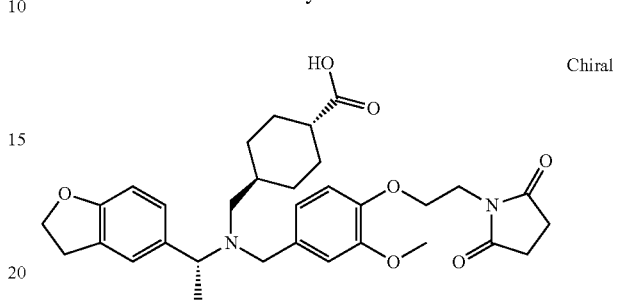

611 mg of Example 1 is separated by preparative chiral column chromatography. The first eluted enantiomer has (R)-configuration, yield is 290 mg (95%). (M+H)$^+$=565, R$_t$=11.0 min. (C), purity: 98.1%.

Example 4 trans-4-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid

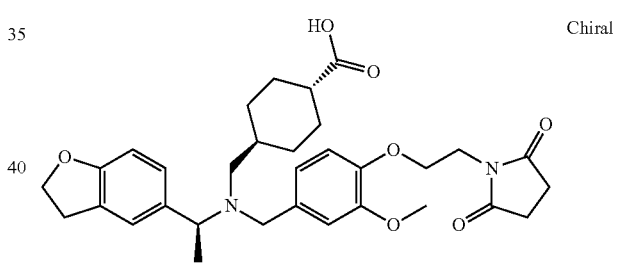

611 mg of Example 1 is separated by preparative chiral column chromatography. The second eluted enantiomer has (S)-configuration, yield is 240 mg (79%). (M+H)$^+$=565, R$_t$=12.2 min (C), purity: 99.2%.

Example 5 trans-4-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclohexanecarboxylic acid

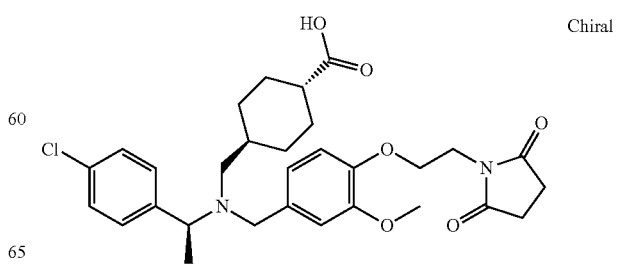

Step 1 is undertaking as in Example 1 using (S)-1-(4-chloro-phenyl)-ethylamine (5.2), further steps are occurred analogously as in Example 1 and the desired compound is resulted. (M+H)⁺=557, $R_t$=2.51 min (A), purity: 97.6%.

Example 6 trans-4-[([(R)-1-(4-Chloro-phenyl)-ethyl]-{4-[2-(2,5-dioxo-pyrrolidin-1-yl)-ethoxy]-3-methoxy-benzyl}-amino)-methyl]-cyclohexanecarboxylic acid

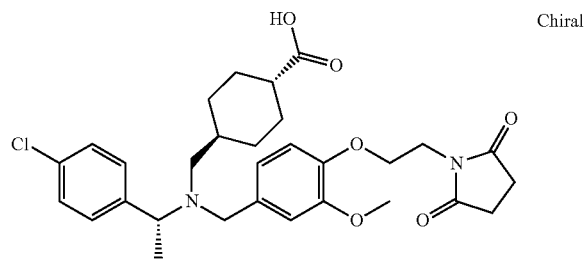 [SMILES: COc1cc(CN(C[C@H]2CC[C@H](C(=O)O)CC2)[C@H](C)c2ccc(Cl)cc2)ccc1OCCN1C(=O)CCC1=O]

Step 1 is undertaking as in Example 5 using (R)-1-(4-chloro-phenyl)-ethylamine (5.3), further steps are occurred analogously as in Example 1 and the desired compound is resulted. (M+H)⁺=557, $R_t$=2.59 min (A), purity: 96.8%.

Example 7 trans-4-[([(S)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid

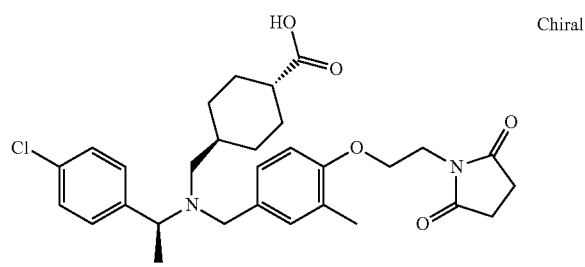 [SMILES: Cc1cc(CN(C[C@H]2CC[C@H](C(=O)O)CC2)[C@@H](C)c2ccc(Cl)cc2)ccc1OCCN1C(=O)CCC1=O]

Step 1 is undertaking as in Example 1 using (S)-1-(4-chloro-phenyl)-ethylamine (5.2) and Intermediate 4.2, further steps are occurred analogously as in Example 1 and the desired compound is resulted. (M+H)⁺=541, $R_t$=2.66 min (A), purity: 95.5%.

Example 8 cis-4-[([(S)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid

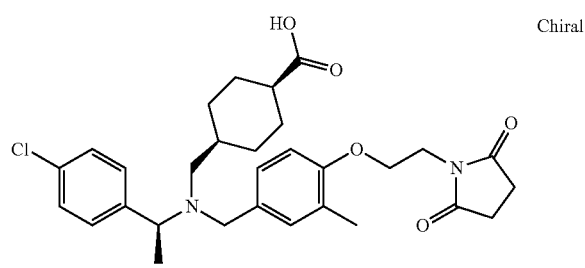 [SMILES: Cc1cc(CN(C[C@H]2CC[C@@H](C(=O)O)CC2)[C@@H](C)c2ccc(Cl)cc2)ccc1OCCN1C(=O)CCC1=O]

Step 1 is undertaking as in Example 7, step 2 is accomplished with cis-4-formyl-cyclohexanecarboxylic acid methyl ester (3.2) in same conditions, after acidic hydrolysis and purification the title compound is isolated. (M+H)⁺=541, $R_t$=2.64 min (A), purity 98.0%.

Example 9 trans-4-[([(R)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid

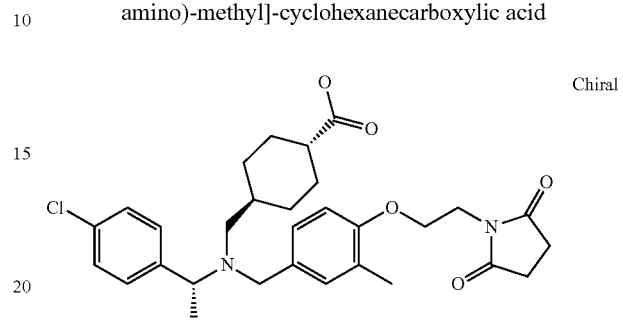

Step 1 is undertaking as in Example 6 using (R)-1-(4-chloro-phenyl)-ethylamine (5.3) and Intermediate 4.2, further steps are occurred analogously as in Example 6 and the desired compound is resulted. (M+H)⁺=541, $R_t$=2.61 min (A), purity: 96.8%.

Example 10 trans-4-[((5-Chloro-indan-1-yl)-{4-[2-(2,5-dioxo-pyrrolidin-1-yl)-ethoxy]-3-methoxy-benzyl}-amino)-methyl]-cyclohexane-carboxylic acid

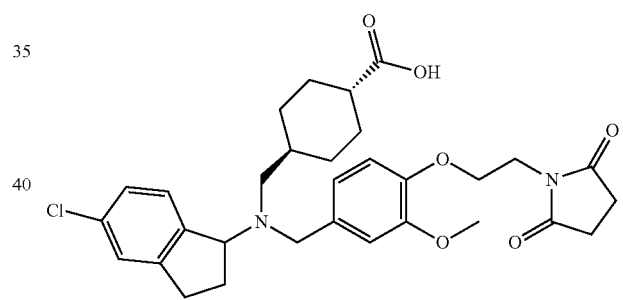

Following procedures outlined in Example 1 using 5-chloro-indan-1-ylamine (5.4) and Intermediate 4.1 in the first reductive amination step, the desired compound is resulted. (M+H)⁺=569, $R_t$=2.57 min (A), purity: 89.9%.

Example 11 trans-4-[(((R)-5-Chloro-indan-1-yl)-{4-[2-(2,5-dioxo-pyrrolidin-1-yl)-ethoxy]-3-methoxy-benzyl}-amino)-methyl]cyclohexanecarboxylic acid

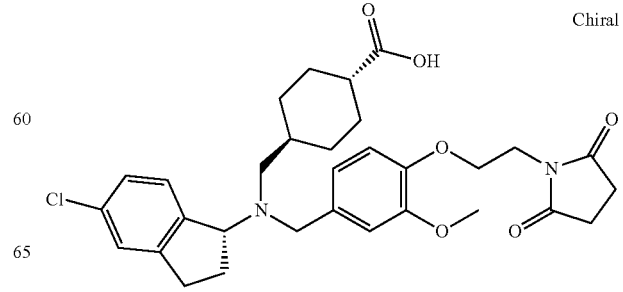

643 mg of Example 10 is separated by preparative chiral column chromatography. The first eluted enantiomer has (R)-configuration, yield is 250 mg (77.8%). (M+H)$^+$=569, R$_t$=6.6 min. (C), purity: 98.2%.

Example 12 trans-4-[(((S)-5-Chloro-indan-1-yl)-{4-[2-(2,5-di-oxo-pyrrolidin-1-yl)-ethoxy]-3-methoxy-benzyl}-amino)-methyl]-cyclohexanecarboxylic acid

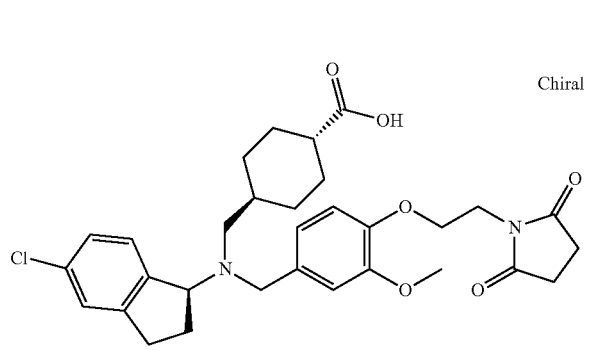 [SMILES: COc1cc(CN(C[C@H]2CC[C@H](C(=O)O)CC2)[C@H]2CCc3cc(Cl)ccc32)ccc1OCCN1C(=O)CCC1=O]

Method A:

Following chiral separation procedures outlined in Example 11 using 643 mg of Example 10, 270 mg (84%) of the titled compound is isolated as a second eluted material. (M+H)$^+$=569, R$_t$=9.0 min. (C), purity: 97.4%.

Method:

Following procedures outlined in Example 1 using 400 mg (2.39 mmol) of (S)-5-chloro-indan-1-ylamine (5.5) and 661 mg (2.39 mmol) of Intermediate 4.1 the titled compound is isolated: 652 mg (48%) (M+H)$^+$=569, R$_t$=2.69 min (A), purity 99.5%.

Example 13 cis-4-[((5-Chloro-indan-1-yl)-{4-[2-(2,5-dioxo-pyrrolidin-1-yl)-ethoxy]-3-methoxy-benzyl}-amino)-methyl]-cyclohexane-carboxylic acid

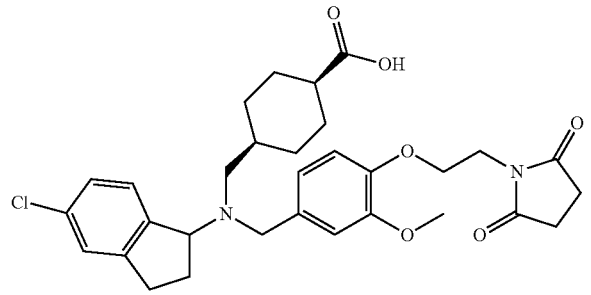 [SMILES: COc1cc(CN(C[C@H]2CC[C@@H](C(=O)O)CC2)C2CCc3cc(Cl)ccc32)ccc1OCCN1C(=O)CCC1=O]

Following procedures outlined in Example 2 using 5-chloro-indan-1-ylamine (5.4) and Intermediate 4.1 and 3.2 ester in reductive amination steps the desired compound is resulted. (M+H)$^+$=569, R$_t$=6.31 min (B), purity 85.6%.

Example 14 trans-4-[(((S)-4,5-Dichloro-indan-1-yl)-{4-[2-(2,5-dioxo-pyrrolidin-1-yl)-ethoxy]-3-methoxy-benzyl}-amino)-methyl]-cyclohexanecarboxylic acid hydrochloride Step 1 and 2:

3.70 g (15.5 mmol) of (S)-4,5-dichloro-indan-1-ylamine hydrochloride (5.6) is dissolved in DCM, washed with saturated sodium bicarbonate and brine, dried over sodium sulfate and evaporated at reduced pressure. The residue is dissolved in THF and placed into a water bath (bath temperature: 15° C.). 4.29 g (15.5 mmol) of Intermediate 4.1 is added followed by the addition of acetic acid (1.33 ml; 23.3 mmol). 8.21 g (38.7 mmol) of NaBH(OAc)$_3$ is added in four portions at 10 minutes intervals. Water bath is removed and the reaction is stirred one hour at room temperature. 2.63 g (15.5 mmol) of trans-4-formyl-cyclohexanecarboxylic acid methyl ester (3.3) is added and the reaction is stirred another hour at room temperature. Then the mixture is diluted with water, pH is adjusted to 7 by the addition of saturated NaHCO$_3$ and extracted with DCM three times. Organic phases are combined, dried over Na$_2$SO$_4$ and evaporated at reduced pressure. The residue is purified by silica gel flash chromatography using 50% EtOAc in hexane. Evaporation of pure fractions resulted in a pale yellow oil. Yield: 6.40 g (67%), (M+H)$^+$=317, R$_t$=2.91 min (A). Purity: 98.6%

Step 3:

6.40 g (10.4 mmol) of methyl ester is dissolved in 20 ml of dioxane. 25.9 ml (51.8 mmol) of 2N HCl solution is added and the reaction was stirred for 5 hours at 80° C. Then the mixture is diluted with water, pH is adjusted to 7 by the addition of saturated NaHCO$_3$ and extracted with DCM three times. Organic phases are combined, dried over sodium sulfate and evaporated at reduced pressure. The residue is purified by silica gel flash chromatography using a gradient of 3 to 6% of MeOH in DCM. Pure fractions are combined and evaporation resulted in a white solid foam of desired compound: 3.82 g (61.1%). (M+H)$^+$=603, R$_t$=2.66 min (A). Purity: 99.6%

Following the procedures as outlined in Example 1 using different amines (5), benzaldehydes (4) and formyl-cycloalkane carboxylic acid esters (3, R'=CHO) the compounds listed in Table 4 are prepared.

TABLE 4

| Examples | Structure | (M + H)+ | Rt min. (system) | Purity (%) |
|---|---|---|---|---|
| 15. | 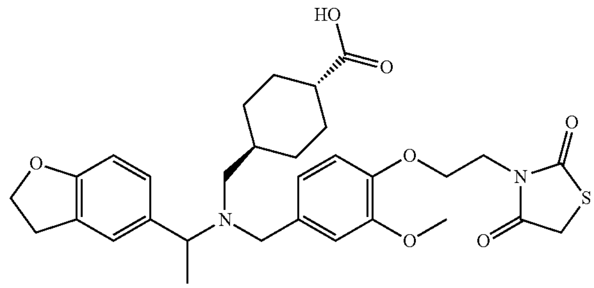 [SMILES: COc1cc(CN(C[C@H]2CC[C@H](C(=O)O)CC2)C(C)c2ccc3c(c2)CCO3)ccc1OCCN1C(=O)CSC1=O] | 583 | 2.53 (A) | 92.3 |
| 16. | 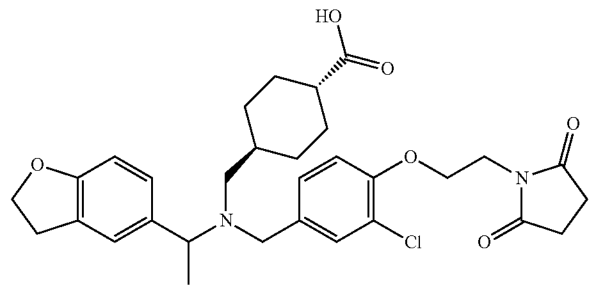 [SMILES: CC(c1ccc2c(c1)CCO2)N(Cc1ccc(OCCN2C(=O)CCC2=O)c(Cl)c1)C[C@H]1CC[C@H](C(=O)O)CC1] | 569 | 2.48 (A) | 97.8 |
| 17. | 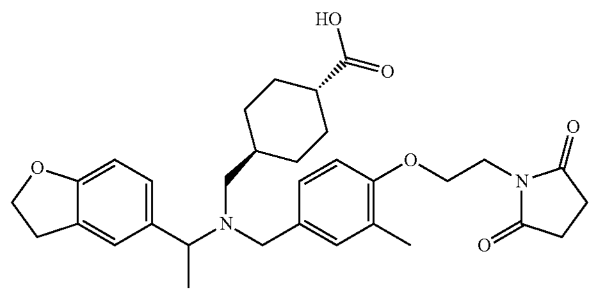 [SMILES: Cc1cc(CN(C[C@H]2CC[C@H](C(=O)O)CC2)C(C)c2ccc3c(c2)CCO3)ccc1OCCN1C(=O)CCC1=O] | 549 | 2.51 (A) | 92.8 |
| 18. | 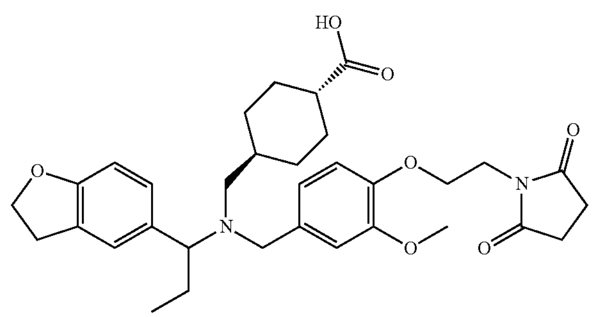 [SMILES: CCC(c1ccc2c(c1)CCO2)N(Cc1ccc(OCCN2C(=O)CCC2=O)c(OC)c1)C[C@H]1CC[C@H](C(=O)O)CC1] | 579 | 2.61 (A) | 89.3 |
| 19. | 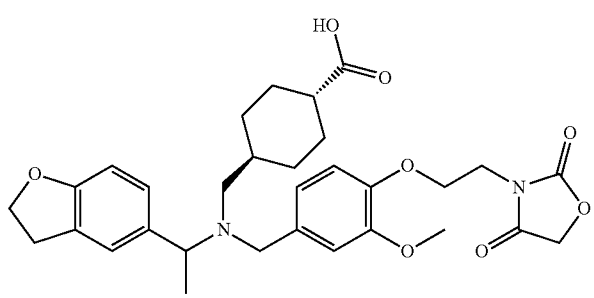 [SMILES: COc1cc(CN(C[C@H]2CC[C@H](C(=O)O)CC2)C(C)c2ccc3c(c2)CCO3)ccc1OCCN1C(=O)COC1=O] | 567 | 2.41 (A) | 97.9 |

TABLE 4-continued

| Examples | Structure | (M + H)+ | Rt min. (system) | Purity (%) |
|---|---|---|---|---|
| 20. | 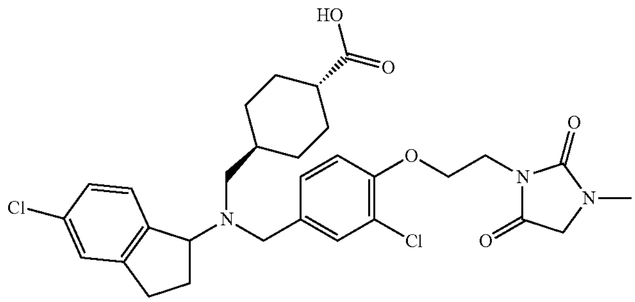 [SMILES: CN1CC(=O)N(CCOc2ccc(CN(C[C@H]3CC[C@H](C(=O)O)CC3)C3CCc4cc(Cl)ccc43)cc2Cl)C1=O] | 589 | 2.65 (A) | 96.9 |
| 21. | 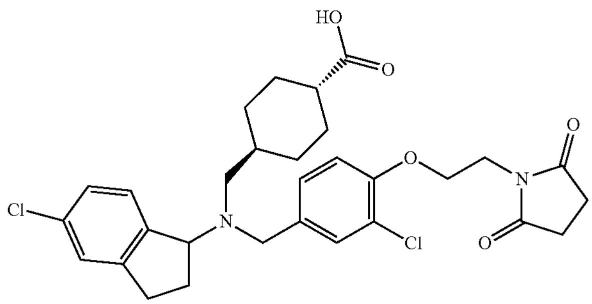 | 573 | 2.70 (A) | 92.0 |
| 22. | 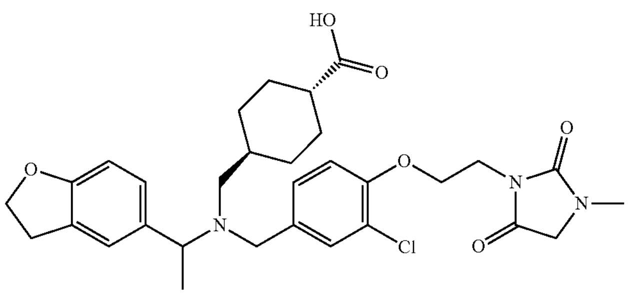 [SMILES: CC(c1ccc2c(c1)CCO2)N(Cc1ccc(OCCN2C(=O)CN(C)C2=O)c(Cl)c1)C[C@H]1CC[C@H](C(=O)O)CC1] | 584 | 2.42 (A) | 93.4 |
| 23. | Chiral | 576 | 2.58 (A) | 92.7 |
| 24. | 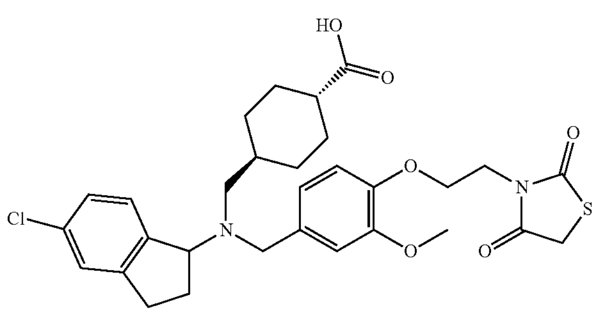 [SMILES: COc1cc(CN(C[C@H]2CC[C@H](C(=O)O)CC2)C2CCc3cc(Cl)ccc32)ccc1OCCN1C(=O)CSC1=O] | 587 | 2.74 (A) | 86.9 |

TABLE 4-continued

| Examples | Structure | (M + H)+ | Rt min. (system) | Purity (%) |
|---|---|---|---|---|
| 25. | 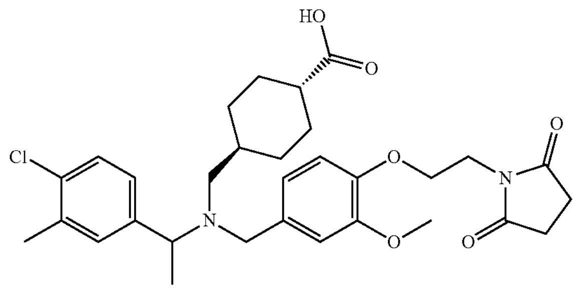 [SMILES: COc1cc(CN(C[C@H]2CC[C@H](C(=O)O)CC2)C(C)c2ccc(Cl)c(C)c2)ccc1OCCN1C(=O)CCC1=O] | 571 | 2.67 (A) | 95.6 |
| 26. | Chiral | 571 | 2.73 (A) | 94.5 |
| 27. | Chiral | 571 | 2.73 (A) | 94.9 |
| 28. | 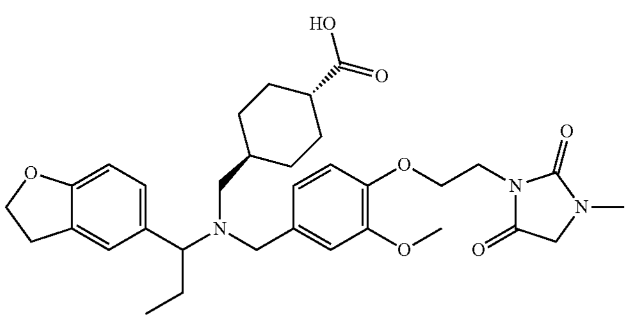 [SMILES: CCC(c1ccc2c(c1)CCO2)N(Cc1ccc(OCCN2C(=O)CN(C)C2=O)c(OC)c1)C[C@H]1CC[C@H](C(=O)O)CC1] | 594 | 2.47 (A) | 87.0 |
| 29. | 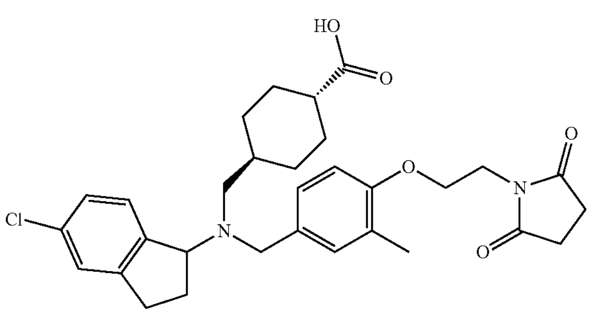 [SMILES: Cc1cc(CN(C[C@H]2CC[C@H](C(=O)O)CC2)C2CCc3cc(Cl)ccc32)ccc1OCCN1C(=O)CCC1=O] | 553 | 2.73 (A) | 97.6 |

TABLE 4-continued

| Examples | Structure | | (M + H)+ | Rt min. (system) | Purity (%) |
|---|---|---|---|---|---|
| 30. | 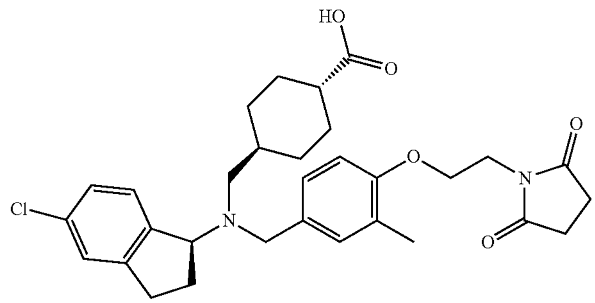 | Chiral | 553 | 5.4 (C) | 99.8 |
| 31. | 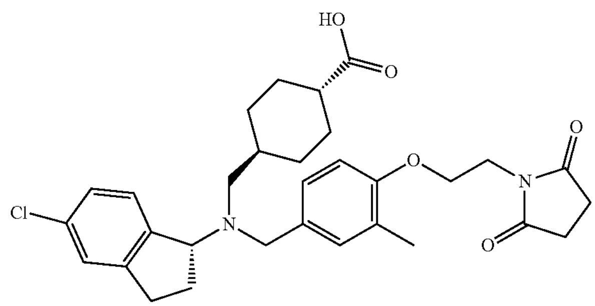 | Chiral | 553 | 7.1 (C) | 100 |
| 32. | 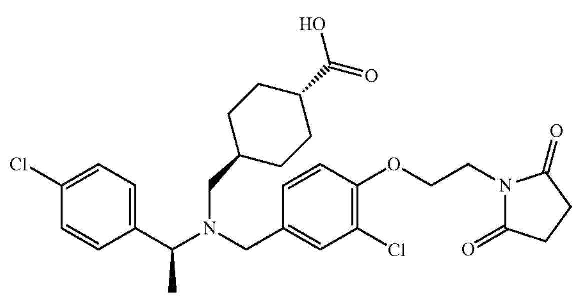 | Chiral | 561 | 2.63 (A) | 92.3 |
| 33. | 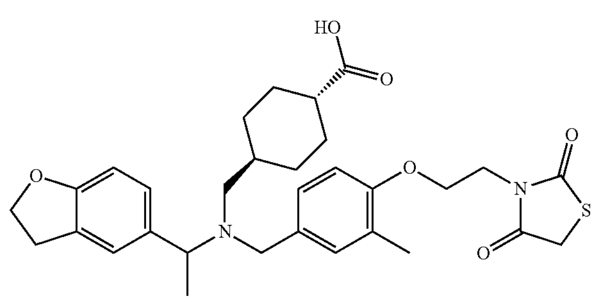 [SMILES: Cc1cc(CN(C[C@H]2CC[C@H](C(=O)O)CC2)C(C)c2ccc3c(c2)CCO3)ccc1OCCN1C(=O)CSC1=O] | | 567 | 2.72 (A) | 92.7 |

TABLE 4-continued
| Examples | Structure | | (M + H)+ | Rt min. (system) | Purity (%) |
|---|---|---|---|---|---|
| 34. | 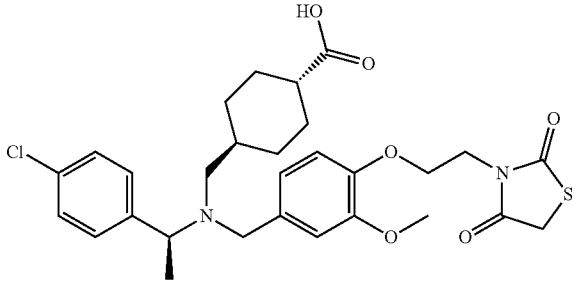 | Chiral | 575 | 2.80 (A) | 93.6 |
| 35. | 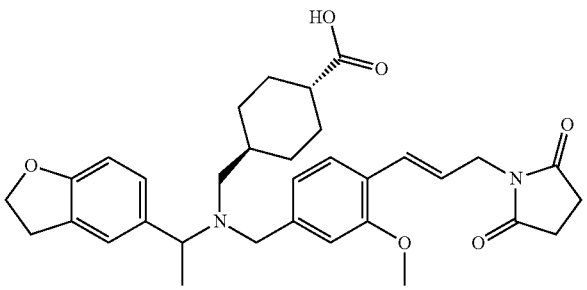 [SMILES: COc1cc(CN(C[C@H]2CC[C@H](C(=O)O)CC2)C(C)c2ccc3c(c2)CCO3)ccc1/C=C/CN1C(=O)CCC1=O] | | 561 | 2.61 (A) | 91.7 |
| 36. | 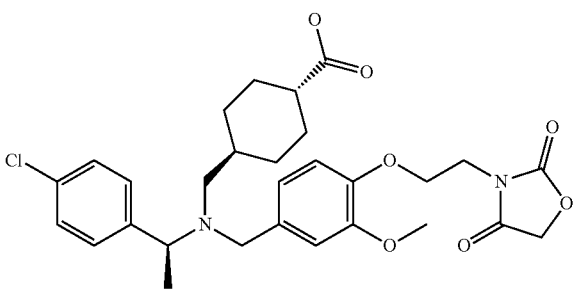 | Chiral | 559 | 2.63 (A) | 90.9 |
| 37. | 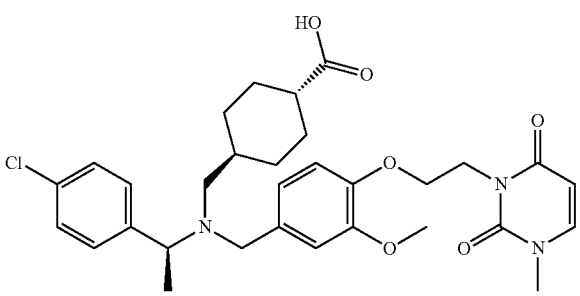 | Chiral | 584 | 2.53 (A) | 96.5 |
| 38. | 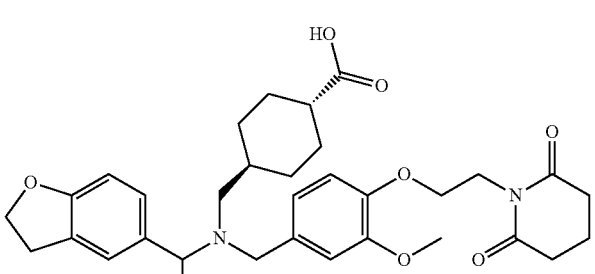 | | 579 | 2.50 (A) | 81.0 |

TABLE 4-continued

| Examples | Structure | (M + H)+ | Rt min. (system) | Purity (%) |
|---|---|---|---|---|
| 39. | Chiral | 556 | 2.68 (A) | 96.3 |
| 40. | 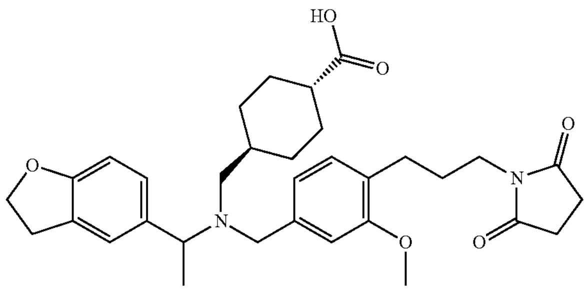 [SMILES: COc1cc(CN(C[C@H]2CC[C@H](C(=O)O)CC2)C(C)c2ccc3c(c2)CCO3)ccc1CCCN1C(=O)CCC1=O] | 550 | 2.74 (A) | 95.2 |
| 41. | 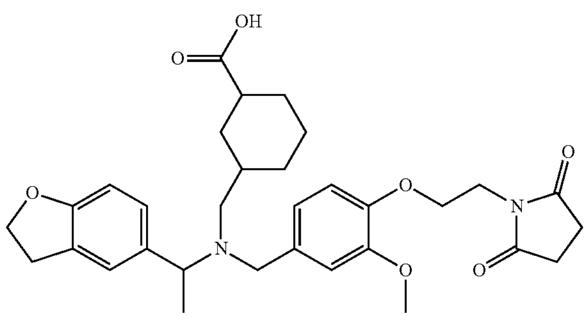 [SMILES: COc1cc(CN(CC2CCCC(C(=O)O)C2)C(C)c2ccc3c(c2)CCO3)ccc1OCCN1C(=O)CCC1=O] | 565 | 5.5-8.6 (C) no separation | 97.0 |
| 42. | 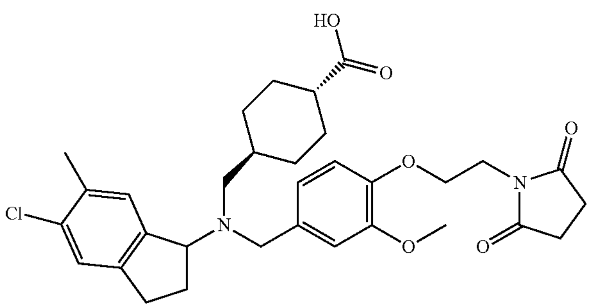 [SMILES: COc1cc(CN(C[C@H]2CC[C@H](C(=O)O)CC2)C2CCc3cc(Cl)c(C)cc32)ccc1OCCN1C(=O)CCC1=O] | 583 | 2.68 (A) | 91.7 |
| 43. | 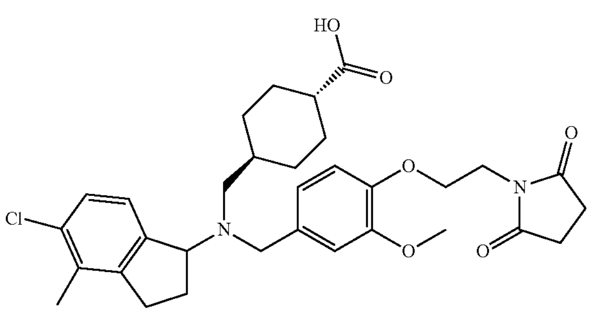 [SMILES: COc1cc(CN(C[C@H]2CC[C@H](C(=O)O)CC2)C2CCc3c2ccc(Cl)c3C)ccc1OCCN1C(=O)CCC1=O] | 583 | 2.67 (A) | 91.0 |

TABLE 4-continued

| Examples | Structure | (M + H)+ | Rt min. (system) | Purity (%) |
|---|---|---|---|---|
| 44. | 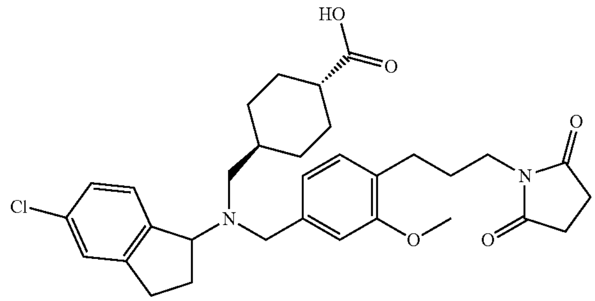 [SMILES: COc1cc(CN(C[C@H]2CC[C@H](C(=O)O)CC2)C2CCc3cc(Cl)ccc32)ccc1CCCN1C(=O)CCC1=O] | 567 | 6.68 (B) | 87.5 |
| 45. | Chiral | 567 | 4.8 (C) | 99.0 |
| 46. | Chiral | 567 | 5.8 (C) | 99.0 |
| 47. | 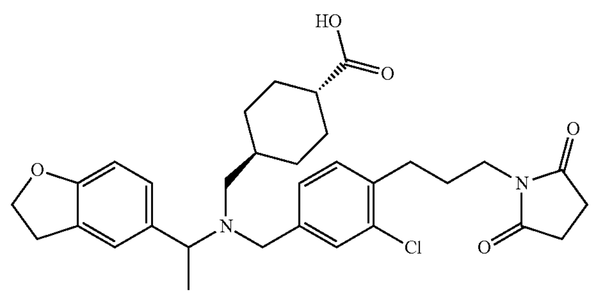 [SMILES: CC(c1ccc2c(c1)CCO2)N(Cc1ccc(CCCN2C(=O)CCC2=O)c(Cl)c1)C[C@H]1CC[C@H](C(=O)O)CC1] | 567 | 2.38 (A) | 91.0 |
| 48. | 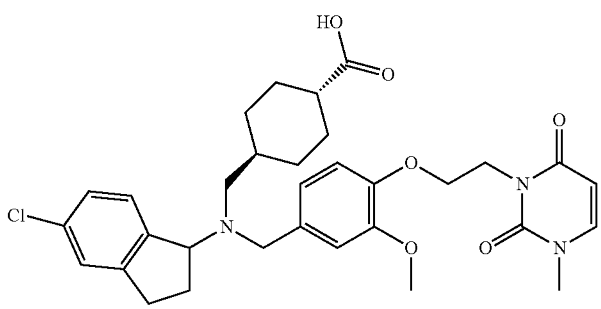 [SMILES: COc1cc(CN(C[C@H]2CC[C@H](C(=O)O)CC2)C2CCc3cc(Cl)ccc32)ccc1OCCn1c(=O)ccn(C)c1=O] | 596 | 2.70 (A) | 95.2 |

TABLE 4-continued

| Examples | Structure | (M + H)+ | Rt min. (system) | Purity (%) |
|---|---|---|---|---|
| 49. | 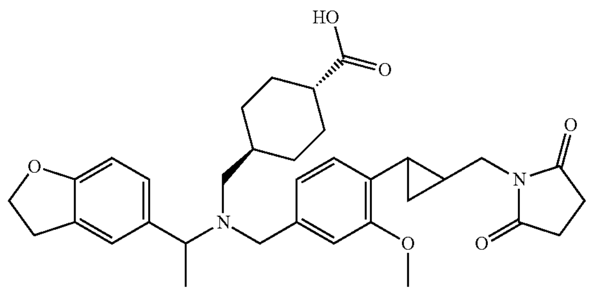 [SMILES: COc1cc(CN(C[C@H]2CC[C@H](C(=O)O)CC2)C(C)c2ccc3c(c2)CCO3)ccc1C1CC1CN1C(=O)CCC1=O] | 575 | 2.38 (A) | 98 |
| 50. | 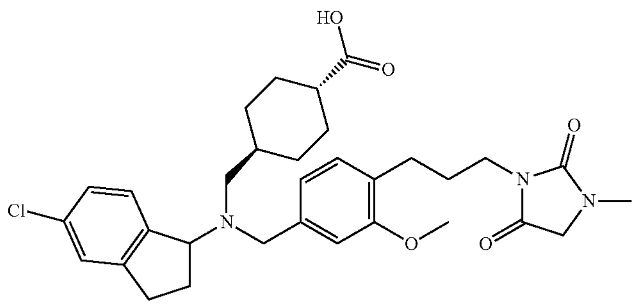 | 582 | 2.70 (A) | 91 |
| 51. | Chiral | 570 | 2.63 (A) | 92 |
| 52. | 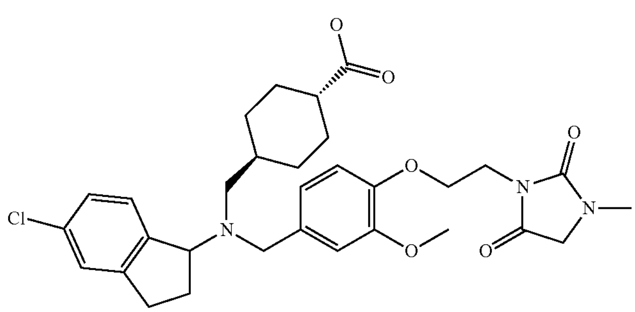 [SMILES: COc1cc(CN(C[C@H]2CC[C@H](C(=O)O)CC2)C2CCc3cc(Cl)ccc32)ccc1OCCN1C(=O)CN(C)C1=O] | 584 | 2.54 (A) | 96.8 |
| 53. | Chiral | 572 | 2.48 (A) | 96.8 |

TABLE 4-continued

| Examples | Structure | | (M + H)+ | Rt min. (system) | Purity (%) |
|---|---|---|---|---|---|
| 54. | 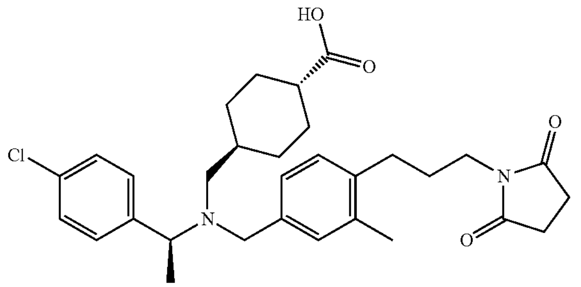 | Chiral | 539 | 2.57 (A) | 91.3 |
| 55. | 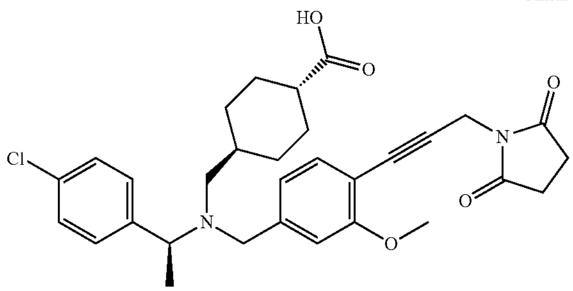 | Chiral | 551 | 2.74 (A) | 95.0 |
| 56. | 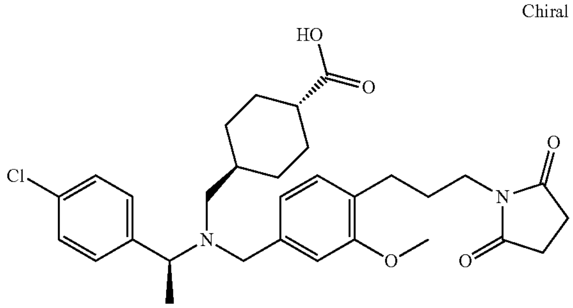 [SMILES: COc1cc(CN(C[C@H]2CC[C@H](C(=O)O)CC2)[C@@H](C)c2ccc(Cl)cc2)ccc1CCCN1C(=O)CCC1=O] | Chiral | 555 | 2.71 (A) | 92.0 |
| 57. | 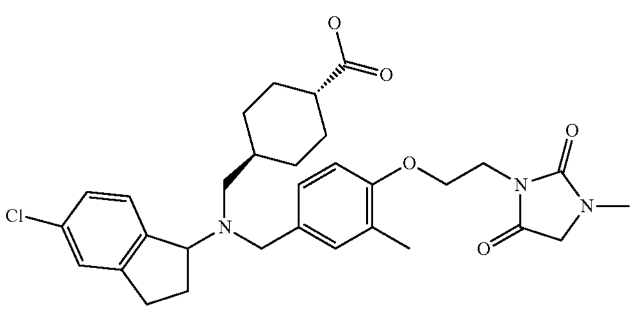 [SMILES: Cc1cc(CN(C[C@H]2CC[C@H](C(=O)O)CC2)C2CCc3cc(Cl)ccc32)ccc1OCCN1C(=O)CN(C)C1=O] | | 568 | 2.64 (A) | 96.5 |
| 58. | 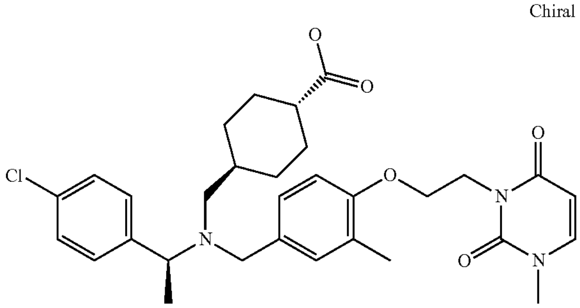 [SMILES: Cc1cc(CN(C[C@H]2CC[C@H](C(=O)O)CC2)[C@@H](C)c2ccc(Cl)cc2)ccc1OCCn1c(=O)ccn(C)c1=O] | Chiral | 568 | 2.41 (A) | 89.5 |

TABLE 4-continued

| Examples | Structure | (M + H)+ | Rt min. (system) | Purity (%) |
|---|---|---|---|---|
| 59. | 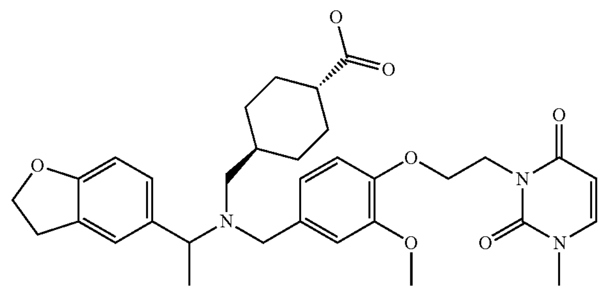 [SMILES: COc1cc(CN(C[C@H]2CC[C@H](C(=O)O)CC2)C(C)c2ccc3c(c2)CCO3)ccc1OCCn1c(=O)ccn(C)c1=O] | 592 | 2.55 (A) | 96.9 |
| 60. | 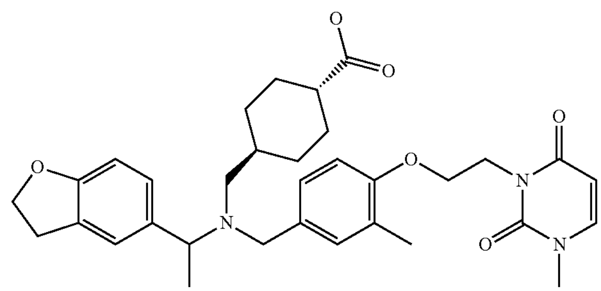 [SMILES: Cc1cc(CN(C[C@H]2CC[C@H](C(=O)O)CC2)C(C)c2ccc3c(c2)CCO3)ccc1OCCn1c(=O)ccn(C)c1=O] | 576 | 2.43 (A) | 94.0 |
| 61. | 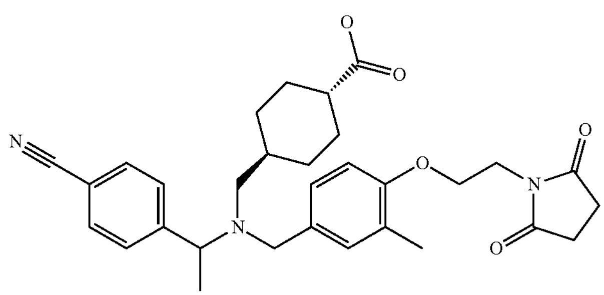 [SMILES: Cc1cc(CN(C[C@H]2CC[C@H](C(=O)O)CC2)C(C)c2ccc(C#N)cc2)ccc1OCCN1C(=O)CCC1=O] | 532 | 2.26 (A) | 95.9 |
| 62. | 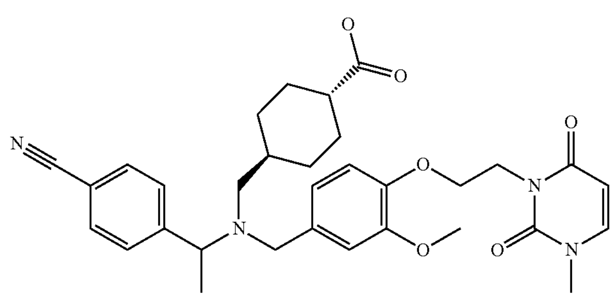 [SMILES: COc1cc(CN(C[C@H]2CC[C@H](C(=O)O)CC2)C(C)c2ccc(C#N)cc2)ccc1OCCn1c(=O)ccn(C)c1=O] | 575 | 2.57 (A) | 96.6 |
| 63. | 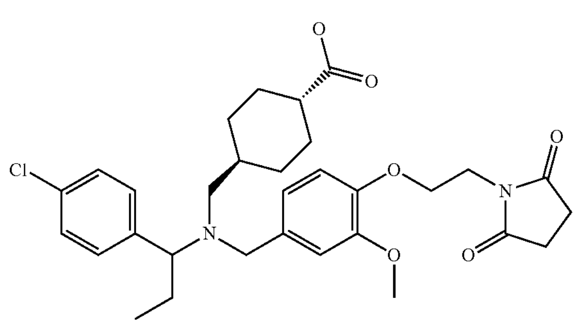 [SMILES: CCC(c1ccc(Cl)cc1)N(Cc1ccc(OCCN2C(=O)CCC2=O)c(OC)c1)C[C@H]1CC[C@H](C(=O)O)CC1] | 571 | 2.30 (A) | 95.0 |

TABLE 4-continued
| Examples | Structure | (M + H)+ | Rt min. (system) | Purity (%) |
|---|---|---|---|---|
| 64. | 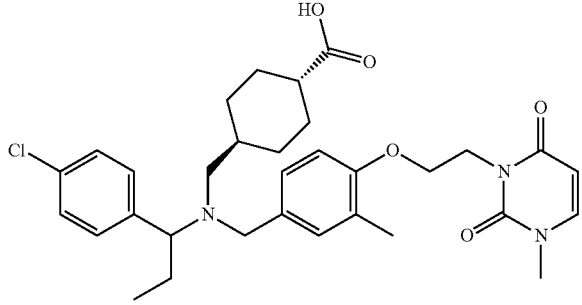 [SMILES: CCC(c1ccc(Cl)cc1)N(Cc1ccc(OCCn2c(=O)ccn(C)c2=O)c(C)c1)C[C@H]1CC[C@H](C(=O)O)CC1] | 582 | 2.35 (A) | 92.0 |
| 65. | 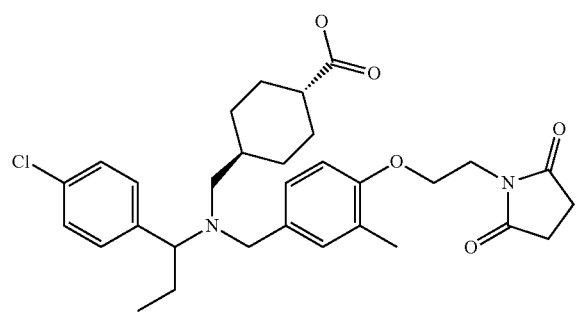 [SMILES: CCC(c1ccc(Cl)cc1)N(Cc1ccc(OCCN2C(=O)CCC2=O)c(C)c1)C[C@H]1CC[C@H](C(=O)O)CC1] | 555 | 2.38 (A) | 90.0 |
| 66. | 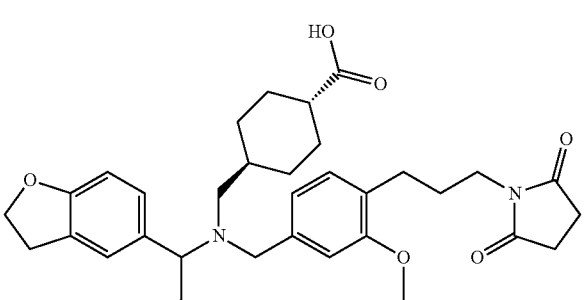 | 577 | 2.62 (A) | 89.2 |
| 67. | 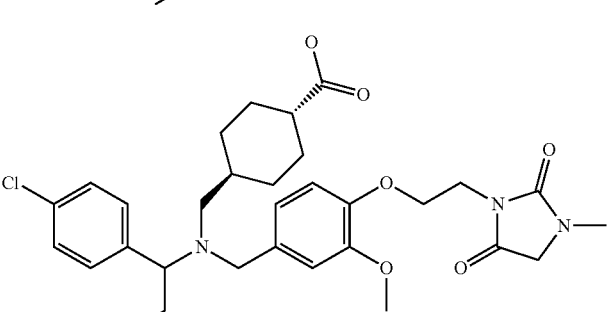 | 586 | 2.25 (A) | 92.0 |
| 68. | 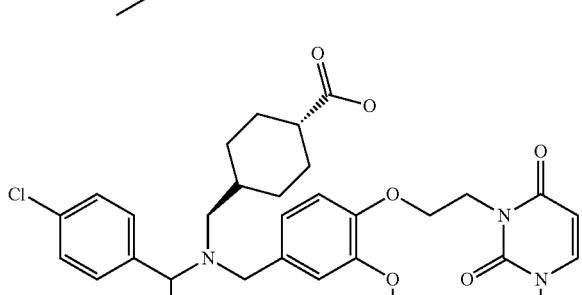 | 598 | 2.35 (A) | 93.0 |

TABLE 4-continued

| Examples | Structure | (M + H)+ | Rt min. (system) | Purity (%) |
|---|---|---|---|---|
| 69. | 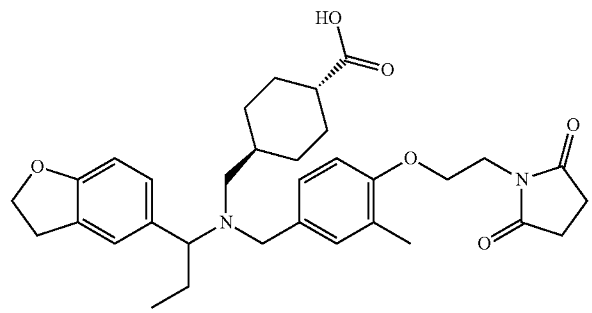 [SMILES: CCC(c1ccc2c(c1)CCO2)N(Cc1ccc(OCCN2C(=O)CCC2=O)c(C)c1)C[C@H]1CC[C@H](C(=O)O)CC1] | 563 | 2.60 (A) | 98.7 |
| 70. | 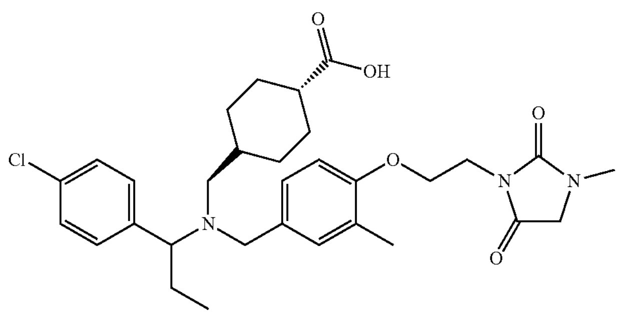 | 570 | 2.35 (A) | 93.0 |
| 71. | Chiral | 567 | 2.72 (A) | 95.0 |
| 72. | Chiral | 557 | 2.56 (A) | 96.4 |

TABLE 4-continued

| Examples | Structure | (M + H)⁺ | Rt min. (system) | Purity (%) |
|---|---|---|---|---|
| 73. | Chiral | 545 | 2.49 (A) | 97.3 |
| 74. | Chiral | 603 | 2.61 (A) | 93.1 |
| 75. | Chiral | 555 | 2.69 (A) | 98.2 |
| 76. | 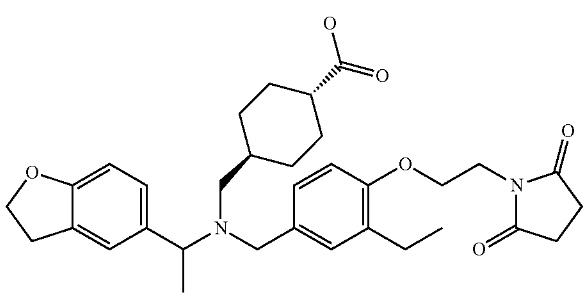 [SMILES: CCc1cc(CN(C[C@H]2CC[C@H](C(=O)O)CC2)C(C)c2ccc3c(c2)CCO3)ccc1OCCN1C(=O)CCC1=O] | 563 | 2.54 (A) | 98.5 |
| 77. | 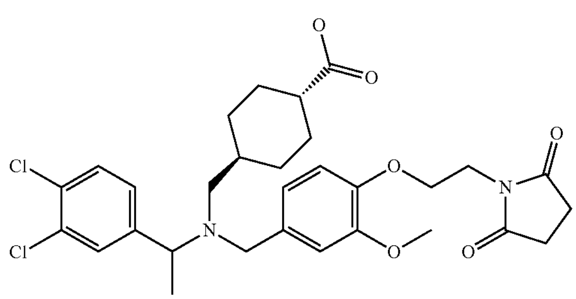 | 591 | 2.58 (A) | 94.6 |

TABLE 4-continued
| Examples | Structure | (M + H)+ | Rt min. (system) | Purity (%) |
|---|---|---|---|---|
| 78. | 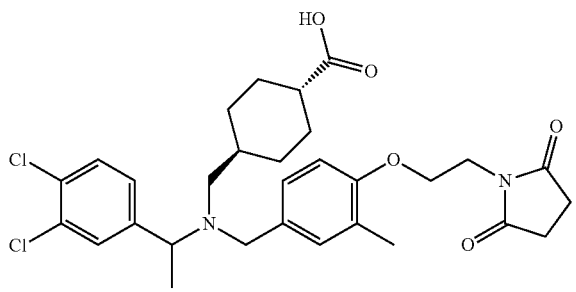 | 575 | 2.71 (A) | 96.8 |
| 79. | Chiral 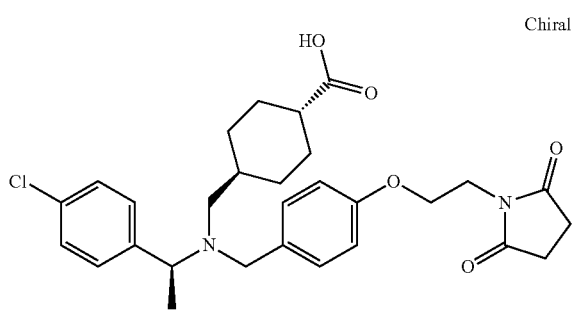 [SMILES: C[C@@H](c1ccc(Cl)cc1)N(Cc1ccc(OCCN2C(=O)CCC2=O)cc1)C[C@H]1CC[C@H](C(=O)O)CC1] | 527 | 2.48 (A) | 99.2 |
| 80. | 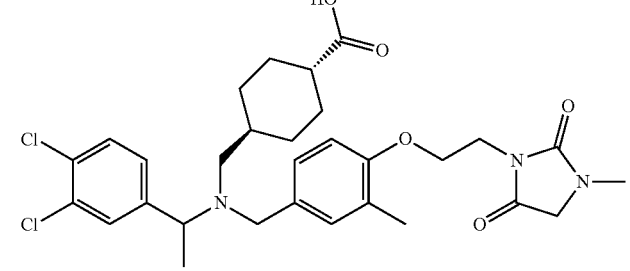 | 591 | 2.67 (A) | 94.5 |
| 81. | 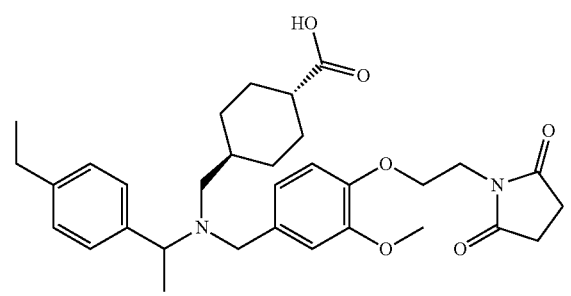 [SMILES: CCc1ccc(C(C)N(Cc2ccc(OCCN3C(=O)CCC3=O)c(OC)c2)C[C@H]2CC[C@H](C(=O)O)CC2)cc1] | 551 | 2.55 (A) | 98.5 |
| 82. | 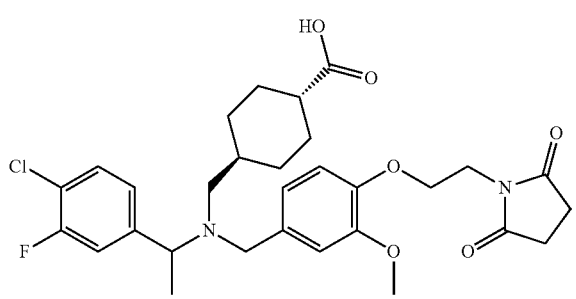 [SMILES: COc1cc(CN(C[C@H]2CC[C@H](C(=O)O)CC2)C(C)c2ccc(Cl)c(F)c2)ccc1OCCN1C(=O)CCC1=O] | 575 | 2.48 (A) | 98.8 |

TABLE 4-continued

| Examples | Structure | (M + H)+ | Rt min. (system) | Purity (%) |
|---|---|---|---|---|
| 83. | 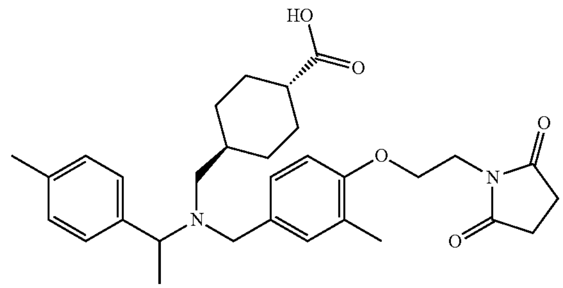 [SMILES: Cc1ccc(C(C)N(Cc2ccc(OCCN3C(=O)CCC3=O)c(C)c2)C[C@H]2CC[C@H](C(=O)O)CC2)cc1] | 521 | 2.56 (A) | 99.4 |
| 84. | 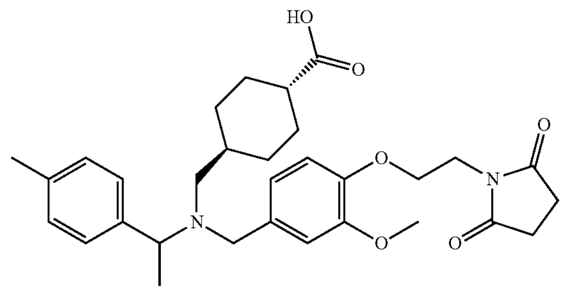 [SMILES: COc1cc(CN(C[C@H]2CC[C@H](C(=O)O)CC2)C(C)c2ccc(C)cc2)ccc1OCCN1C(=O)CCC1=O] | 537 | 2.39 (A) | 96.4 |
| 85. | Chiral | 557 | 2.33 (A) | 94.6 |
| 86. | Chiral | 601 | 2.88 (A) | 99.4 |
| 87. | Chiral | 573 | 2.59 (A) | 98.8 |

TABLE 4-continued

| Examples | Structure | | (M + H)+ | Rt min. (system) | Purity (%) |
|---|---|---|---|---|---|
| 88. | 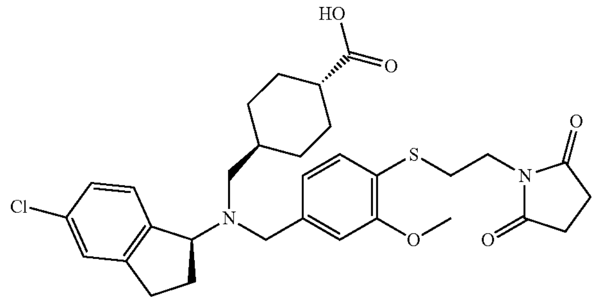 | Chiral | 585 | 2.64 (A) | 96.9 |
| 89. | 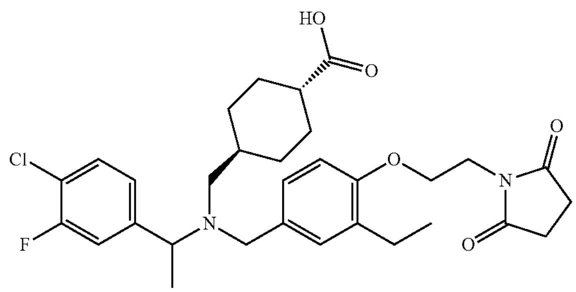 [SMILES: CCc1cc(CN(C[C@H]2CC[C@H](C(=O)O)CC2)C(C)c2ccc(Cl)c(F)c2)ccc1OCCN1C(=O)CCC1=O] | | 573 | 2.71 (A) | 98.7 |
| 90. | 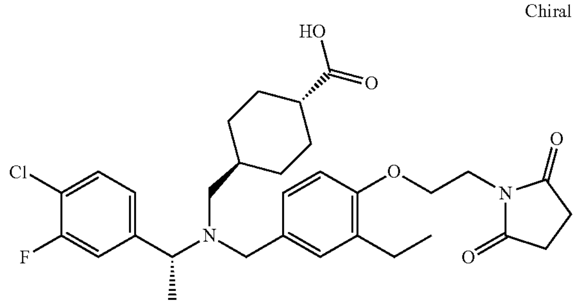 [SMILES: CCc1cc(CN(C[C@H]2CC[C@H](C(=O)O)CC2)[C@H](C)c2ccc(Cl)c(F)c2)ccc1OCCN1C(=O)CCC1=O] | Chiral | 573 | 2.71 (A) | 99.4 |
| 91. | 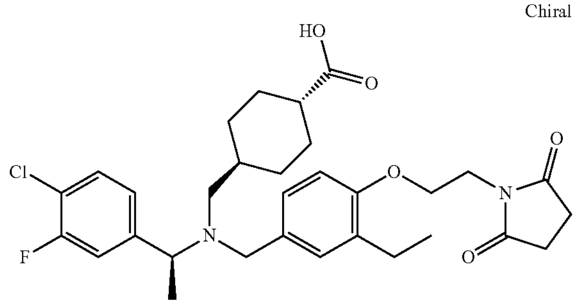 [SMILES: CCc1cc(CN(C[C@H]2CC[C@H](C(=O)O)CC2)[C@@H](C)c2ccc(Cl)c(F)c2)ccc1OCCN1C(=O)CCC1=O] | Chiral | 5.73 | 2.71 (A) | 96.5 |
| 92. | 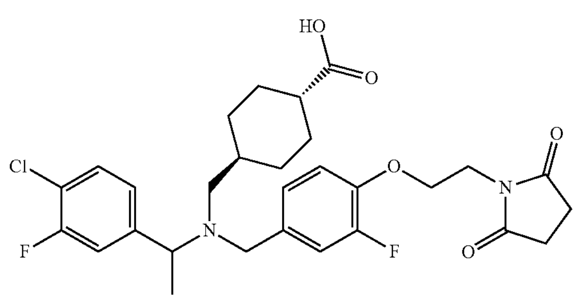 [SMILES: CC(c1ccc(Cl)c(F)c1)N(Cc1ccc(OCCN2C(=O)CCC2=O)c(F)c1)C[C@H]1CC[C@H](C(=O)O)CC1] | | 563 | 2.54 (A) | 95.3 |

TABLE 4-continued

| Examples | Structure | (M + H)+ | Rt min. (system) | Purity (%) |
|---|---|---|---|---|
| 93. | 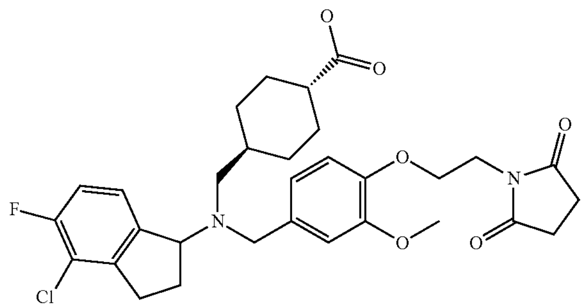 [SMILES: COc1cc(CN(C[C@H]2CC[C@H](C(=O)O)CC2)C2CCc3c2ccc(F)c3Cl)ccc1OCCN1C(=O)CCC1=O] | 587 | 2.54 (A) | 97.3 |
| 94. | 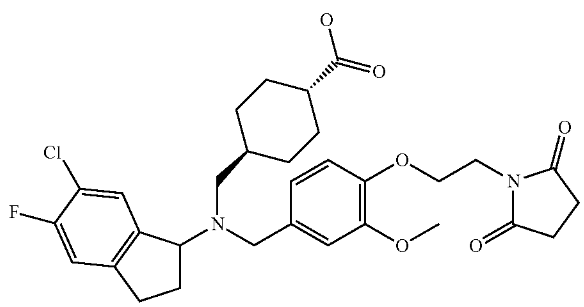 [SMILES: COc1cc(CN(C[C@H]2CC[C@H](C(=O)O)CC2)C2CCc3cc(F)c(Cl)cc32)ccc1OCCN1C(=O)CCC1=O] | 587 | 2.46 (A) | 98.2 |
| 95. | 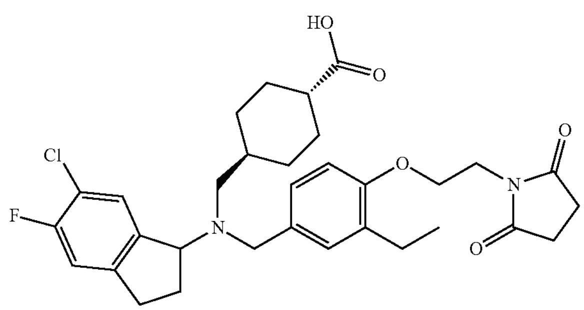 [SMILES: CCc1cc(CN(C[C@H]2CC[C@H](C(=O)O)CC2)C2CCc3cc(F)c(Cl)cc32)ccc1OCCN1C(=O)CCC1=O] | 585 | 2.68 (A) | 97.6 |
| 96. | 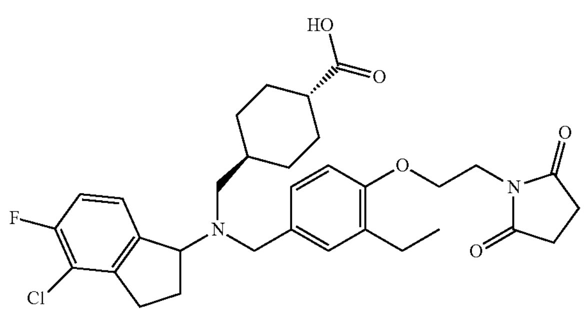 [SMILES: CCc1cc(CN(C[C@H]2CC[C@H](C(=O)O)CC2)C2CCc3c2ccc(F)c3Cl)ccc1OCCN1C(=O)CCC1=O] | 585 | 2.75 (A) | 99.4 |
| 97. | 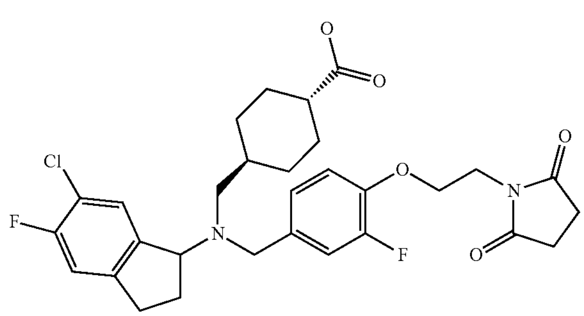 [SMILES: O=C1CCC(=O)N1CCOc1ccc(CN(C[C@H]2CC[C@H](C(=O)O)CC2)C2CCc3cc(F)c(Cl)cc32)cc1F] | 575 | 2.51 (A) | 98.8 |

TABLE 4-continued

| Examples | Structure | (M + H)+ | Rt min. (system) | Purity (%) |
|---|---|---|---|---|
| 98. | 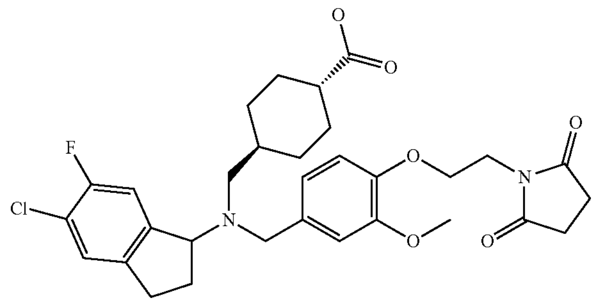 [SMILES: COc1cc(CN(C[C@H]2CC[C@H](C(=O)O)CC2)C2CCc3cc(Cl)c(F)cc32)ccc1OCCN1C(=O)CCC1=O] | 587 | 2.49 (A) | 95.0 |
| 99. | Chiral | 543 | 9.9 (C) | 98.5 |
| 100. | Chiral | 543 | 11.1 (C) | 99.8 |
| 101. | Chiral | 543 | 13.4 (C) | 97.6 |
| 102. | Chiral | 543 | 14.7 (C) | 97.4 |

TABLE 4-continued

| Examples | Structure | (M + H)+ | Rt min. (system) | Purity (%) |
|---|---|---|---|---|
| 103. | Chiral | 551 | 7.8 (C) | 85.4 |
| 104. | Chiral | 551 | 9.2 (C) | 99.2 |
| 105. | Chiral | 551 | 11.7 (C) | 97.6 |
| 106. | Chiral | 551 | 12.3 (C) | 97.3 |
| 107. | Chiral | 551 | 13.3 (C) | 99.8 |

TABLE 4-continued
| Examples | Structure | (M + H)+ | Rt min. (system) | Purity (%) |
|---|---|---|---|---|
| 108. | 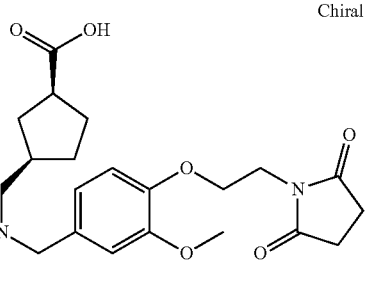 Chiral | 551 | 14.7 (C) | 94.8 |
| 109. | 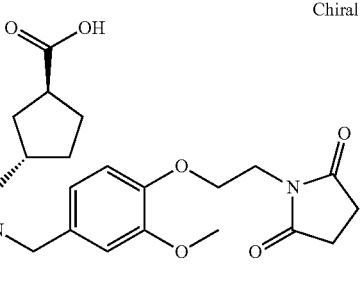 Chiral | 551 | 21.8 (C) | 93.8 |
| 110. | 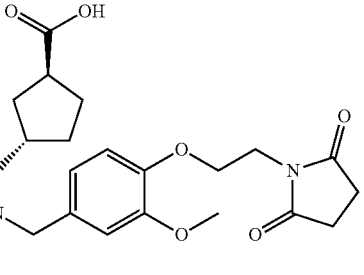 Chiral | 551 | 22.8 (C) | 91.6 |
| 111. | 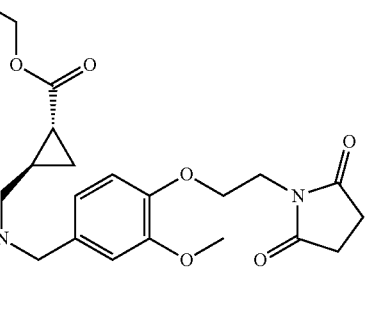 | 551 | 2.50 (A) | 92.2 |
| 112. | 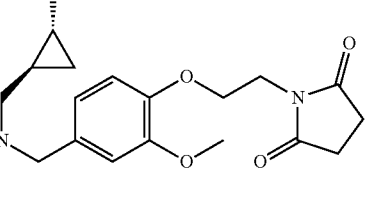 | 523 | 2.19 (A) | 93.1 |

TABLE 4-continued

| Examples | Structure | (M + H)+ | Rt min. (system) | Purity (%) |
|---|---|---|---|---|
| 113. | 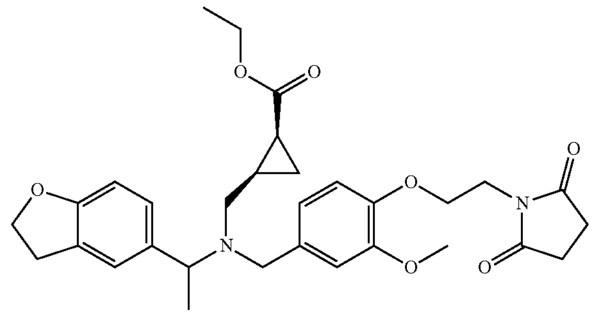 [SMILES: CCOC(=O)[C@H]1C[C@H]1CN(Cc1ccc(OCCN2C(=O)CCC2=O)c(OC)c1)C(C)c1ccc2c(c1)CCO2] | 551 | 2.56 (A) | 95.1 |
| 114. | 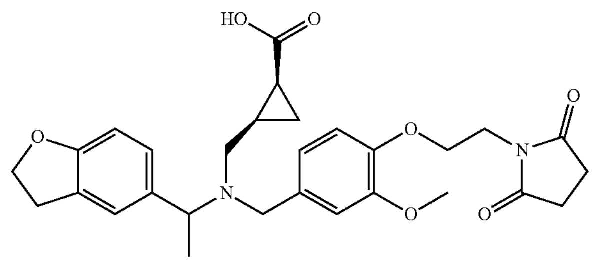 [SMILES: COc1cc(CN(C[C@@H]2C[C@@H]2C(=O)O)C(C)c2ccc3c(c2)CCO3)ccc1OCCN1C(=O)CCC1=O] | 523 | 2.19 (A) | 81.6 |
| 115. | 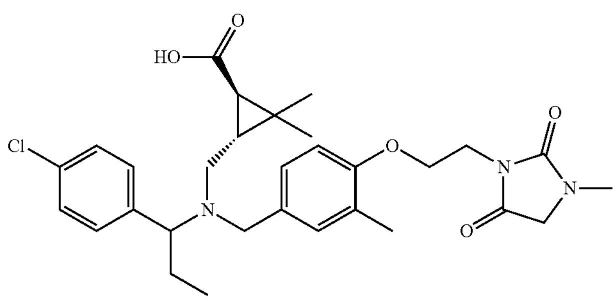 [SMILES: CCC(c1ccc(Cl)cc1)N(Cc1ccc(OCCN2C(=O)CN(C)C2=O)c(C)c1)C[C@@H]1[C@@H](C(=O)O)C1(C)C] | 556 | 2.30 (A) | 96.5 |
| 116. | 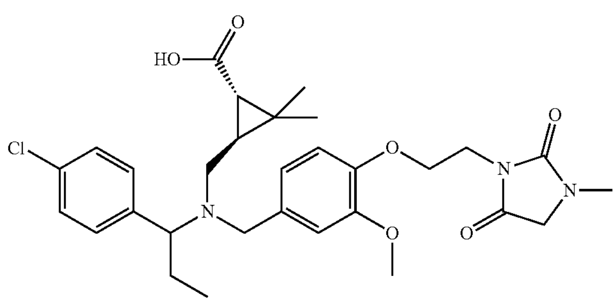 [SMILES: CCC(c1ccc(Cl)cc1)N(Cc1ccc(OCCN2C(=O)CN(C)C2=O)c(OC)c1)C[C@H]1[C@H](C(=O)O)C1(C)C] | 572 | 2.25 (A) | 97.5 |
| 117. | 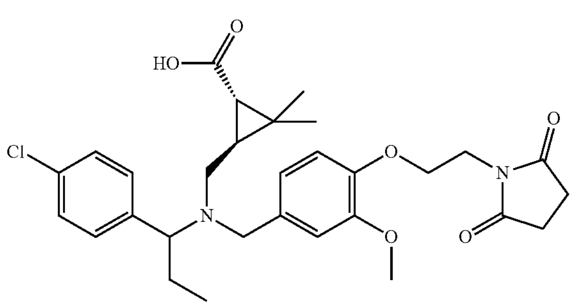 [SMILES: CCC(c1ccc(Cl)cc1)N(Cc1ccc(OCCN2C(=O)CCC2=O)c(OC)c1)C[C@H]1[C@H](C(=O)O)C1(C)C] | 557 | 2.63 (A) | 97.5 |

TABLE 4-continued

| Examples | Structure | (M + H)+ | Rt min. (system) | Purity (%) |
|---|---|---|---|---|
| 118. | 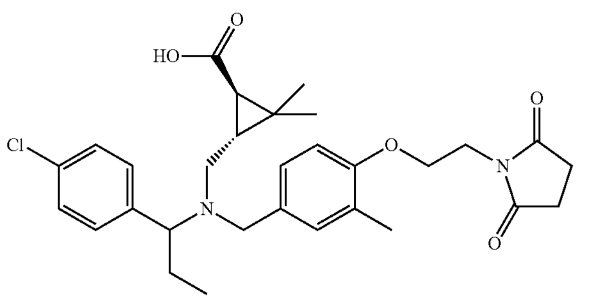 [SMILES: CCC(c1ccc(Cl)cc1)N(Cc1ccc(OCCN2C(=O)CCC2=O)c(C)c1)C[C@@H]1[C@@H](C(=O)O)C1(C)C] | 541 | 2.35 (A) | 94.0 |
| 119. | 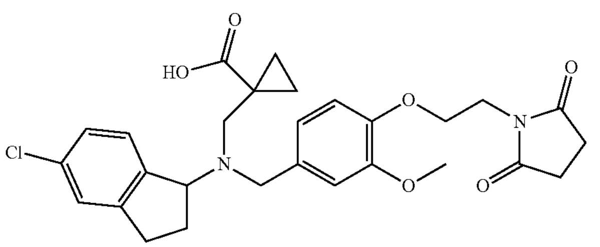 [SMILES: COc1cc(CN(CC2(C(=O)O)CC2)C2CCc3cc(Cl)ccc32)ccc1OCCN1C(=O)CCC1=O] | 527 | 2.60 (A) | 96.0 |

Example 120 trans-3-([1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid

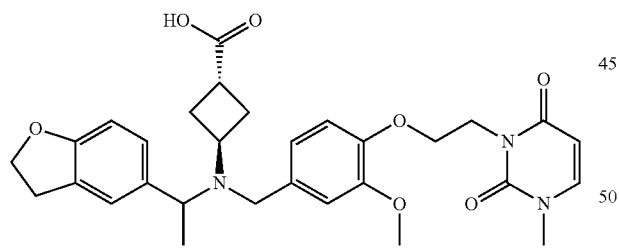

Step 1:

0.37 g (2.24 mmol) of 1-(2,3-dihydro-benzofuran-5-yl)-ethylamine (5.1) and 0.62 g (2.054 mmol) of Intermediate 4.13 are dissolved in 10 ml of THF. 0.17 ml (3.06 mmol) of AcOH and 1.08 g (5.09 mmol) of NaHB(OAc)$_3$ are added in and the reaction is stirred overnight. Then the mixture is diluted with water, pH adjusted to 8-9 with NaHCO$_3$ and it is extracted with EtOAc, the combined organic phase is washed water and brine, dried Na$_2$SO$_4$ and evaporated. The intermediate of 2.2 is 0.88 g (95.6%).

(M+H)$^+$=452, R$_t$=2.24 min (A), purity: 86.7%.

Step 2:

0.88 g (1.95 mmol) of formed secondary amine is dissolved in 15 ml of abs. EtOH, 0.334 g (2.92 mmol) of 3-oxo-cyclobutanecarboxylic acid (3.4), 0.17 ml (2.92 mmol) of AcOH and 0.313 g (2.92 mmol) of 2-picoline borane complex are added in. The mixture is stirred at 55° C. overnight, then is cooled, evaporated, diluted with water and extracted with DCM. The combined organic phases is dried, evaporated and purified by column chromatography (CHCl$_3$-MeOH 19/1). The first eluted is the titled compound. 110 mg (10.3%); (M+H)$^+$=550, R$_t$=3.16 min(B), purity: 93.2%.

Example 121 cis-3-([1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid

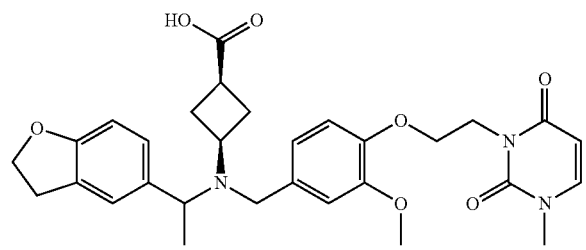

During the column chromatography of Example 120 the second eluted is the titled compound: 510 mg (47.6%); (M+H)$^+$=550, R$_t$=3.26 min (B), purity: 95.6%.

Example 122 cis-3-([(R)-1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid

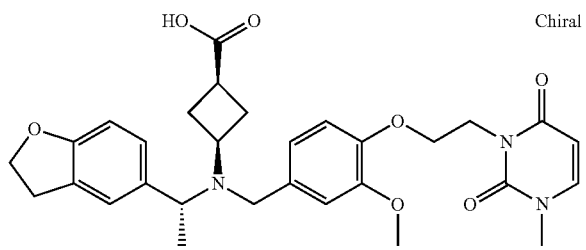 [SMILES: COc1cc(CN([C@H]2C[C@@H](C(=O)O)C2)[C@H](C)c2ccc3c(c2)CCO3)ccc1OCCn1c(=O)ccn(C)c1=O]

375 mg (0.68 mmol) of Example 121 is separated by preparative chiral column chromatography (Berger SFC systems; Chiralcel OJ-H 250×21 mm column (5 µM); 50 ml/min flow rate; CO2/80%/20%; EtOH+0.5% IPA). The first eluted enantiomer has (R)-configuration, yield is 124 mg (68%). $(M+H)^+$=550, $R_t$=10.7 min, purity: 100%.

Example 123 cis-3-([(S)-1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid

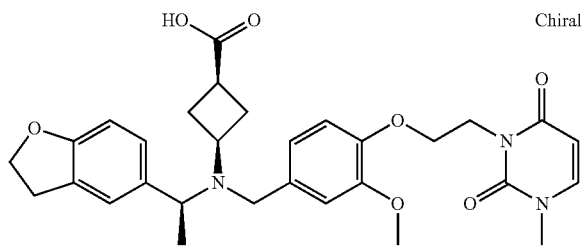 [SMILES: COc1cc(CN([C@H]2C[C@@H](C(=O)O)C2)[C@@H](C)c2ccc3c(c2)CCO3)ccc1OCCn1c(=O)ccn(C)c1=O]

375 mg (0.68 mmol) of Example 121 is separated by preparative chiral column chromatography (Berger SFC systems; Chiralcel OJ-H 250×21 mm column (5 µM); 50 ml/min flow rate; CO2/80%/20%; EtOH+0.5% IPA). The second eluted enantiomer has (S)-configuration, yield is 125 mg (68%). $(M+H)^+$=550, $R_t$=12.6 min, purity: 99.9%.

Example 124 trans-3-([1-(4-Chloro-3-fluoro-phenyl)-ethyl]-{4-[2-(2,5-dioxo-pyrrolidin-1-yl)-ethoxy]-3-methyl-benzyl}-amino)-cyclobutanecarboxylic acid

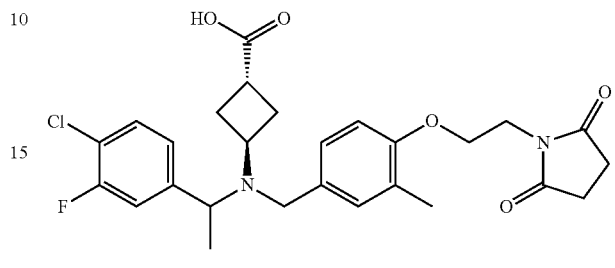

Step 1 is undertaking as in Example 120 using 1-(4-chloro-3-fluoro-phenyl)-ethyl-amine (5.7) and (4.2) for the first reductive amination step. $(M+H)^+$=419, $R_t$=2.44 min (A), purity: 93.9%.

Step 2:

2.73 g (6.5 mmol) of formed secondary amine is dissolved in 108 ml of THF, 1.487 g (2 equiv.) of 3-oxo-cyclobutanecarboxylic acid (3.4), 0.56 g (1.5 equiv.) of AcOH and 4.14 g (3 equiv.) of NaBH(OAc)3 are added in. The mixture is stirred at 35° C. for 48 h, then is cooled, diluted with water and extracted with EtOAc. The combined organic layer is purified by column chromatography (CHCl3-MeOH 19/1). The first eluted material is the titled compound. 180 mg (5.3%). $(M+H)^+$=517, $R_t$=4.69 min (B), purity: 96.5%.

Example 125 cis-3-([1-(4-Chloro-3-fluoro-phenyl)-ethyl]-{4-[2-(2,5-dioxo-pyrrolidin-1-yl)-ethoxy]-3-methyl-benzyl}-amino)-cyclobutanecarboxylic acid

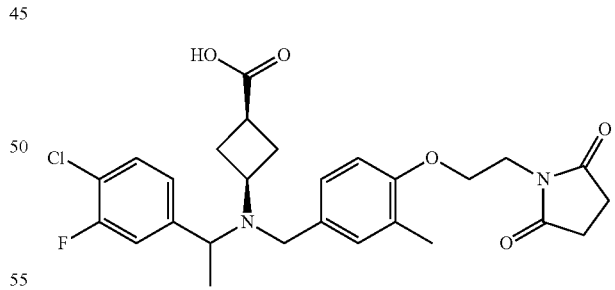

From Example 124 after the column chromatography the second eluted material is the titled compound: 310 mg (9.2%). $(M+H)^+$=517, $R_t$=4.70 min (B), purity: 99%.

Following the procedures as outlined in Example 121 using different amines (5), benzaldehydes (4) and oxo-cycloalkane carboxylic acid esters (3, R'=O), or as outlined in Example 1 using different amines (5), benzaldehydes (4) and formyl-cycloalkane carboxylic acid esters (3, R'=CHO) the compounds listed in Table 5 are prepared.

TABLE 5

| Examples | Structure | (M + H)+ | Rt min. (system) | Purity (%) |
|---|---|---|---|---|
| 126. | 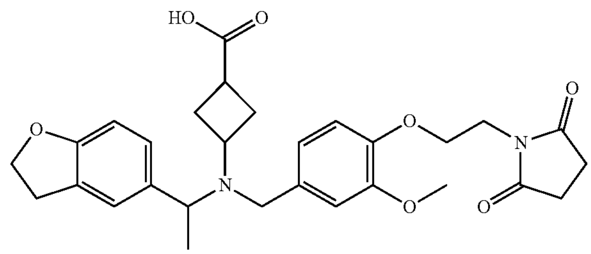 [SMILES: COc1cc(CN(C2CC(C(=O)O)C2)C(C)c2ccc3c(c2)CCO3)ccc1OCCN1C(=O)CCC1=O] | 583 | 2.16 and 2.20 trans/cis = 36/61 (A) | 92.3 |
| 127. | 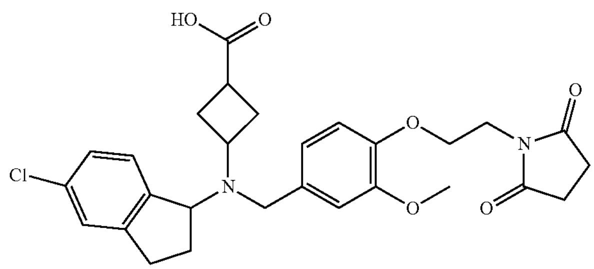 [SMILES: COc1cc(CN(C2CC(C(=O)O)C2)C2CCc3cc(Cl)ccc32)ccc1OCCN1C(=O)CCC1=O] | 527 | 2.40 and 2.43 trans/cis = 29/54 (A) | 83.0 |
| 128. | Chiral | 513 | 4.35 (B) | 96.5 |
| 129. | Chiral | 513 | 4.43 (B) | 97.7 |
| 130. | Chiral | 513 | 4.37 (B) | 98.9 |

TABLE 5-continued

| Examples | Structure | (M + H)+ | Rt min. (system) | Purity (%) |
|---|---|---|---|---|
| 131. | Chiral | 513 | 4.44 (B) | 97.1 |
| 132. | Chiral | 499 | 4.28 (B) | 97.4 |
| 133. | 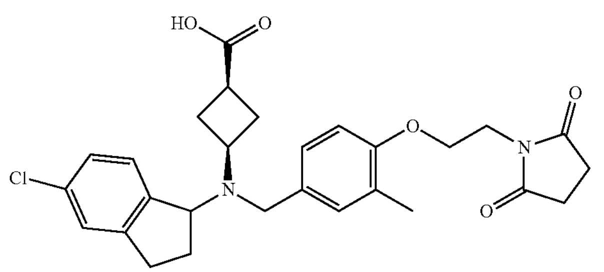 [SMILES: Cc1cc(CN(C2CCc3cc(Cl)ccc32)[C@H]2C[C@@H](C(=O)O)C2)ccc1OCCN1C(=O)CCC1=O] | 511 | 4.31 (B) | 92.8 |
| 134. | 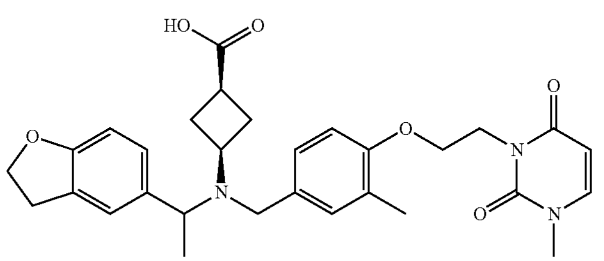 [SMILES: Cc1cc(CN(C(C)c2ccc3c(c2)CCO3)[C@H]2C[C@@H](C(=O)O)C2)ccc1OCCn1c(=O)ccn(C)c1=O] | 534 | 3.52 (B) | 93.6 |
| 135. | 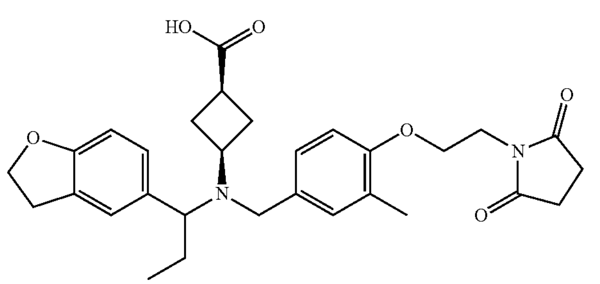 [SMILES: CCC(c1ccc2c(c1)CCO2)N(Cc1ccc(OCCN2C(=O)CCC2=O)c(C)c1)[C@H]1C[C@@H](C(=O)O)C1] | 521 | 3.81 (B) | 98.7 |

TABLE 5-continued
| Examples | Structure | (M + H)+ | Rt min. (system) | Purity (%) |
|---|---|---|---|---|
| 136. | Chiral 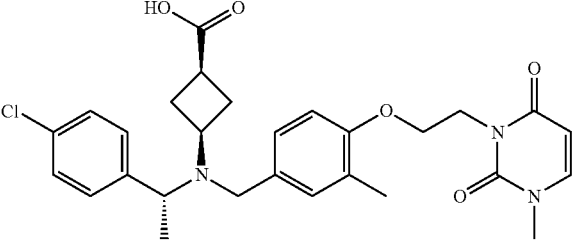 | 526 | 4.16 (B) | 97.7 |
| 137. | 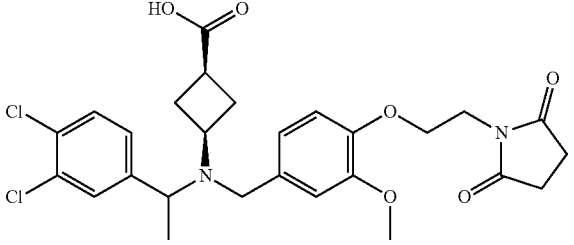 [SMILES: COc1cc(CN(C(C)c2ccc(Cl)c(Cl)c2)[C@H]2C[C@@H](C(=O)O)C2)ccc1OCCN1C(=O)CCC1=O] | 549 | 4.68 (B) | 99.4 |
| 138. | 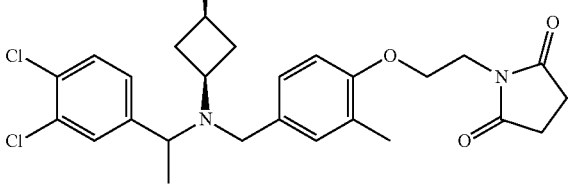 | 533 | 4.91 (B) | 100 |
| 139. | 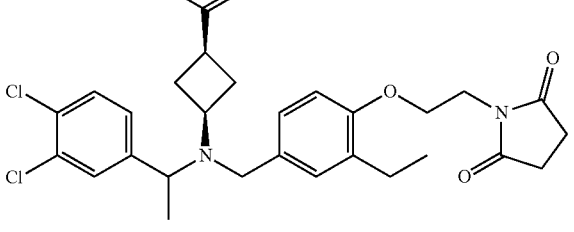 | 547 | 2.63 (A) | 99.7 |
| 140. | 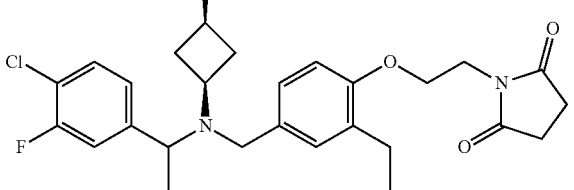 | 531 | 2.57 (A) | 97.8 |

TABLE 5-continued

| Examples | Structure | (M + H)⁺ | Rt min. (system) | Purity (%) |
|---|---|---|---|---|
| 141. | 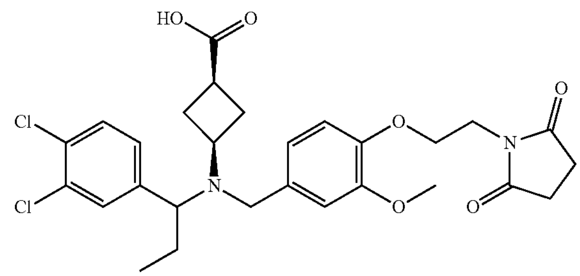 [SMILES: CCC(c1ccc(Cl)c(Cl)c1)N(Cc1ccc(OCCN2C(=O)CCC2=O)c(OC)c1)[C@H]1C[C@@H](C(=O)O)C1] | 563 | 4.98 (B) | 98.3 |
| 142. | 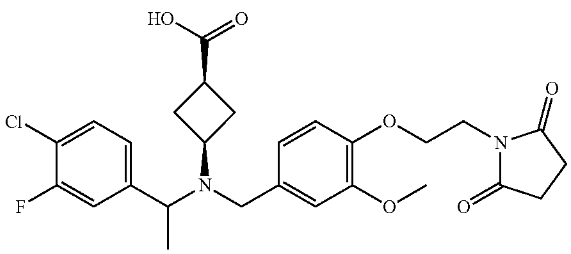 [SMILES: COc1cc(CN(C(C)c2ccc(Cl)c(F)c2)[C@H]2C[C@@H](C(=O)O)C2)ccc1OCCN1C(=O)CCC1=O] | 533 | 4.37 (B) | 96.7 |
| 143. | Chiral | 497 | 2.69 (B) | 97.4 |
| 144. | 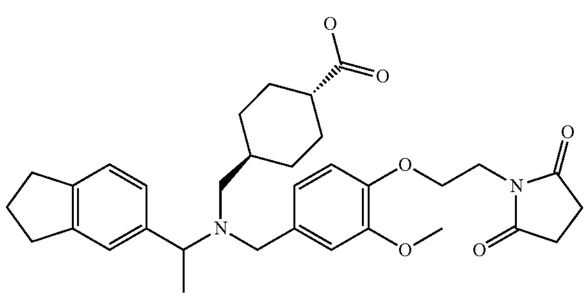 [SMILES: COc1cc(CN(C[C@H]2CC[C@H](C(=O)O)CC2)C(C)c2ccc3c(c2)CCC3)ccc1OCCN1C(=O)CCC1=O] | 563 | 2.81 (A) | 95.6 |
| 145. | 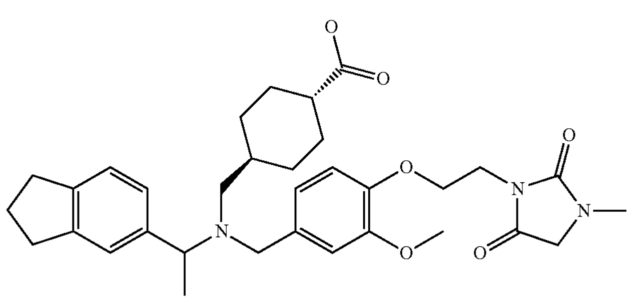 [SMILES: COc1cc(CN(C[C@H]2CC[C@H](C(=O)O)CC2)C(C)c2ccc3c(c2)CCC3)ccc1OCCN1C(=O)CN(C)C1=O] | 578 | 2.56 (A) | 97.4 |

TABLE 5-continued

| Examples | Structure | (M + H)+ | Rt min. (system) | Purity (%) |
|---|---|---|---|---|
| 146. | 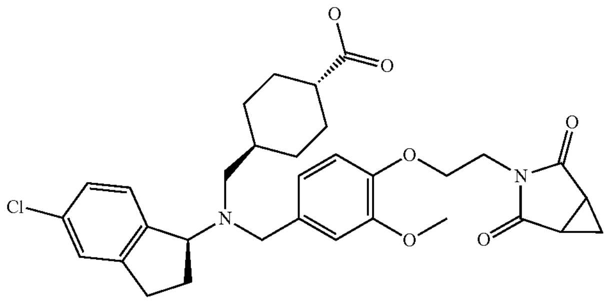 [SMILES: COc1cc(CN(C[C@H]2CC[C@H](C(=O)O)CC2)[C@H]2CCc3cc(Cl)ccc32)ccc1OCCN1C(=O)C2CC2C1=O] | 581 | 2.57 (A) | 97.9 |
| 147. | 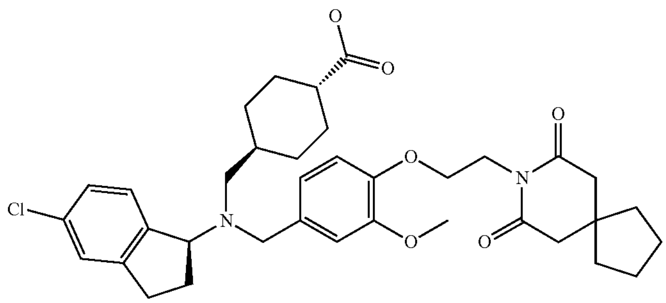 [SMILES: COc1cc(CN(C[C@H]2CC[C@H](C(=O)O)CC2)[C@H]2CCc3cc(Cl)ccc32)ccc1OCCN1C(=O)CC2(CCCC2)CC1=O] | 637 | 2.99 (A) | 97.4 |
| 148. | Chiral | 587 | 2.53 (A) | 96.5 |
| 149. | Chiral | 585 | 2.76 (A) | 94.5 |
| 150. | Chiral | 533 | 4.43 (B) | 98.7 |

TABLE 5-continued

| Examples | Structure | (M + H)+ | Rt min. (system) | Purity (%) |
|---|---|---|---|---|
| 151. | Chiral | 531 | 2.57 (A) | 99.3 |
| 152. | Chiral | 549 | 4.65 (B) | 99.8 |
| 153. | Chiral | 514 | 3.92 (B) | 98.0 |
| 154. | 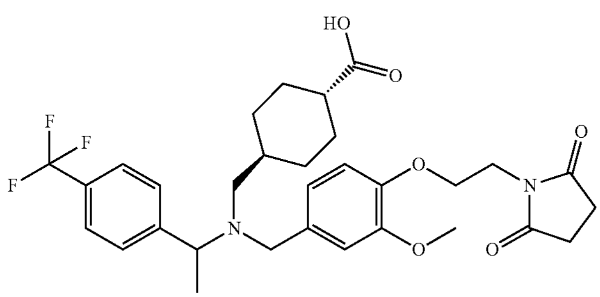 [SMILES: COc1cc(CN(C[C@H]2CC[C@H](C(=O)O)CC2)C(C)c2ccc(C(F)(F)F)cc2)ccc1OCCN1C(=O)CCC1=O] | 591 | 2.51 (A) | 95.8 |
| 155. | H—Cl | 621 | 5.34 (B) | 92.4 |

TABLE 5-continued

| Examples | Structure | | (M + H)+ | Rt min. (system) | Purity (%) |
|---|---|---|---|---|---|
| 156. | 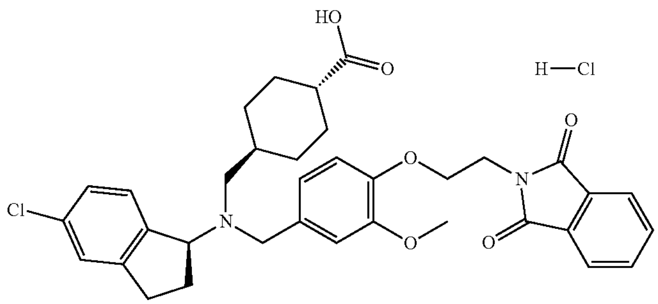 | | 617 | 5.65 (B) | 96.4 |
| 157. | 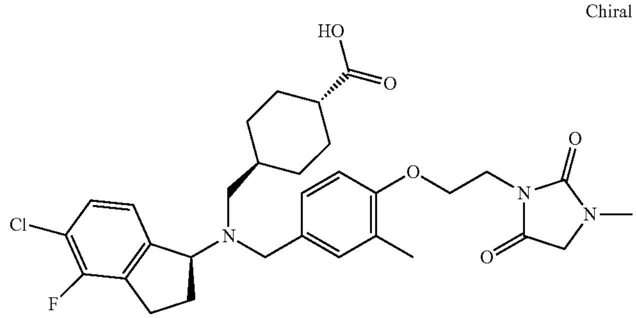 [SMILES: Cc1cc(CN(C[C@H]2CC[C@H](C(=O)O)CC2)[C@H]2CCc3c2ccc(Cl)c3F)ccc1OCCN1C(=O)CN(C)C1=O] | Chiral | 586 | 2.62 (A) | 93.7 |
| 158. | 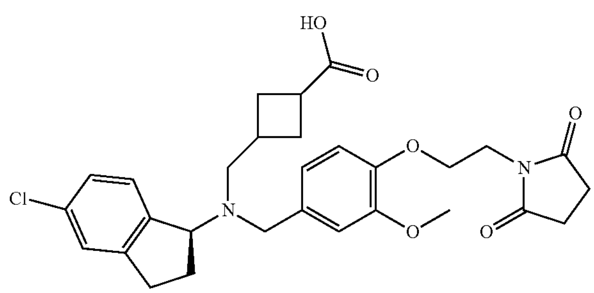 | Chiral | 541 | 2.35 and 2.38; trans/cis: 67/21; (A) | 88.0 |
| 159. | 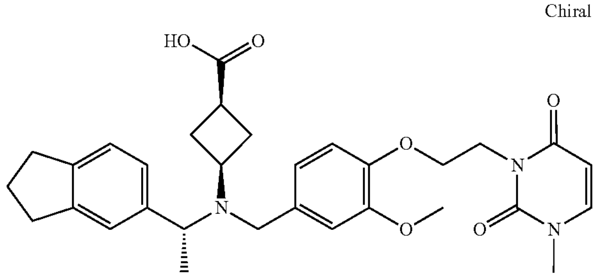 [SMILES: COc1cc(CN([C@H]2C[C@@H](C(=O)O)C2)[C@H](C)c2ccc3c(c2)CCC3)ccc1OCCn1c(=O)ccn(C)c1=O] | Chiral | 548 | 3.15 (B) | 92.5 |
| 160. | 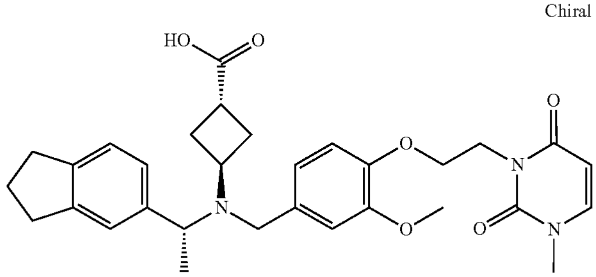 [SMILES: COc1cc(CN([C@H]2C[C@H](C(=O)O)C2)[C@H](C)c2ccc3c(c2)CCC3)ccc1OCCn1c(=O)ccn(C)c1=O] | Chiral | 548 | 3.05 (B) | 81.5 |

Biological Methods

Compounds according to the invention as described are useful to block the interaction of CXCR3-A and CXCL10 in a radiolabelled binding assay.

Competition radioligand binding assays were performed to determine the in vitro potency of the newly synthesized, unlabeled test compounds to displace the specific binding of the radiolabelled endogenous chemokine, 125I-CXCL10, from the human CXCR3-A receptor. $IC_{50}$ values were determined for the test compounds and used to explore the structure-activity relationships (SAR). The established SAR was used to feed back the molecular design and to suggest some suitable modifications for groups and structural elements by which the affinity of test compounds for the human CXCR3 receptor would be improved.

Cell Line and Membrane Preparation

CHO cells stably expressing human recombinant CXCR3-A receptors were generated in Sanofi-Aventis (LIT Frankfurt) by transfection of Flp-In-CHO host cells with a plasmid construct of pCDA5-FRT-TO_IRES-Gai4qi4_DEST. This cell line was registered in Sanofi-Aventis cell line bank. Cells were grown in Ham's F12 (PAA) medium supplemented with 10% FCS (PAA, Cat No. E15-898) and 0.6% Hygromycin (PAA) in T175 flasks at 37° C. in a humidified incubator under 5% CO 2, 95% air. Cells were harvested from the culture flasks by a short treatment (8-10 minutes) with Versene (Gibco, Cat No. 15040). Cell suspension was diluted with PBS and cells were collected with centrifugation at 230 g for 10 minutes at 10° C. with a Juan centrifuge. Pellets containing approximately $1\times10^8$ cells were resuspended in 15 ml of 20 mM HEPES pH=7.4, 10 mM EDTA buffer supplemented with complete protease inhibitor (Roche, Cat No. 11 697 498 001). This suspension was homogenized with a Teflon/glass homogenizer (Sartorius potter S) with 3×10 sec pulses in ice cold water bath, and then centrifuged at 300×g for 10 min at 4° C. with a Sigma centrifuge. The supernatant was carefully collected and centrifuged at 100,000×g for 60 min at 4° with a Beckman Avanti J30 centrifuge. The resulting pellet was washed once with 15 ml of fresh preparation buffer. The final membrane pellet was resuspended in storage buffer (20 mM HEPES pH=7.4, 0.1 mM EDTA, 250 mM sucrose supplemented with complete protease inhibitor) in a volume ratio of approximately $1\times10^8$ cells/1 ml, which gave a protein concentration of 2 to 4 mg/ml. Protein concentration was determined with Bio-Rad protein assay (Cat No 500-0006). Membrane aliquots were stored at −80° C. No degradation was observed until a storage period of approximately 5 months.

125I-CXCL10 Radioligand Binding Study

The composition of the binding assay buffer was determined in a course of detailed optimization procedure. This resulted in a binding assay buffer constituted by the following components: 25 mM HEPES (pH=7.4), 5 mM $MgCl_2$, 1 mM $CaCl_2$, 100 mM NaCl, supplemented with 0.1% of protease free BSA (as a final concentration). Competition binding assay was performed using 125I-CXCL10 (PerkinElmer, NEX348, specific activity 2200 Ci/mmol) radioligand in a final concentration of 50-70 pM. The nonspecific binding was defined by 150 pM of hr-CXCL10 (R&D Systems, Cat No 266-IP). The total assay volume was equal to 150 µl and contained 0.1% of DMSO (final concentration). Binding reaction was initiated by adding of membranes (10-20 µg proteins, approximately $5\times10^5$ cell equivalents) to the reaction mixture. After 60 minutes of incubation at 25° C. the reaction was terminated by rapid filtration over GF/B glass fiber filters that were pre-soaked with 0.5% polyethyleneimine (Fluka Analytical, P3143) for 1 hour, using a Skatron cell harvester device. Filters then were washed with 8 ml of ice-cold wash buffer (modified binding buffer in which BSA was omitted and the concentration of NaCl was adjusted to 500 mM concentration). The radioactivity retained on the filters was measured by a Wizard 1470 Automatic Gamma counter.

Test compounds were dissolved prior to the binding assay at a concentration of 10 mM in DMSO. Stock solutions were stored at −20° C. for not longer than 3 months. On the day of binding assay serial dilutions of test compounds ranging from 10 mM up to $3\times10^{-7}$ M (or $3\times10^{-9}$ M) were generated by 8 (or 12) consecutive steps using DMSO as solvent. Before adding these solutions of test compound to the binding reaction mixture, an intermediate dilution procedure was applied, in which 30 µL of each solution sample was transferred into a dilution tube containing 970 µL of binding assay buffer. Then 50 µL of these second dilution series was added to the test tubes and a concentration range of test compounds between $1\times10^{-5}$ M and $3\times10^{-9}$ M (or $3\times10^{-11}$ M).

The $IC_{50}$ values and Hill slopes for competition binding data were obtained using nonlinear four-parametric curve fitting method.

The exemplified compounds of the present invention have activities in the above binding assay of less than 20 micromolar, more particular compound have activities of less than 1 micromolar, and further particular compounds have activities of less than 200 nanomolar IC50.

TABLE 6

| Example # | IC50 (nM) |
|---|---|
| 1.1 | 177 |
| 1 | 60 |
| 2 | 760 |
| 3 | 60 |
| 4 | 37 |
| 5 | 19 |
| 6 | 20 |
| 7 | 38 |
| 8 | 3810 |
| 9 | 32 |
| 10 | 64 |
| 11 | 200 |
| 12 | 13 |
| 13 | 1660 |
| 14 | 25 |
| 15 | 37 |
| 16 | 35 |
| 17 | 44 |
| 18 | 64 |
| 19 | 55 |
| 20 | 1200 |
| 21 | 633 |
| 22 | 112 |
| 23 | 116 |
| 24 | 58 |
| 25 | 25 |
| 26 | 64 |
| 27 | 80 |
| 28 | 81 |
| 29 | 150 |
| 30 | 53 |
| 31 | 360 |
| 32 | 123 |
| 33 | 42 |
| 34 | 22 |
| 35 | 1430 |
| 36 | 28 |
| 37 | 76 |
| 38 | 163 |
| 39 | 99 |
| 40 | 81 |
| 41 | 131 |
| 42 | 87 |

TABLE 6-continued

| Example # | IC50 (nM) |
|---|---|
| 43 | 68 |
| 44 | 410 |
| 45 | 160 |
| 46 | 1000 |
| 47 | 800 |
| 48 | 409 |
| 49 | 746 |
| 50 | 1240 |
| 51 | 157 |
| 52 | 177 |
| 53 | 789 |
| 54 | 482 |
| 55 | 6600 |
| 56 | 215 |
| 57 | 200 |
| 58 | 169 |
| 59 | 195 |
| 60 | 345 |
| 61 | 102 |
| 62 | 200 |
| 63 | 62 |
| 64 | 487 |
| 65 | 121 |
| 66 | 85 |
| 67 | 77 |
| 68 | 143 |
| 69 | 56 |
| 70 | 180 |
| 71 | 176 |
| 72 | 825 |
| 73 | 154 |
| 74 | 350 |
| 75 | 45 |
| 76 | 45 |
| 77 | 182 |
| 78 | 270 |
| 79 | 154 |
| 80 | 431 |
| 81 | 245 |
| 82 | 46 |
| 83 | 146 |
| 84 | 107 |
| 85 | 71 |
| 86 | 85 |
| 87 | 19 |
| 88 | 23 |
| 89 | 52 |
| 90 | 494 |
| 91 | 121 |
| 92 | 220 |
| 93 | 84 |
| 94 | 630 |
| 95 | 4040 |
| 96 | 443 |
| 97 | 4640 |
| 98 | 155 |
| 99 | 223 |
| 100 | 108 |
| 101 | 1810 |
| 102 | 154 |
| 103 | 260 |
| 104 | 15 |
| 105 | 53 |
| 106 | 144 |
| 107 | 5130 |
| 108 | 190 |
| 109 | 73 |
| 110 | 525 |
| 111 | 646 |
| 112 | 145 |
| 113 | 82 |
| 114 | 180 |
| 115 | 244 |
| 116 | 160 |
| 117 | 71 |
| 118 | 190 |
| 119 | 3200 |
| 120 | 2900 |
| 121 | 152 |
| 122 | 70 |
| 123 | 7000 |
| 124 | 24% at 10 µM |
| 125 | 465 |
| 126 | 58 |
| 127 | 1090 |
| 128 | 37% at 10 µM |
| 129 | 105 |
| 130 | 5300 |
| 131 | 6500 |
| 132 | 170 |
| 133 | 1640 |
| 134 | 240 |
| 136 | 347 |
| 137 | 104 |
| 138 | 670 |
| 139 | 1200 |
| 140 | 260 |
| 141 | 200 |
| 142 | 120 |
| 143 | 3000 |
| 144 | 167 |
| 145 | 146 |
| 146 | 254 |
| 147 | 7000 |
| 148 | 26 |
| 149 | 165 |
| 150 | 98 |
| 151 | 457 |
| 152 | 149 |
| 153 | 294 |
| 154 | 70 |
| 155 | 2870 |
| 156 | 79 |
| 157 | 71 |
| 158 | 1060 |
| 159 | 544 |
| 160 | 26% at 10 µM |

Cyclic AMP Accumulation Assay

An in vitro functional assay measuring the changes in the intracellular cyclic adenosine 3',5'-monophosphate (cyclic AMP, or also called as cAMP) level following either stimulation or activation of CXCR3-A receptor was used to demonstrate the antagonistic functionality of the selected compounds.

Cyclic AMP is one of the most important intracellular second messenger molecules whose level is regulated principally by the G-protein coupled adenylyl cyclase effector enzyme located in the inner surface of the cellular plasma membrane. Receptor dependent, G-protein mediated changes in the cyclic AMP concentration elicit then complex regulatory processes within the cell such as activation of multiple protein kinases and phospholipases, generation of inositol triphosphate and transient rise in the intracellular calcium ion (Ca2+) concentration, ion channel gating, effects on different gene transcriptions.

Upon agonist stimulation, CXCR3-A receptor activates the pertussis toxin (PTX) sensitive G-proteins of the Gi class that mediates a reduction in the intracellular cAMP levels, an increase in the intracellular Ca2+ mobilization and actin polymerization, that finally lead to cytoskeletal rearrangement and directed cell migration (chemotaxis). [Sauty A et al, 2001. J. Immunol. 167: 7084-7093.]

Cyclic AMP accumulation assay was performed with a homogeneous time-resolved fluorescence (HTRF) cAMP femto 2 kit from CisBio International. The measurement was basically carried out by following the manufacturer's instructions.

Since CXCR3-A receptor is coupled to Gi-protein, thus an agonist activation of the receptor will lead to a decrease in the intracellular cAMP level [Crosignani S. et al, 2010. Bioorg. Med. Chem Letters, 20:3614-3617]. Therefore, the cells have to be preactivated by forskolin, a direct activator of the cell adenylyl cyclase enzyme, in order to reach a sufficient cellular basal cAMP level. The agonist induced decrease in cAMP level will be measured by an increase of the Fluorescence Resonance Energy Transfer signal, as the signal is inversely proportional to the concentration of cAMP in the cell.

For the assay, the adherent hr-CXCR3-Flp-In-CHO—IRES-Gai4qi4 cells (the same cell line as used for binding assay) were washed with Ca2+-Mg2+ free PBS and harvested by a short treatment with Acutase (Sigma, A6964). At a time point of 2 min after adding Acutase (3 ml/T175 flask) 7 ml of culture medium was added to the detached cells. Cell suspension was collected and centrifuged at 1,700 rpm for 10 min. (Sigma 2-S table centrifuge). The resulting cell pellet was resuspended in PBS with Ca2+/Mg2+ (Invitrogen 14080-048) and subjecting to a second centrifugation step as above. The final cell pellet was resuspended in assay buffer (PBS with Ca2+/Mg2+, supplemented with fatty acid free BSA (Sigma A6003) at a final concentration of 1 mg/ml and with the phosphodiesterase inhibitor Rolipram (Calbiochem 557330) at a final concentration of 10 µM. Cells were transferred to a 96-well microplate (Costar 3694, Half Area flat bottom, non-treated, black polystyrene plate) at a density of 16,000 cells/well.

The cells were incubated in the presence of different concentrations of antagonist compounds (within the range of 1004 and 0.1 nM) for 10 min at room temperature (R.T.) under continuous shaking the microplate in a plate shaker (Heidolph Titramax 100, at 600 rpm). The final concentration of DMSO in reaction mixture was 0.1%. Then CXCL10 at a final concentration of 20 nM was added and the cells were further incubated for 10 min at R.T., as above. After that forskolin (Sigma F-6886) at 1 µM final concentration was added and an additional incubation period (30 min, R.T., shaking) followed. The final reaction volume was 40 µl. The reaction was stopped by adding the lysis buffer containing the HTRF reagents.

Plates were then incubated for 60 min at R.T. under shaking, and time-resolved FRET signals were measured after excitation at 337 nm. Both the emission signal from the europium cryptate-labelled anti-cAMP antibody (620 nm) and the FRET signal resulting from the labelled cAMP-d2 (665 nm) were recorded using a RubyStar instrument (BMG Labtechnologies).

The results were calculated as a fluorescence ratio (Em.665 nm/Em.620 nm)×10000 and were analyzed by calculating the Delta F value which corresponded to the following formula:

Delta $F$=(Standard or Sample Ratio−Negative Control Ratio)/(Negative Control Ratio)×100.

The negative control corresponded to the background signal obtained with the cryptate conjugate alone.

The compounds tested in the above functional cAMP assay displayed an 1050 value of less than 2 micromolar and particularly less than 20 nanomolar.

Formulation Examples (1) Tablets

The ingredients below are mixed by an ordinary method and compressed by using a conventional apparatus.

| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below are mixed by an ordinary method and filled in soft capsules.

| Compound of Example 1 | 30 mg |
| Olive oil | 300 mg |
| Lecithin | 20 mg |

(1) Parenteral Preparations

The ingredients below are mixed by an ordinary method to prepare injections contained in a 1 ml ampoule.

| Compound of Example 1 | 3 mg |
| Sodium chloride | 4 mg |
| Distilled water for injection | 1 ml |

The compounds of the present invention have CXCR3 inhibitory activity and are useful as an active ingredient of a medicament for preventive and/or therapeutic treatment of a CXCR3 receptor mediated disease or disorder, especially of a disease or disorder selected from the group consisting of COPD, psoriasis, graft/transplant rejection, ophthalmological disease, celiac disease, inflammatory bowel disease (IBD), type 1 diabetes, myasthenia gravis (MG), multiple sclerosis (MS) and other neuroinflammatory diseases, lupus, rheumatoid arthritis (RA) or lichen planus.

What we claim is:

1. A compound of formula 1

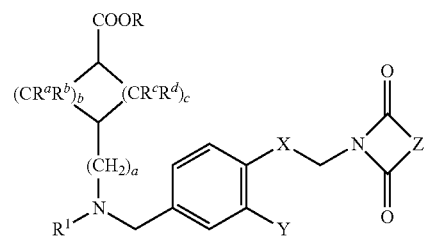

wherein

R represents hydrogen or $C_{1-4}$ alkyl group;

$R^1$ represents a group selected from the group consisting of

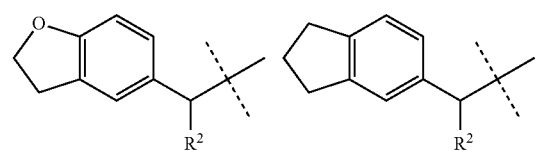

-continued

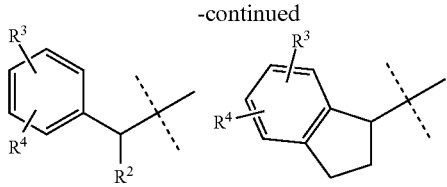

wherein
R² represents hydrogen or $C_{1-4}$ alkyl group;
R³ represents hydrogen, halogen, $CF_3$, CN or $C_{1-4}$ alkyl; and
R⁴ represents hydrogen, halogen or $C_{1-4}$ alkyl;
a=0, 1 or 2; b=0, 1, 2 or 3, c=1, 2 or 3, and
$R^a$, $R^b$, $R^c$ and $R^d$ represent independently from each other H or $C_{1-4}$ alkyl;
X represents a $C_2$ aliphatic hydrocarbon bridge optionally containing a double bond or a triple bond or a heteroatom selected from O and S, or —CH(CH₂)CH—;
Y represents hydrogen, halogen, $C_{1-4}$ alkyl, $C_{1-4}$ alkoxy or $C_{1-4}$ hydroxyalkyl; and
Z represents a $C_{1-4}$ aliphatic hydrocarbon bridge optionally containing one double bond, and/or one or more heteroatom selected from O, S, N and N(CH₃) or represents a $C_{2-4}$ aliphatic hydrocarbon bridge fused with a $C_{3-6}$ cycloalkyl ring optionally containing one or more double bond or with a phenyl ring or represents a $C_{1-4}$ aliphatic hydrocarbon bridge substituted with a spiro $C_{3-6}$ cycloalkyl ring optionally containing one or more double bond;
or a pharmaceutically acceptable salt or stereoisomer thereof or a pharmaceutically acceptable salt of the stereoisomer.

2. A compound according to claim 1, wherein
R represents hydrogen or $C_{1-4}$ alkyl;
R¹ represents a group selected from the group consisting of

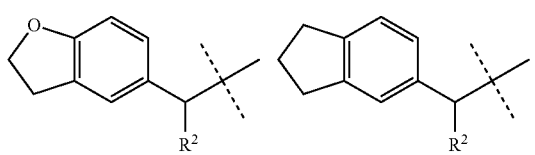

wherein
R² represents hydrogen or $C_{1-4}$ alkyl;
R³ represents hydrogen, halogen, $CF_3$, CN or $C_{1-4}$ alkyl; and
R⁴ represents hydrogen, halogen or $C_{1-4}$ alkyl;
a=0 or 1; b=0, 1 or 2, c=1, 2 or 3; and

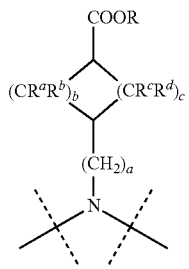

represents a cycloalkane carboxylic acid or ester thereof, selected from the group consisting of

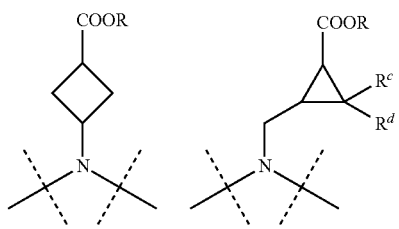

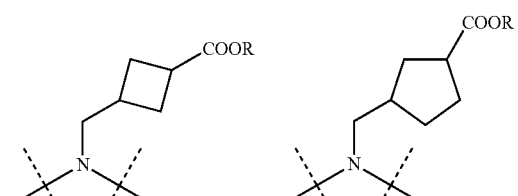

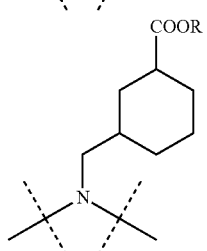

wherein $R^c$ and $R^d$ represent independently from each other H or $C_{1-4}$ alkyl;
X represents —O—CH₂—, —S—CH₂—, —CH=CH—, —CH₂—CH₂—, —C≡C— or 1,2-cyclopropandiyl;
Y represents hydrogen, halogen; $C_{1-4}$ alkyl, $C_{1-4}$ alkoxy or $C_{1-4}$ hydroxyalkyl; and
Z represents a $C_{1-4}$ aliphatic hydrocarbon bridge optionally containing one double bond, and/or one or more heteroatom selected from O, S, N and N(CH₃) or represents a $C_{2-4}$ aliphatic hydrocarbon bridge fused with a $C_{3-6}$ cycloalkyl ring optionally containing one or more double bond or with a phenyl ring or represents a $C_{1-4}$ aliphatic hydrocarbon bridge substituted with a spiro $C_{3-6}$ cycloalkyl ring optionally containing one or more double bonds.

3. A compound according to claim 1, wherein R represents hydrogen.

4. A compound according to claim 1, wherein R¹ represents a group selected from the group consisting of

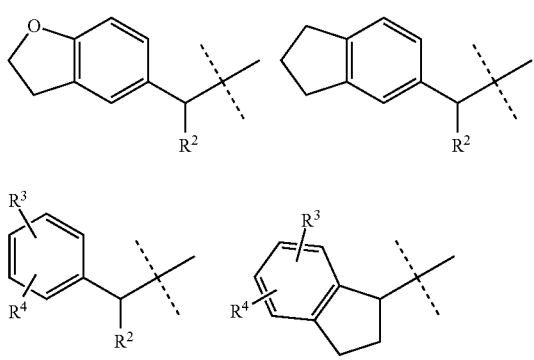

wherein
$R^2$ represents methyl or ethyl;
$R^3$ represents Cl, F, $CF_3$, CN, methyl or ethyl; and
$R^4$ represents hydrogen, Cl, F or methyl.

5. A compound according to claim 4, wherein $R^1$ represents a group selected from the group consisting of

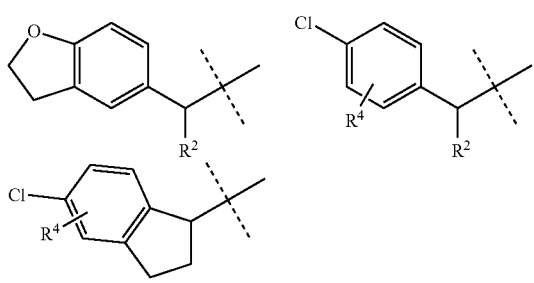

wherein
$R^2$ represents methyl or ethyl; and
$R^4$ represents hydrogen, Cl or F.

6. A compound according to claim 5, wherein $R^1$ represents a group selected from the group consisting of

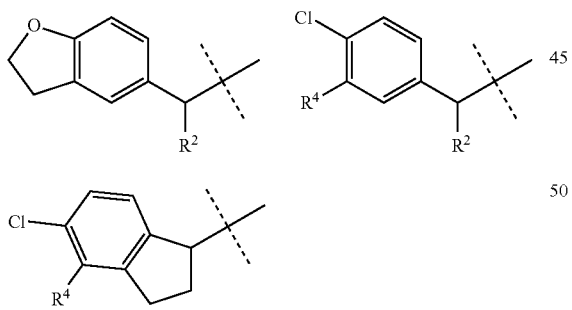

wherein
$R^2$ represents methyl or ethyl; and
$R^4$ represents hydrogen, Cl or F.

7. A compound according to claim 1, wherein X represents —O—$CH_2$—, —S—$CH_2$— or —$CH_2$—$CH_2$—.

8. A compound according to claim 1, wherein Y represents hydrogen, Cl, F, methyl, ethyl, methoxy or —$CH_2$—OH.

9. A compound according to claim 8, wherein Y represents ethyl or methoxy.

10. A compound according to claim 1, wherein Z represents —$(CH_2)_2$—, —$(CH_2)_3$—, —$CH_2$—O—, —$CH_2$—S—, —$CH_2$—N($CH_3$)—, —CH=CH—N($CH_3$)—, —N=CH—N($CH_3$)—, 1,2-cyclopropandiyl,

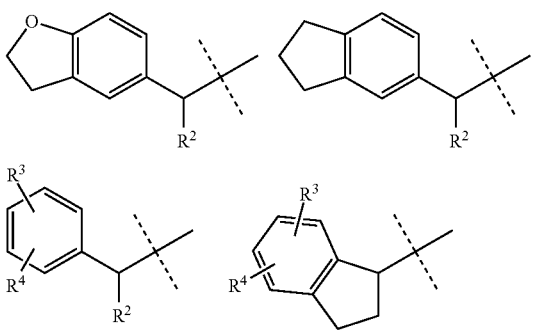

11. A compound according to claim 10, wherein Z represents —$(CH_2)_2$— or —$CH_2$—N($CH_3$)—.

12. A compound of formula 1 according to claim 1, wherein
R represents hydrogen, methyl or ethyl;
$R^1$ represents a group selected from the group consisting of

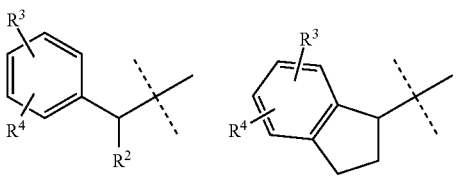

wherein
$R^2$ represents hydrogen methyl or ethyl;
$R^3$ represents hydrogen, chloro, fluoro, $CF_3$, CN, methyl or ethyl; and
$R^4$ represents hydrogen, chloro, fluoro, methyl or ethyl;
a=0 or 1; b=0, 1 or 2, c=1, 2 or 3; and

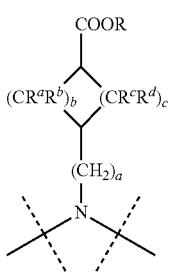

represents a cycloalkane carboxylic acid or ester thereof, selected from the group consisting of

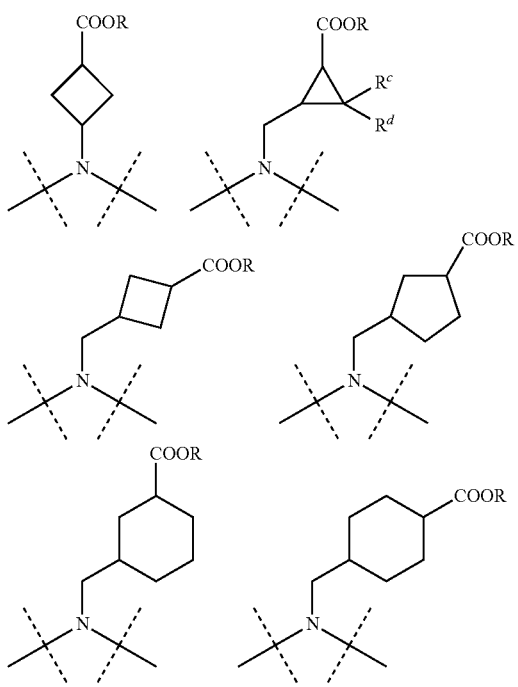

wherein $R^c$ and $R^d$ represent independently from each other H or methyl or ethyl;

X represents —O—CH$_2$—, —S—CH$_2$—, —CH=CH—, —CH$_2$—CH$_2$—, —C≡C— or 1,2-cyclopropandiyl;

Y represents chloro, fluoro, methyl, ethyl, methoxy or —CH$_2$—OH;

Z represents —(CH$_2$)$_2$—, —(CH$_2$)$_3$—, —CH$_2$—O—, —CH$_2$—S—, —CH$_2$—N(CH$_3$)—, —CH=CH—N(CH$_3$)—, —N=CH—N(CH$_3$)—, CH(CH$_2$)CH—,

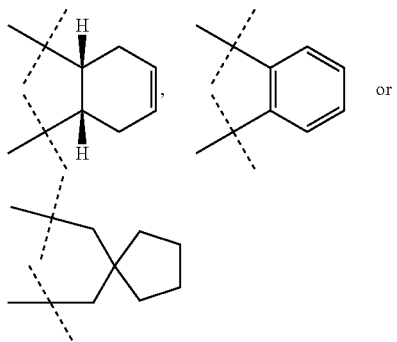

or a pharmaceutically acceptable salt or stereoisomer thereof or a pharmaceutically acceptable salt of the stereoisomer.

13. A compound according to claim 12 selected from the group consisting of trans-4-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid ethyl ester;

trans-4-[([1-(2,3-Dihydro-1-benzofuran-5-yl)ethyl]{4-[2-(2,5-dioxo-pyrrolidin-1-yl)ethoxy]-3-methoxybenzyl}amino)methyl]-cyclohexanecarboxylic acid;

cis-4-[([1-(2,3-Dihydro-1-benzofuran-5-yl)ethyl]{4-[2-(2,5-dioxo-pyrrolidin-1-yl)ethoxy]-3-methoxybenzyl}amino)methyl]-cyclohexanecarboxylic acid;

trans-4-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid;

trans-4-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid;

trans-4-[([(S)-1-(4-Chloro-phenyl)-ethyl]-{4-[2-(2,5-dioxo-pyrrolidin-1-yl)-ethoxy]-3-methoxy-benzyl}-amino)-methyl]cyclohexanecarboxylic acid;

trans-4-[([(R)-1-(4-Chloro-phenyl)-ethyl]-{4-[2-(2,5-dioxo-pyrrolidin-1-yl)-ethoxy]-3-methoxy-benzyl}-amino)-methyl]-cyclohexanecarboxylic acid;

trans-4-[([(S)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid;

cis-4-[([(S)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid;

trans-4-[([(R)-1-(4-Chloro-phenyl)-ethyl]-{4-[2-(2,5-dioxo-pyrrolidin-1-yl)-ethoxy]-3-methyl-benzyl}-amino)-methyl]-cyclohexanecarboxylic acid;

trans-4-[((5-Chloro-indan-1-yl)-{4-[2-(2,5-dioxo-pyrrolidin-1-yl)-ethoxy]-3-methoxy-benzyl}-amino)-methyl]-cyclohexanecarboxylic acid;

trans-4-[(((R)-5-Chloro-indan-1-yl)-{4-[2-(2,5-dioxo-pyrrolidin-1-yl)-ethoxy]-3-methoxy-benzyl}-amino)-methyl]-cyclohexanecarboxylic acid;

trans-4-[(((S)-5-Chloro-indan-1-yl)-{4-[2-(2,5-dioxo-pyrrolidin-1-yl)-ethoxy]-3-methoxy-benzyl}-amino)-methyl]-cyclohexanecarboxylic acid;

cis-4-[((5-Chloro-indan-1-yl)-{4-[2-(2,5-dioxo-pyrrolidin-1-yl)-ethoxy]-3-methoxy-benzyl}-amino)-methyl]-cyclohexanecarboxylic acid;

trans-4-[(((S)-4,5-Dichloro-indan-1-yl)-{4-[2-(2,5-dioxo-pyrrolidin-1-yl)-ethoxy]-3-methoxy-benzyl}-amino)-methyl]-cyclohexanecarboxylic acid hydrochloride;

trans-4-[([1-(2,3-Dihydro-benzofuran-5-yl)-ethyl]-{4-[2-(2,4-dioxo-thiazolidin-3-yl)-ethoxy]-3-methoxy-benzyl}-amino)-methyl]-cyclohexanecarboxylic acid;

trans-4-({{3-Chloro-4-[2-(2,5-dioxo-pyrrolidin-1-yl)-ethoxy]-benzyl}-[1-(2,3-dihydro-benzofuran-5-yl)-ethyl]-amino}-methyl)-cyclohexanecarboxylic acid;

trans-4-[([1-(2,3-Dihydro-benzofuran-5-yl)-ethyl]-{4-[2-(2,5-dioxo-pyrrolidin-1-yl)-ethoxy]-3-methyl-benzyl}-amino)-methyl]-cyclohexanecarboxylic acid;

trans-4-[([1-(2,3-Dihydro-benzofuran-5-yl)-propyl]-{4-[2-(2,5-dioxo-pyrrolidin-1-yl)-ethoxy]-3-methoxy-benzyl}-amino)-methyl]-cyclohexanecarboxylic acid;

trans-4-[([1-(2,3-Dihydro-benzofuran-5-yl)-ethyl]-{4-[2-(2,4-dioxo-oxazolidin-3-yl)-ethoxy]-3-methoxy-benzyl}-amino)-methyl]-cyclohexanecarboxylic acid;

trans-4-[((5-Chloro-indan-1-yl)-{3-chloro-4-[2-(3-methyl-2,5-dioxo-imidazolidin-1-yl)-ethoxy]-benzyl}-amino)-methyl]-cyclohexanecarboxylic acid;

trans-4-{[{3-Chloro-4-[2-(2,5-dioxo-pyrrolidin-1-yl)-ethoxy]-benzyl}-(5-chloro-indan-1-yl)-amino]-methyl}-cyclohexanecarboxylic acid;

trans-4-({{3-Chloro-4-[2-(3-methyl-2,5-dioxo-imidazolidin-1-yl)-ethoxy]-benzyl}-[1-(2,3-dihydro-benzofuran-5-yl)-ethyl]-amino}-methyl)-cyclohexanecarboxylic acid;

trans-4-({{3-Chloro-4-[2-(3-methyl-2,5-dioxo-imidazolidin-1-yl)-ethoxy]-benzyl}-[(S)-1-(4-chloro-phenyl)-ethyl]-amino}-methyl)-cyclohexanecarboxylic acid;
trans-4-[((5-Chloro-indan-1-yl)-{4-[2-(2,4-dioxo-thiazolidin-3-yl)-ethoxy]-3-methoxy-benzyl}-amino)-methyl]-cyclohexanecarboxylic acid;
trans-4-[([1-(4-Chloro-3-methyl-phenyl)-ethyl]-{4-[2-(2,5-dioxo-pyrrolidin-1-yl)-ethoxy]-3-methoxy-benzyl}-amino)-methyl]-cyclohexanecarboxylic acid;
trans-4-[([(S)-1-(4-Chloro-3-methyl-phenyl)-ethyl]-{4-[2-(2,5-dioxo-pyrrolidin-1-yl)-ethoxy]-3-methoxy-benzyl}-amino)-methyl]-cyclohexanecarboxylic acid;
trans-4-[([(R)-1-(4-Chloro-3-methyl-phenyl)-ethyl]-{4-[2-(2,5-dioxo-pyrrolidin-1-yl)-ethoxy]-3-methoxy-benzyl}-amino)-methyl]-cyclohexanecarboxylic acid;
trans-4-[([1-(2,3-Dihydro-benzofuran-5-yl)-propyl]-{3-methoxy-4-[2-(3-methyl-2,5-dioxo-imidazolidin-1-yl)-ethoxy]-benzyl}-amino)-methyl]-cyclohexanecarboxylic acid;
trans-4-[((5-Chloro-indan-1-yl)-{4-[2-(2,5-dioxo-pyrrolidin-1-yl)-ethoxy]-3-methyl-benzyl}-amino)-methyl]-cyclohexanecarboxylic acid;
trans-4-[(((S)-5-Chloro-indan-1-yl)-{4-[2-(2,5-dioxo-pyrrolidin-1-yl)-ethoxy]-3-methyl-benzyl}-amino)-methyl]-cyclohexanecarboxylic acid;
trans-4-[(((R)-5-Chloro-indan-1-yl)-{4-[2-(2,5-dioxo-pyrrolidin-1-yl)-ethoxy]-3-methyl-benzyl}-amino)-methyl]-cyclohexanecarboxylic acid;
trans-4-({{3-Chloro-4-[2-(2,5-dioxo-pyrrolidin-1-yl)-ethoxy]-benzyl}-[(S)-1-(4-chloro-phenyl)-ethyl]-amino}-methyl)-cyclohexanecarboxylic acid;
trans-4-[([1-(2,3-Dihydro-benzofuran-5-yl)-ethyl]-{4-[2-(2,4-dioxo-thiazolidin-3-yl)-ethoxy]-3-methyl-benzyl}-amino)-methyl]-cyclohexanecarboxylic acid;
trans-4-[([(S)-1-(4-Chloro-phenyl)-ethyl]-{4-[2-(2,4-dioxo-thiazolidin-3-yl)-ethoxy]-3-methoxy-benzyl}-amino)-methyl]-cyclohexanecarboxylic acid;
trans-4-[([1-(2,3-Dihydro-benzofuran-5-yl)-ethyl]-{4-[(E)-3-(2,5-dioxo-pyrrolidin-1-yl)-propenyl]-3-methoxy-benzyl}-amino)-methyl]-cyclohexanecarboxylic acid;
trans-4-[([(S)-1-(4-Chloro-phenyl)-ethyl]-{4-[2-(2,4-dioxo-oxazolidin-3-yl)-ethoxy]-3-methoxy-benzyl}-amino)-methyl]-cyclohexanecarboxylic acid;
trans-4-[([(S)-1-(4-Chloro-phenyl)-ethyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid;
trans-4-[([1-(2,3-Dihydro-benzofuran-5-yl)-ethyl]-{4-[2-(2,6-dioxo-piperidin-1-yl)-ethoxy]-3-methoxy-benzyl}-amino)-methyl]-cyclohexanecarboxylic acid;
trans-4-[([(S)-1-(4-Chloro-phenyl)-ethyl]-{3-methyl-4-[2-(3-methyl-2,5-dioxo-imidazolidin-1-yl)-ethoxy]-benzyl}-amino)-methyl]-cyclohexanecarboxylic acid;
trans-4-[([1-(2,3-Dihydro-benzofuran-5-yl)-ethyl]-{4-[3-(2,5-dioxo-pyrrolidin-1-yl)-propyl]-3-methoxy-benzyl}-amino)-methyl]-cyclohexanecarboxylic acid;
3-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclohexanecarboxylic acid;
trans-4-[((5-Chloro-6-methyl-indan-1-yl)-{4-[2-(2,5-dioxo-pyrrolidin-1-yl)-ethoxy]-3-methoxy-benzyl}-amino)-methyl]-cyclohexanecarboxylic acid;
trans-4-[((5-Chloro-4-methyl-indan-1-yl)-{4-[2-(2,5-dioxo-pyrrolidin-1-yl)-ethoxy]-3-methoxy-benzyl}-amino)-methyl]-cyclohexanecarboxylic acid;
trans-4-[((5-Chloro-indan-1-yl)-{4-[3-(2,5-dioxo-pyrrolidin-1-yl)-propyl]-3-methoxy-benzyl}-amino)-methyl]-cyclohexanecarboxylic acid;
trans-4-[(((R)-5-Chloro-indan-1-yl)-{4-[3-(2,5-dioxo-pyrrolidin-1-yl)-propyl]-3-methoxy-benzyl}-amino)-methyl]-cyclohexanecarboxylic acid;
trans-4-[(((S)-5-Chloro-indan-1-yl)-{4-[3-(2,5-dioxo-pyrrolidin-1-yl)-propyl]-3-methoxy-benzyl}-amino)-methyl]-cyclohexanecarboxylic acid;
trans-4-({{3-Chloro-4-[3-(2,5-dioxo-pyrrolidin-1-yl)-propyl]-benzyl}-[1-(2,3-dihydro-benzofuran-5-yl)-ethyl]-amino}-methyl)-cyclohexanecarboxylic acid;
trans-4-[((5-Chloro-indan-1-yl)-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid;
trans-4-[([1-(2,3-Dihydro-benzofuran-5-yl)-ethyl]-{4-[2-(2,5-dioxo-pyrrolidin-1-ylmethyl)-cyclopropyl]-3-methoxy-benzyl}-amino)-methyl]-cyclohexanecarboxylic acid;
trans-4-[((5-Chloro-indan-1-yl)-{3-methoxy-4-[3-(3-methyl-2,5-dioxo-imidazolidin-1-yl)-propyl]-benzyl}-amino)-methyl]-cyclohexanecarboxylic acid;
trans-4-[([(S)-1-(4-Chloro-phenyl)-ethyl]-{3-methoxy-4-[3-(3-methyl-2,5-dioxo-imidazolidin-1-yl)-propyl]-benzyl}-amino)-methyl]-cyclohexanecarboxylic acid;
trans-4-[((5-Chloro-indan-1-yl)-{3-methoxy-4-[2-(3-methyl-2,5-dioxo-imidazolidin-1-yl)-ethoxy]-benzyl}-amino)-methyl]-cyclohexanecarboxylic acid;
trans-4-[([(S)-1-(4-Chloro-phenyl)-ethyl]-{3-methoxy-4-[2-(3-methyl-2,5-dioxo-imidazolidin-1-yl)-ethoxy]-benzyl}-amino)-methyl]-cyclohexanecarboxylic acid;
trans-4-[([(S)-1-(4-Chloro-phenyl)-ethyl]-{4-[3-(2,5-dioxo-pyrrolidin-1-yl)-propyl]-3-methyl-benzyl}-amino)-methyl]-cyclohexanecarboxylic acid;
trans-4-[([(S)-1-(4-Chloro-phenyl)-ethyl]-{4-[3-(2,5-dioxo-pyrrolidin-1-yl)-prop-1-ynyl]-3-methoxy-benzyl}-amino)-methyl]-cyclohexanecarboxylic acid;
trans-4-[([(S)-1-(4-Chloro-phenyl)-ethyl]-{4-[3-(2,5-dioxo-pyrrolidin-1-yl)-propyl]-3-methoxy-benzyl}-amino)-methyl]-cyclohexanecarboxylic acid;
trans-4-[((5-Chloro-indan-1-yl)-{3-methyl-4-[2-(3-methyl-2,5-dioxo-imidazolidin-1-yl)-ethoxy]-benzyl}-amino)-methyl]-cyclohexanecarboxylic acid;
trans-4-[([(S)-1-(4-Chloro-phenyl)-ethyl]-{3-methyl-4-[2-(3-methyl-2,6-dioxo-3,6-dihydro-2H-pyrimidin-1-yl)-ethoxy]-benzyl}-amino)-methyl]-cyclohexanecarboxylic acid;
trans-4-[([1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid;
trans-4-[([1-(2,3-Dihydro-benzofuran-5-yl)-ethyl]-{3-methyl-4-[2-(3-methyl-2,6-dioxo-3,6-dihydro-2H-pyrimidin-1-yl)-ethoxy]-benzyl}-amino)-methyl]-cyclohexanecarboxylic acid;
trans-4-[([1-(4-Cyano-phenyl)-ethyl]-{4-[2-(2,5-dioxo-pyrrolidin-1-yl)-ethoxy]-3-methyl-benzyl}-amino)-methyl]-cyclohexanecarboxylic acid;
trans-4-[([1-(4-Cyano-phenyl)-ethyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid;
trans-4-[([1-(4-Chloro-phenyl)-propyl]-{4-[2-(2,5-dioxo-pyrrolidin-1-yl)-ethoxy]-3-methoxy-benzyl}-amino)-methyl]-cyclohexanecarboxylic acid;

trans-4-[([1-(4-Chloro-phenyl)-propyl]-{3-methyl-4-[2-(3-methyl-2,6-dioxo-3,6-dihydro-2H-pyrimidin-1-yl)-ethoxy]-benzyl}-amino)-methyl]-cyclohexanecarboxylic acid;

trans-4-[([1-(4-Chloro-phenyl)-propyl]-{4-[2-(2,5-dioxo-pyrrolidin-1-yl)-ethoxy]-3-methyl-benzyl}-amino)-methyl]-cyclohexanecarboxylic acid;

trans-4-[([1-(2,3-Dihydro-benzofuran-5-yl)-propyl]-{4-[3-(2,5-dioxo-pyrrolidin-1-yl)-propyl]-3-methoxy-benzyl}-amino)-methyl]-cyclohexanecarboxylic acid;

trans-4-[([1-(4-Chloro-phenyl)-propyl]-{3-methoxy-4-[2-(3-methyl-2,5-dioxo-imidazolidin-1-yl)-ethoxy]-benzyl}-amino)-methyl]-cyclohexanecarboxylic acid;

trans-4-[([1-(4-Chloro-phenyl)-propyl]-{3-methoxy-4-[2-(3-methyl-2,6-dioxo-3,6-dihydro-2H-pyrimidin-1-yl)-ethoxy]-benzyl}-amino)-methyl]-cyclohexanecarboxylic acid;

trans-4-[([1-(2,3-Dihydro-benzofuran-5-yl)-propyl]-{4-[2-(2,5-dioxo-pyrrolidin-1-yl)-ethoxy]-3-methyl-benzyl}-amino)-methyl]-cyclohexanecarboxylic acid;

trans-4-[([1-(4-Chloro-phenyl)-propyl]-{3-methyl-4-[2-(3-methyl-2,5-dioxo-imidazolidin-1-yl)-ethoxy]-benzyl}-amino)-methyl]-cyclohexanecarboxylic acid;

trans-4-[(((S)-5-Chloro-indan-1-yl)-{4-[2-(2,5-dioxo-pyrrolidin-1-yl)-ethoxy]-3-ethyl-benzyl}-amino)-methyl]-cyclohexanecarboxylic acid;

trans-4-[(((S)-5-Chloro-indan-1-yl)-{4-[2-(2,5-dioxo-pyrrolidin-1-yl)-ethoxy]-3-fluoro-benzyl}-amino)-methyl]-cyclohexanecarboxylic acid;

trans-4-[([(S)-1-(4-Chloro-phenyl)-ethyl]-{4-[2-(2,5-dioxo-pyrrolidin-1-yl)-ethoxy]-3-fluoro-benzyl}-amino)-methyl]-cyclohexanecarboxylic acid;

trans-4-[(((S)-5,6-Dichloro-indan-1-yl)-{4-[2-(2,5-dioxo-pyrrolidin-1-yl)-ethoxy]-3-methoxy-benzyl}-amino)-methyl]-cyclohexanecarboxylic acid;

trans-4-[([(S)-1-(4-Chloro-phenyl)-ethyl]-{4-[2-(2,5-dioxo-pyrrolidin-1-yl)-ethoxy]-3-ethyl-benzyl}-amino)-methyl]-cyclohexanecarboxylic acid;

trans-4-[([1-(2,3-Dihydro-benzofuran-5-yl)-ethyl]-{4-[2-(2,5-dioxo-pyrrolidin-1-yl)-ethoxy]-3-ethyl-benzyl}-amino)-methyl]-cyclohexanecarboxylic acid;

trans-4-[([1-(3,4-Dichloro-phenyl)-ethyl]-{4-[2-(2,5-dioxo-pyrrolidin-1-yl)-ethoxy]-3-methoxy-benzyl}-amino)-methyl]-cyclohexanecarboxylic acid;

trans-4-[([1-(3,4-Dichloro-phenyl)-ethyl]-{4-[2-(2,5-dioxo-pyrrolidin-1-yl)-ethoxy]-3-methyl-benzyl}-amino)-methyl]-cyclohexanecarboxylic acid;

trans-4-[([(S)-1-(4-Chloro-phenyl)-ethyl]-{4-[2-(2,5-dioxo-pyrrolidin-1-yl)-ethoxy]-benzyl}-amino)-methyl]-cyclohexanecarboxylic acid;

trans-4-[([1-(3,4-Dichloro-phenyl)-ethyl]-{3-methyl-4-[2-(3-methyl-2,5-dioxo-imidazolidin-1-yl)-ethoxy]-benzyl}-amino)-methyl]-cyclohexanecarboxylic acid;

trans-4-({{4-[2-(2,5-Dioxo-pyrrolidin-1-yl)-ethoxy]-3-methoxy-benzyl}-[1-(4-ethyl-phenyl)-ethyl]-amino}-methyl)-cyclohexanecarboxylic acid;

trans-4-[([1-(4-Chloro-3-fluoro-phenyl)-ethyl]-{4-[2-(2,5-dioxo-pyrrolidin-1-yl)-ethoxy]-3-methoxy-benzyl}-amino)-methyl]-cyclohexanecarboxylic acid;

trans-4-{[{4-[2-(2,5-Dioxo-pyrrolidin-1-yl)-ethoxy]-3-methyl-benzyl}-(1-p-tolyl-ethyl)-amino]-methyl}-cyclohexanecarboxylic acid;

trans-4-{[{4-[2-(2,5-Dioxo-pyrrolidin-1-yl)-ethoxy]-3-methoxy-benzyl}-(1-p-tolyl-ethyl)-amino]-methyl}-cyclohexanecarboxylic acid;

trans-4-[([(S)-1-(4-Chloro-phenyl)-ethyl]-{4-[2-(2,5-dioxo-pyrrolidin-1-yl)-ethoxy]-3-hydroxymethyl-benzyl}-amino)-methyl]-cyclohexanecarboxylic acid;

trans-4-[(((S)-4,5-Dichloro-indan-1-yl)-{4-[2-(2,5-dioxo-pyrrolidin-1-yl)-ethoxy]-3-ethyl-benzyl}-amino)-methyl]-cyclohexanecarboxylic acid;

trans-4-[([(S)-1-(4-Chloro-phenyl)-ethyl]-{4-[2-(2,5-dioxo-pyrrolidin-1-yl)-ethylsulfanyl]-3-methoxy-benzyl}-amino)-methyl]-cyclohexanecarboxylic acid;

trans-4-[(((S)-5-Chloro-indan-1-yl)-{4-[2-(2,5-dioxo-pyrrolidin-1-yl)-ethylsulfanyl]-3-methoxy-benzyl}-amino)-methyl]-cyclohexanecarboxylic acid;

trans-4-[([1-(4-Chloro-3-fluoro-phenyl)-ethyl]-{4-[2-(2,5-dioxo-pyrrolidin-1-yl)-ethoxy]-3-ethyl-benzyl}-amino)-methyl]-cyclohexanecarboxylic acid;

trans-4-[([(R)-1-(4-Chloro-3-fluoro-phenyl)-ethyl]-{4-[2-(2,5-dioxo-pyrrolidin-1-yl)-ethoxy]-3-ethyl-benzyl}-amino)-methyl]-cyclohexanecarboxylic acid;

trans-4-[([(S)-1-(4-Chloro-3-fluoro-phenyl)-ethyl]-{4-[2-(2,5-dioxo-pyrrolidin-1-yl)-ethoxy]-3-ethyl-benzyl}-amino)-methyl]-cyclohexanecarboxylic acid;

trans-4-[([1-(4-Chloro-3-fluoro-phenyl)-ethyl]-{4-[2-(2,5-dioxo-pyrrolidin-1-yl)-ethoxy]-3-fluoro-benzyl}-amino)-methyl]-cyclohexanecarboxylic acid;

trans-4-[(((4-Chloro-5-fluoro-indan-1-yl)-{4-[2-(2,5-dioxo-pyrrolidin-1-yl)-ethoxy]-3-methoxy-benzyl}-amino)-methyl]-cyclohexanecarboxylic acid;

trans-4-[(((6-Chloro-5-fluoro-indan-1-yl)-{4-[2-(2,5-dioxo-pyrrolidin-1-yl)-ethoxy]-3-methoxy-benzyl}-amino)-methyl]-cyclohexanecarboxylic acid;

trans-4-[(((6-Chloro-5-fluoro-indan-1-yl)-{4-[2-(2,5-dioxo-pyrrolidin-1-yl)-ethoxy]-3-ethyl-benzyl}-amino)-methyl]-cyclohexanecarboxylic acid;

trans-4-[(((4-Chloro-5-fluoro-indan-1-yl)-{4-[2-(2,5-dioxo-pyrrolidin-1-yl)-ethoxy]-3-ethyl-benzyl}-amino)-methyl]-cyclohexanecarboxylic acid;

trans-4-[(((6-Chloro-5-fluoro-indan-1-yl)-{4-[2-(2,5-dioxo-pyrrolidin-1-yl)-ethoxy]-3-fluoro-benzyl}-amino)-methyl]-cyclohexanecarboxylic acid;

trans-4-[(((5-Chloro-6-fluoro-indan-1-yl)-{4-[2-(2,5-dioxo-pyrrolidin-1-yl)-ethoxy]-3-methoxy-benzyl}-amino)-methyl]-cyclohexanecarboxylic acid;

(1R,3R)-3-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclopentanecarboxylic acid;

(1S,3S)-3-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclopentanecarboxylic acid;

(1R,3S)-3-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclopentanecarboxylic acid;

(1S,3R)-3-[([(S)-1-(4-Chloro-phenyl)-ethyl]-{4-[2-(2,5-dioxo-pyrrolidin-1-yl)-ethoxy]-3-methoxy-benzyl}-amino)-methyl]-cyclopentanecarboxylic acid;

(1R,3S)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid;

(1R,3R)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid;

(1R,3R)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid;

(1S,3R)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid;

(1R,3S)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid;

(1S,3R)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid;

(1S,3S)-3-[([(R)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid;

(1S,3S)-3-[([(S)-1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopentanecarboxylic acid;

(1R,2R)-2-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopropanecarboxylic acid ethyl ester;

(1R,2R)-2-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopropanecarboxylic acid;

(1S,2R)-2-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopropanecarboxylic acid ethyl ester;

(1S,2R)-2-[([1-(2,3-Dihydro-benzofuran-5-yl)-ethyl]-{4-[2-(2,5-dioxo-pyrrolidin-1-yl)-ethoxy]-3-methoxy-benzyl}-amino)-methyl]-cyclopropanecarboxylic acid;

(1R,3R)-3-[([1-(4-Chloro-phenyl)-propyl]-{3-methyl-4-[2-(3-methyl-2,5-dioxo-imidazolidin-1-yl)-ethoxy]-benzyl}-amino)-methyl]-2,2-dimethyl-cyclopropanecarboxylic acid;

(1S,3S)-3-[([1-(4-Chloro-phenyl)-propyl]-{3-methoxy-4-[2-(3-methyl-2,5-dioxo-imidazolidin-1-yl)-ethoxy]-benzyl}-amino)-methyl]-2,2-dimethyl-cyclopropanecarboxylic acid;

(1S,3S)-3-[([1-(4-Chloro-phenyl)-propyl]-{4-[2-(2,5-dioxo-pyrrolidin-1-yl)-ethoxy]-3-methoxy-benzyl}-amino)-methyl]-2,2-dimethyl-cyclopropanecarboxylic acid;

(1R,3R)-3-[([1-(4-Chloro-phenyl)-propyl]-{4-[2-(2,5-dioxo-pyrrolidin-1-yl)-ethoxy]-3-methyl-benzyl}-amino)-methyl]-2,2-dimethyl-cyclopropanecarboxylic acid;

1-[((5-Chloro-indan-1-yl)-{4-[2-(2,5-dioxo-pyrrolidin-1-yl)-ethoxy]-3-methoxy-benzyl}-amino)-methyl]-cyclopropanecarboxylic acid;

trans-3-([1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid;

cis-3-([1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid;

cis-3-([[(R)-1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid;

cis-3-([[(S)-1-(2,3-Dihydro-benzofuran-5-yl)-ethyl]-{3-methoxy-4-[2-(3-methyl-2,6-dioxo-3,6-dihydro-2H-pyrimidin-1-yl)-ethoxy]-benzyl}-amino)-cyclobutanecarboxylic acid;

trans-3-([1-(4-Chloro-3-fluoro-phenyl)-ethyl]-{4-[2-(2,5-dioxo-pyrrolidin-1-yl)-ethoxy]-3-methyl-benzyl}-amino)-cyclobutanecarboxylic acid;

cis-3-([1-(4-Chloro-3-fluoro-phenyl)-ethyl]-{4-[2-(2,5-dioxo-pyrrolidin-1-yl)-ethoxy]-3-methyl-benzyl}-amino)-cyclobutanecarboxylic acid;

3-([1-(2,3-Dihydro-benzofuran-5-yl)-ethyl]-{4-[2-(2,5-dioxo-pyrrolidin-1-yl)-ethoxy]-3-methoxy-benzyl}-amino)-cyclobutanecarboxylic acid;

3-((5-Chloro-indan-1-yl)-{4-[2-(2,5-dioxo-pyrrolidin-1-yl)-ethoxy]-3-methoxy-benzyl}-amino)-cyclobutanecarboxylic acid;

trans-3-([(R)-1-(4-Chloro-3-methyl-phenyl)-ethyl]-{4-[2-(2,5-dioxo-pyrrolidin-1-yl)-ethoxy]-3-methyl-benzyl}-amino)-cyclobutanecarboxylic acid;

cis-3-([(R)-1-(4-Chloro-3-methyl-phenyl)-ethyl]-{4-[2-(2,5-dioxo-pyrrolidin-1-yl)-ethoxy]-3-methyl-benzyl}-amino)-cyclobutanecarboxylic acid;

trans-3-([(S)-1-(4-Chloro-3-methyl-phenyl)-ethyl]-{4-[2-(2,5-dioxo-pyrrolidin-1-yl)-ethoxy]-3-methyl-benzyl}-amino)-cyclobutanecarboxylic acid;

cis-3-([(S)-1-(4-Chloro-3-methyl-phenyl)-ethyl]-{4-[2-(2,5-dioxo-pyrrolidin-1-yl)-ethoxy]-3-methyl-benzyl}-amino)-cyclobutanecarboxylic acid;

cis-3-([(R)-1-(4-Chloro-phenyl)-ethyl]-{4-[2-(2,5-dioxo-pyrrolidin-1-yl)-ethoxy]-3-methyl-benzyl}-amino)-cyclobutanecarboxylic acid;

cis-3-((5-Chloro-indan-1-yl)-{4-[2-(2,5-dioxo-pyrrolidin-1-yl)-ethoxy]-3-methyl-benzyl}-amino)-cyclobutanecarboxylic acid;

cis-3-([1-(2,3-Dihydro-benzofuran-5-yl)-ethyl]-{3-methyl-4-[2-(3-methyl-2,6-dioxo-3,6-dihydro-2H-pyrimidin-1-yl)-ethoxy]-benzyl}-amino)-cyclobutanecarboxylic acid;

cis-3-([1-(2,3-Dihydro-benzofuran-5-yl)-propyl]-{4-[2-(2,5-dioxo-pyrrolidin-1-yl)-ethoxy]-3-methyl-benzyl}-amino)-cyclobutanecarboxylic acid;

cis-3-([(R)-1-(4-Chloro-phenyl)-ethyl]-{3-methyl-4-[2-(3-methyl-2,6-dioxo-3,6-dihydro-2H-pyrimidin-1-yl)-ethoxy]-benzyl}-amino)-cyclobutanecarboxylic acid;

cis-3-([1-(3,4-Dichloro-phenyl)-ethyl]-{4-[2-(2,5-dioxo-pyrrolidin-1-yl)-ethoxy]-3-methoxy-benzyl}-amino)-cyclobutanecarboxylic acid;

cis-3-([1-(3,4-Dichloro-phenyl)-ethyl]-{4-[2-(2,5-dioxo-pyrrolidin-1-yl)-ethoxy]-3-methyl-benzyl}-amino)-cyclobutanecarboxylic acid;

cis-3-([1-(3,4-Dichloro-phenyl)-ethyl]-{4-[2-(2,5-dioxo-pyrrolidin-1-yl)-ethoxy]-3-ethyl-benzyl}-amino)-cyclobutanecarboxylic acid;

cis-3-([1-(4-Chloro-3-fluoro-phenyl)-ethyl]-{4-[2-(2,5-dioxo-pyrrolidin-1-yl)-ethoxy]-3-ethyl-benzyl}-amino)-cyclobutanecarboxylic acid;

cis-3-([1-(3,4-Dichloro-phenyl)-propyl]-{4-[2-(2,5-dioxo-pyrrolidin-1-yl)-ethoxy]-3-methoxy-benzyl}-amino)-cyclobutanecarboxylic acid;

cis-3-([1-(4-Chloro-3-fluoro-phenyl)-ethyl]-{4-[2-(2,5-dioxo-pyrrolidin-1-yl)-ethoxy]-3-methoxy-benzyl}-amino)-cyclobutanecarboxylic acid;

cis-3-([(R)-1-(4-Chloro-phenyl)-ethyl]-{4-[3-(2,5-dioxo-pyrrolidin-1-yl)-propyl]-3-methyl-benzyl}-amino)-cyclobutanecarboxylic acid;

trans-4-{[{4-[2-(2,5-Dioxo-pyrrolidin-1-yl)-ethoxy]-3-methoxy-benzyl}-(1-indan-5-yl-ethyl)-amino]-methyl}-cyclohexanecarboxylic acid;

trans-4-[((1-Indan-5-yl-ethyl)-{3-methoxy-4-[2-(3-methyl-2,5-dioxo-imidazolidin-1-yl)-ethoxy]-benzyl}-amino)-methyl]-cyclohexanecarboxylic acid;

cis,trans-4-[(((S)-5-Chloro-indan-1-yl)-{4-[2-(2,4-dioxo-3-aza-bicyclo[3.1.0]hex-3-yl)-ethoxy]-3-methoxy-benzyl}-amino)-methyl]-cyclohexanecarboxylic acid;

trans-4-[(((S)-5-Chloro-indan-1-yl)-{4-[2-(7,9-dioxo-8-aza-spiro[4.5]dec-8-yl)-ethoxy]-3-methoxy-benzyl}-amino)-methyl]-cyclohexanecarboxylic acid;

trans-4-[(((S)-5-Chloro-4-fluoro-indan-1-yl)-{4-[2-(2,5-dioxo-pyrrolidin-1-yl)-ethoxy]-3-methoxy-benzyl}-amino)-methyl]-cyclohexanecarboxylic acid;

trans-4-[(((S)-5-Chloro-4-fluoro-indan-1-yl)-{4-[2-(2,5-dioxo-pyrrolidin-1-yl)-ethoxy]-3-ethyl-benzyl}-amino)-methyl]-cyclohexanecarboxylic acid;

cis-3-([(R)-1-(4-Chloro-3-fluoro-phenyl)-ethyl]-{4-[2-(2,5-dioxo-pyrrolidin-1-yl)-ethoxy]-3-methoxy-benzyl}-amino)-cyclobutanecarboxylic acid;

cis-3-([(R)-1-(4-Chloro-3-fluoro-phenyl)-ethyl]-{4-[2-(2,5-dioxo-pyrrolidin-1-yl)-ethoxy]-3-ethyl-benzyl}-amino)-cyclobutanecarboxylic acid;

cis-3-([(R)-1-(3,4-Dichloro-phenyl)-ethyl]-{4-[2-(2,5-dioxo-pyrrolidin-1-yl)-ethoxy]-3-methoxy-benzyl}-amino)-cyclobutanecarboxylic acid;

cis-3-([(R)-1-(4-Chloro-phenyl)-ethyl]-{3-methyl-4-[2-(3-methyl-2,5-dioxo-imidazolidin-1-yl)-ethoxy]-benzyl}-amino)-cyclobutanecarboxylic acid;

trans-4-({{4-[2-(2,5-Dioxo-pyrrolidin-1-yl)-ethoxy]-3-methoxy-benzyl}-[1-(4-trifluoromethyl-phenyl)-ethyl]-amino}-methyl)-cyclohexanecarboxylic acid;

trans-4-[(((S)-5-Chloro-indan-1-yl)-{4-[2-((3aS,7aR)-1,3-dioxo-1,3,3a,4,7,7a-hexahydro-isoindol-2-yl)-ethoxy]-3-methoxy-benzyl}-amino)-methyl]-cyclohexanecarboxylic acid hydrochloride;

trans-4-[(((S)-5-Chloro-indan-1-yl)-{4-[2-(1,3-dioxo-1,3-dihydro-isoindol-2-yl)-ethoxy]-3-methoxy-benzyl}-amino)-methyl]-cyclohexanecarboxylic acid hydrochloride;

trans-[(((S)-5-Chloro-4-fluoro-indan-1-yl)-{3-methyl-4-[2-(3-methyl-2,5-dioxo-imidazolidin-1-yl)-ethoxy]-benzyl}-amino)-methyl]-cyclohexanecarboxylic acid;

3-[(((S)-5-Chloro-indan-1-yl)-{4-[2-(2,5-dioxo-pyrrolidin-1-yl)-ethoxy]-3-methoxy-benzyl}-amino)-methyl]-cyclobutanecarboxylic acid;

cis-3-(((R)-1-Indan-5-yl-ethyl)-{3-methoxy-4-[2-(3-methyl-2,6-dioxo-3,6-dihydro-2H-pyrimidin-1-yl)-ethoxy]-benzyl}-amino)-cyclobutanecarboxylic acid; and trans-3-(((R)-1-Indan-5-yl-ethyl)-{3-methoxy-4-[2-(3-methyl-2,6-dioxo-3,6-dihydro-2H-pyrimidin-1-yl)-ethoxy]-benzyl}-amino)-cyclobutanecarboxylic acid, or a pharmaceutically acceptable salt or stereoisomer thereof or a pharmaceutically acceptable salt of the stereoisomer.

14. A process for the preparation of a compound according to claim 1, comprising the steps of reductive amination of a benzaldehyde of formula 4

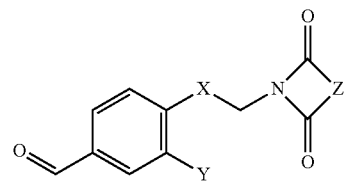

wherein X, Y and Z have the meaning as defined in claim 1, with a primary amine of formula 5

$R^1$—$NH_2$     5 wherein $R^1$ has the meaning as defined in claim 1; reacting the obtained secondary amine of formula 2

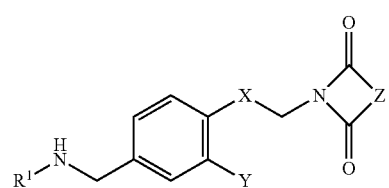

with a formyl- or oxocycloalkane carboxylic acid ester of formula 3

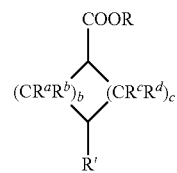

wherein R, $R^a$, $R^b$, $R^c$, $R^d$, b, and c have the meaning as defined in claim 1 and R' represents —CHO or =O to obtain an ester of a compound according to claim 1; and optionally hydrolyzing said ester to obtain a compound according to claim 1.

15. A pharmaceutical composition comprising at least one compound according to claim 1 and at least one pharmaceutically acceptable excipient.

16. A compound of formula 2

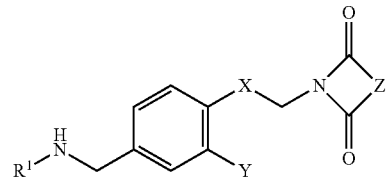

wherein
R¹ represents a group selected from the group consisting of

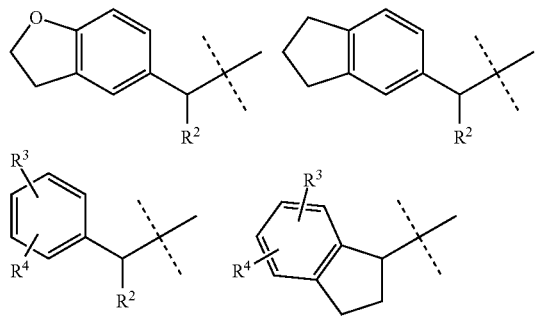

wherein
R² represents hydrogen or $C_{1-4}$ alkyl group;
R³ represents hydrogen, halogen, $CF_3$, CN or $C_{1-4}$ alkyl; and
R⁴ represents hydrogen, halogen or $C_{1-4}$ alkyl;
X represents a $C_2$ aliphatic hydrocarbon bridge optionally containing a double bond or a triple bond or a heteroatom selected from O and S, or —CH(CH₂)CH—;
Y represents hydrogen, halogen, $C_{1-4}$ alkyl, $C_{1-4}$ alkoxy or $C_{1-4}$ hydroxyalkyl;
Z represents a $C_{1-4}$ aliphatic hydrocarbon bridge optionally containing one double bond, and/or one or more heteroatom selected from O, S, N and N(CH₃) or represents a $C_{2-4}$ aliphatic hydrocarbon bridge fused with a $C_{3-6}$ cycloalkyl ring optionally containing one or more double bond or with a phenyl ring or represents a $C_{1-4}$ aliphatic hydrocarbon bridge substituted with a spiro $C_{3-6}$ cycloalkyl ring optionally containing one or more double bond;
or a salt thereof.

* * * * *

UNITED STATES PATENT AND TRADEMARK OFFICE
CERTIFICATE OF CORRECTION

PATENT NO. : 9,073,853 B2
APPLICATION NO. : 14/294885
DATED : July 7, 2015
INVENTOR(S) : Imre Bata et al.

It is certified that error appears in the above-identified patent and that said Letters Patent is hereby corrected as shown below:

On The Title Page, Item (56) References Cited

On page 2, in column 1, under "Other Publications", line 29, delete "(2007)," and insert -- (2006), --, therefor.

Signed and Sealed this
Sixteenth Day of February, 2016

Michelle K. Lee
*Director of the United States Patent and Trademark Office*